(12) United States Patent
Mire et al.

(10) Patent No.: US 7,974,677 B2
(45) Date of Patent: Jul. 5, 2011

(54) METHOD AND APPARATUS FOR PREPLANNING A SURGICAL PROCEDURE

(75) Inventors: David A. Mire, Cordova, TN (US); Hai H. Trieu, Cordova, TN (US); Janice Dugger, Westminster, CO (US); Mark W. Hunter, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 9 days.

(21) Appl. No.: 12/473,557

(22) Filed: May 28, 2009

(65) Prior Publication Data

US 2009/0234217 A1    Sep. 17, 2009

Related U.S. Application Data

(60) Division of application No. 10/794,716, filed on Mar. 5, 2004, now Pat. No. 7,542,791, which is a continuation-in-part of application No. 10/423,515, filed on Apr. 25, 2003, which is a continuation-in-part of application No. 10/354,562, filed on Jan. 30, 2003, now Pat. No. 7,660,623.

(51) Int. Cl.
*A61B 5/05* (2006.01)

(52) U.S. Cl. .................................. 600/407; 600/411

(58) Field of Classification Search .................. 600/407; 378/42; 623/7.11; 700/245
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |

(Continued)

FOREIGN PATENT DOCUMENTS

CA    964149 A1    3/1975

(Continued)

OTHER PUBLICATIONS

"Prestige Cervical Disc System Surgical Technique", 12 pgs.

(Continued)

*Primary Examiner* — Long V Le
*Assistant Examiner* — Michael T Rozanski
(74) *Attorney, Agent, or Firm* — Harness, Dickey

(57) ABSTRACT

A method and system to assist in a selection and planning of procedure and assist in selecting a prosthetic for the procedure. Generally, the system allows for image acquisition of a selected area of the anatomy. A model may be formed of the anatomy from the acquired images. The system may also allow for navigational tracking of the procedure to ensure that the procedure is substantially carried out relative to the selected plan.

48 Claims, 26 Drawing Sheets

U.S. PATENT DOCUMENTS

| | | |
|---|---|---|
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,584,994 A | 4/1986 | Bamberger et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |

| Patent | Date | Inventor |
|---|---|---|
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,415,660 A | 5/1995 | Campbell et al. |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,466,261 A | 11/1995 | Richelsoph |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |

| Patent No. | Date | Inventor(s) |
|---|---|---|
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,824,085 A | 10/1998 | Sahay et al. |
| 5,825,908 A | 10/1998 | Pieper et al. |
| 5,828,725 A | 10/1998 | Levinson |
| 5,828,770 A | 10/1998 | Leis et al. |
| 5,829,444 A | 11/1998 | Ferre et al. |
| 5,830,222 A | 11/1998 | Makower |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,957,844 A | 9/1999 | Dekel et al. |
| 5,961,553 A | 10/1999 | Coty et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |

| | | | | | | |
|---|---|---|---|---|---|---|
| 6,147,480 | A | 11/2000 | Osadchy et al. | DE | 4225112 | 12/1993 |
| 6,149,592 | A | 11/2000 | Yanof et al. | DE | 4233978 | 4/1994 |
| 6,156,067 | A | 12/2000 | Bryan et al. | DE | 19715202 | 10/1998 |
| 6,161,032 | A | 12/2000 | Acker | DE | 19751761 | 10/1998 |
| 6,165,181 | A | 12/2000 | Heilbrun et al. | DE | 19832296 | 2/1999 |
| 6,167,296 | A | 12/2000 | Shahidi | DE | 19747427 | 5/1999 |
| 6,172,499 | B1 | 1/2001 | Ashe | DE | 19856013 A1 | 6/2000 |
| 6,175,756 | B1 | 1/2001 | Ferre et al. | DE | 10013519 A1 | 10/2001 |
| 6,178,345 | B1 | 1/2001 | Vilsmeier et al. | DE | 20111479 | 10/2001 |
| 6,190,414 | B1 | 2/2001 | Young et al. | DE | 10085137 | 7/2002 |
| 6,194,639 | B1 | 2/2001 | Botella et al. | EP | 0062941 | 10/1982 |
| 6,201,387 | B1 | 3/2001 | Govari | EP | 0119660 A1 | 9/1984 |
| 6,203,497 | B1 | 3/2001 | Dekel et al. | EP | 0155857 | 9/1985 |
| 6,205,411 | B1 | 3/2001 | DiGioia, III et al. | EP | 0319844 | 6/1989 |
| 6,211,666 | B1 | 4/2001 | Acker | EP | 0326768 | 8/1989 |
| 6,223,067 | B1 | 4/2001 | Vilsmeier et al. | EP | 0350996 A1 | 1/1990 |
| 6,233,476 | B1 | 5/2001 | Strommer et al. | EP | 0419729 A1 | 4/1991 |
| 6,245,109 | B1 | 6/2001 | Mendes et al. | EP | 0427358 | 5/1991 |
| 6,246,231 | B1 | 6/2001 | Ashe | EP | 0456103 | 11/1991 |
| 6,259,942 | B1 | 7/2001 | Westermann et al. | EP | 0581704 A1 | 2/1994 |
| 6,273,896 | B1 | 8/2001 | Franck et al. | EP | 0651968 A1 | 5/1995 |
| 6,285,902 | B1 | 9/2001 | Kienzle, III et al. | EP | 0655138 A1 | 5/1995 |
| 6,298,262 | B1 | 10/2001 | Franck et al. | EP | 0820731 A2 | 1/1998 |
| 6,314,310 | B1 | 11/2001 | Ben-Haim et al. | EP | 0894473 A2 | 2/1999 |
| 6,332,089 | B1 | 12/2001 | Acker et al. | EP | 0908146 A2 | 4/1999 |
| 6,332,887 | B1 | 12/2001 | Knox | EP | 0930046 | 7/1999 |
| 6,341,231 | B1 | 1/2002 | Ferre et al. | EP | 1057461 A1 | 12/2000 |
| 6,348,058 | B1 | 2/2002 | Melkent et al. | EP | 1103229 A2 | 5/2001 |
| 6,351,659 | B1 | 2/2002 | Vilsmeier | EP | 1188421 A2 | 3/2002 |
| 6,375,682 | B1 | 4/2002 | Fleischmann et al. | EP | 1442715 A2 | 8/2004 |
| 6,381,485 | B1 | 4/2002 | Hunter et al. | FR | 2417970 A1 | 9/1979 |
| 6,424,856 | B1 | 7/2002 | Vilsmeier et al. | FR | 2618211 | 1/1989 |
| 6,427,314 | B1 | 8/2002 | Acker | GB | 1243353 A | 8/1971 |
| 6,428,547 | B1 | 8/2002 | Vilsmeier et al. | GB | 2094490 A | 9/1982 |
| 6,434,415 | B1 | 8/2002 | Foley et al. | GB | 2164856 A | 4/1986 |
| 6,437,567 | B1 | 8/2002 | Schenck et al. | JP | 62327 | 6/1985 |
| 6,445,943 | B1 | 9/2002 | Ferre et al. | JP | 63240851 | 10/1988 |
| 6,466,261 | B1 | 10/2002 | Nakamura | JP | 3267054 | 11/1991 |
| 6,470,207 | B1 | 10/2002 | Simon et al. | JP | 6194639 | 7/1994 |
| 6,474,341 | B1 | 11/2002 | Hunter et al. | JP | 2765738 | 6/1998 |
| 6,478,802 | B2 | 11/2002 | Kienzle, III et al. | WO | WO-8809151 A1 | 12/1988 |
| 6,484,049 | B1 | 11/2002 | Seeley et al. | WO | WO-8905123 | 6/1989 |
| 6,490,475 | B1 | 12/2002 | Seeley et al. | WO | WO-9005494 A1 | 5/1990 |
| 6,493,573 | B1 | 12/2002 | Martinelli et al. | WO | WO-9103982 A1 | 4/1991 |
| 6,498,944 | B1 | 12/2002 | Ben-Haim et al. | WO | WO-9104711 A1 | 4/1991 |
| 6,499,488 | B1 | 12/2002 | Hunter et al. | WO | WO-9107726 A1 | 5/1991 |
| 6,516,046 | B1 | 2/2003 | Frohlich et al. | WO | WO-9203090 A1 | 3/1992 |
| 6,527,443 | B1 | 3/2003 | Vilsmeier et al. | WO | WO-9206645 A1 | 4/1992 |
| 6,551,325 | B2 | 4/2003 | Neubauer et al. | WO | WO-9404938 A1 | 3/1994 |
| 6,584,174 | B2 | 6/2003 | Schubert et al. | WO | WO-9423647 A1 | 10/1994 |
| 6,609,022 | B2 | 8/2003 | Vilsmeier et al. | WO | WO-9424933 A1 | 11/1994 |
| 6,611,700 | B1 | 8/2003 | Vilsmeier et al. | WO | WO-9507055 A1 | 3/1995 |
| 6,640,128 | B2 | 10/2003 | Vilsmeier et al. | WO | WO-9611624 | 4/1996 |
| 6,694,162 | B2 | 2/2004 | Hartlep | WO | WO-9632059 A1 | 10/1996 |
| 6,701,179 | B1 | 3/2004 | Martinelli et al. | WO | WO-9736192 A1 | 10/1997 |
| 6,895,268 | B1 | 5/2005 | Rahn et al. | WO | WO-9749453 A1 | 12/1997 |
| 6,947,786 | B2 | 9/2005 | Simon et al. | WO | WO-9808554 A1 | 3/1998 |
| 2001/0007918 | A1 | 7/2001 | Vilsmeier et al. | WO | WO-9838908 A1 | 9/1998 |
| 2002/0077540 | A1 | 6/2002 | Kienzle | WO | WO-9915097 A2 | 4/1999 |
| 2002/0087163 | A1 | 7/2002 | Dixon et al. | WO | WO-9921498 A1 | 5/1999 |
| 2002/0095081 | A1 | 7/2002 | Vilsmeier et al. | WO | WO-9923956 A1 | 5/1999 |
| 2003/0028196 | A1 | 2/2003 | Bonutti | WO | WO-9926549 A1 | 6/1999 |
| 2003/0069591 | A1 | 4/2003 | Carson et al. | WO | WO-9927839 A2 | 6/1999 |
| 2003/0120150 | A1 | 6/2003 | Govari | WO | WO-9929253 A1 | 6/1999 |
| 2003/0194505 | A1 | 10/2003 | Milbocker | WO | WO-9933406 A1 | 7/1999 |
| 2004/0024309 | A1 | 2/2004 | Ferre et al. | WO | WO-9937208 A1 | 7/1999 |
| 2004/0097952 | A1 | 5/2004 | Sarin et al. | WO | WO-9938449 A1 | 8/1999 |
| 2004/0236424 | A1 | 11/2004 | Berez et al. | WO | WO-9952094 A1 | 10/1999 |
| 2004/0254584 | A1 | 12/2004 | Sarin et al. | WO | WO-9960939 A1 | 12/1999 |
| 2005/0043621 | A1 | 2/2005 | Perlin | WO | WO-0023015 A1 | 4/2000 |
| 2005/0254814 | A1 | 11/2005 | Sakamoto | WO | WO-0130437 A1 | 5/2001 |
| | | FOREIGN PATENT DOCUMENTS | | WO | WO-0176497 A1 | 10/2001 |
| DE | | 3042343 A1 | 6/1982 | WO | WO-0237935 A2 | 5/2002 |
| DE | | 3508730 | 9/1986 | WO | WO-02067783 A2 | 9/2002 |
| DE | | 3717871 | 12/1988 | WO | WO-03039377 A1 | 5/2003 |
| DE | | 3831278 A1 | 3/1989 | WO | WO-03079940 A2 | 10/2003 |
| DE | | 3838011 | 7/1989 | | | |
| DE | | 4213426 A1 | 10/1992 | | | |

OTHER PUBLICATIONS

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensional Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2, (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedip Surgery," CAR '98, pp. 716-722.

Brown, R., M.D., A Stereotactic Head Frame for Use with CT Body Scanners, Investigative Radiology .COPYRGT. J.B. Lippincott Company, pp. 300-304 (Jul.-Aug. 1979).

Bryan, "Bryan Cervical Disc System Single Level Surgical Technique", Spinal Dynamics. 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7. No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. For Opt. Eng., vol. 1894, pp. 312-322 (Jan. 17-19, 1993).

Bucholz, R.D., et al., Intraoperative Ultrasoic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery,Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Irina Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, pp. 137-145 (undated.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image processing, Second Edition, 1987, pp. 52-54.

Gottesfeld Brown et al., "Registration of Planar Film Radiographs with Computer Tomography," Proceedings of MMBIA Jun. '96, pp. 42-51.

Grimson, W.E.L., An Automatic Registration Method for Frameless Stereotaxy, Image Guided Surgery, and enhanced Reality Visualization, IEEE, pp. 430-438 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280. No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13, pp. 193-211 (undated.

Hamadeh et al, "Kinematic Study of Lumbar Spine Using Functional Radiographies and 3D/2D Registration," TIMC UMR 5525—IMAG.

Hamadeh et al., "Automated 3-Dimensional Computed Tomographic and Fluroscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Computer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-524.

Heilbrun et al., "Preliminary experience with Brown-Roberts-Wells (BRW) computerized tomography stereotaxic guidance system," Journal of Neurosurgery, vol. 59. Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, p. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 275-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imaging Technology on Stereotactic Surgery, Proceedings of the Meeting of the American Society for Stereotactic and Functional Neurosurgery, pp. 10-22 (1987).

Kato. A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1. No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed. Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al., "Computer Assisted Driving of a Needle into the Brain," Proceedings of the International Symposium CAR '89, Computer Assisted Radiology, 1989, p. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching 3-D Smooth Surfaces with their 2-D Projections using 3-D Distance Maps," SPIE, vol. 1570, Geometric Methods in Computer Vision, 1991, pp. 322-336.

Lavallee et al., "Matching of Medical Images for Computed and Robot Assisted Surgery," IEEE EMBS, Orlando. 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Application au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96.

Ng, W.S. et al., Robotic Surgery—A First-Hand Experience in Transurethral Resection of the Prostate Surgery, IEEE Eng. in Med. and Biology, pp. 120-125 (Mar. 1993).

Partial European Search Report for Application No. EP 04 00 1428.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds., 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans. Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, H.F., et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, Hans. F., Neuronavigation: A Ten-Year Review, Neurosurgery, pp. 329-341 (undated).

Roberts et al., "A framless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. on Comp-Assisted surgery, MRCAS '95. pp. 185-192 (undated).

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annual Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereotactic System, E2-E6.

The Partial European Search Report mailed Apr. 23, 2008 for European Patent Application No. EP 07 11 1195 has been provided.

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18. No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 8, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128.

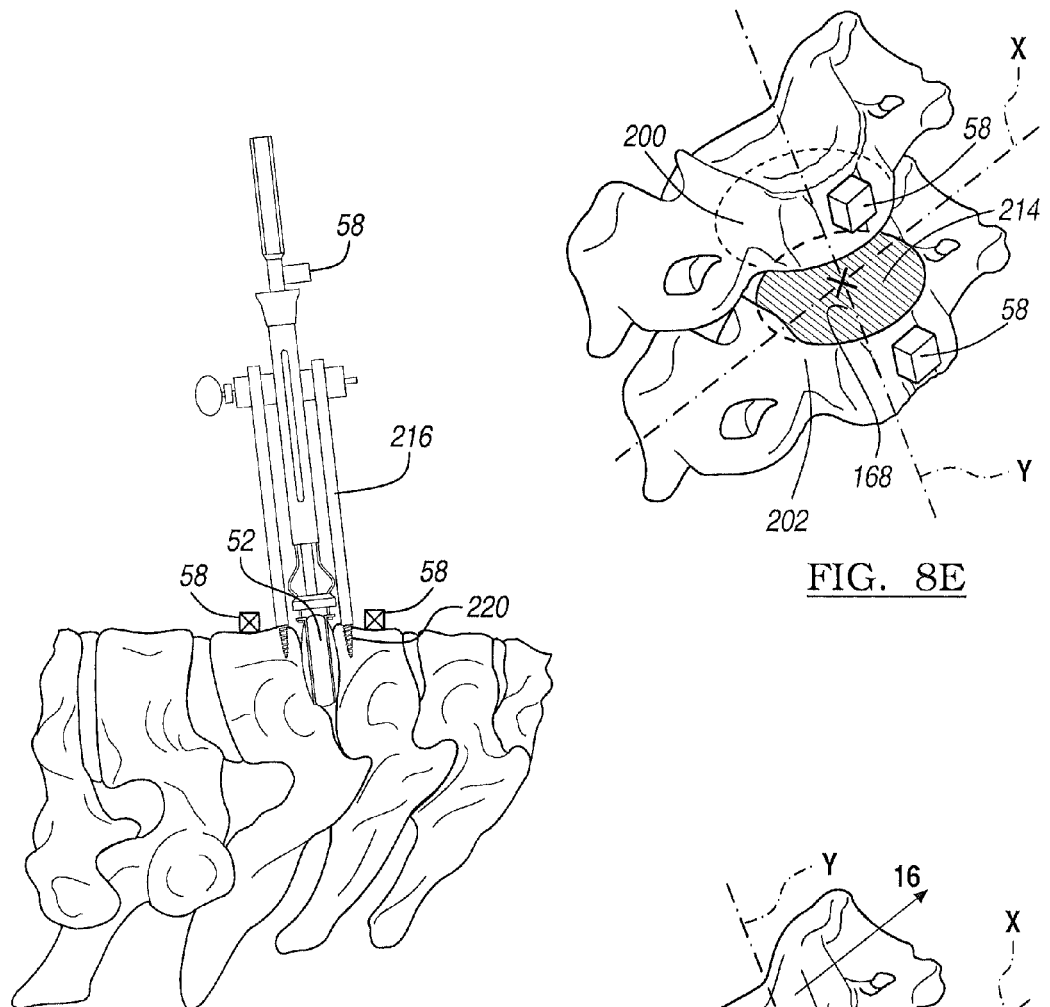
FIG. 8E
FIG. 8F
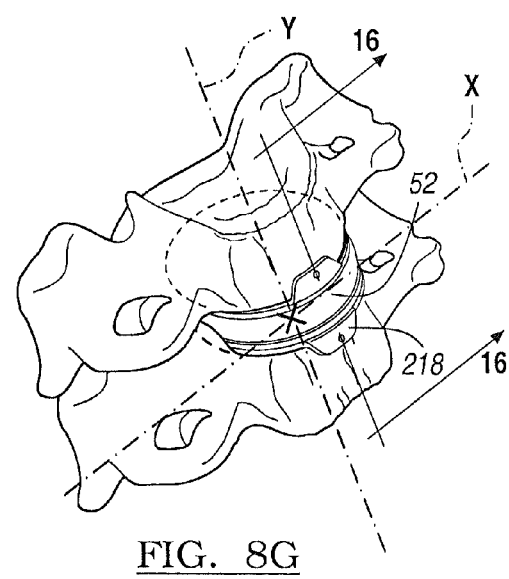
FIG. 8G

METHOD AND APPARATUS FOR PREPLANNING A SURGICAL PROCEDURE

CROSS-REFERENCE TO RELATED APPLICATIONS

This application is a divisional of U.S. patent application Ser. No. 10/794,716, filed on Mar. 5, 2004, which is a continuation-in-part of U.S. patent application Ser. No. 10/423,515 filed on Apr. 25, 2003, which is a continuation-in-part of U.S. patent application Ser. No. 10/354,562 filed on Jan. 30, 2003. The disclosures of the above applications are incorporated herein by reference.

FIELD

The present invention generally relates to planning and performing a selected procedure, and more particularly relates to preoperative planning of a procedure using various techniques and navigation to ensure that the preoperative plan is performed.

BACKGROUND

Image guided medical and surgical procedures utilize patient images obtained prior to or during a medical procedure to guide a physician performing the procedure. Recent advances in imaging technology, especially in imaging technologies that produce highly-detailed, computer-generated two, three and four-dimensional images, such as computed tomography (CT), magnetic resonance imaging (MRI), isocentric C-arm fluoroscopic imaging, fluoroscopes or ultrasounds have increased the interest in image guided medical procedures. During these image guided medical procedures, the area of interest of the patient that has been imaged is displayed on a display. Surgical instruments and/or implants that are used during this medical procedure are tracked and superimposed onto this display to show the location of the surgical instrument relative to the area of interest in the body. Other types of navigation systems operate as an image-less system, where an image of the body is not captured by an imaging device prior to the medical procedure, such as the device disclosed in U.S. patent application Ser. No. 10/687,539, entitled Method And Apparatus For Surgical Navigation Of A Multiple Piece Construct For Implantation, filed Oct. 16, 2003, incorporated herein by reference. With this type of procedure, the system may use a probe to contact certain landmarks in the body, such as landmarks on bone, where the system generates either a two-dimensional or three-dimensional model of the area of interest based upon these contacts. This way, when the surgical instrument or other object is tracked relative to this area, they can be superimposed on this model.

Most types of orthopedic medical procedures are performed using conventional surgical techniques, such as spine, hip, knee, shoulder, a synovial joint, and a facet joint. These techniques generally involve opening the patient in a relatively invasive manner to provide adequate viewing by the surgeon during the medical procedure. These types of procedures, however, generally extend the recovery period for the patient due to the extent of soft tissue and muscular incisions resulting from the medical procedure. Use of image guided technology in orthopedic medical procedures would enable a more minimally invasive type of procedure to be performed to thereby reduce the overall recovery time and cost of the procedure. Use of the image guided procedure may also enable more precise and accurate placement of an implant within the patient.

Once the implant has been surgically positioned within the patient, the patient's surrounding anatomy generally heals over time with the surrounding skeletal and muscular structure regaining a healthy state. However, since the implant is generally implanted when the patient is dysfunctional, this muscular and skeletal adjustment or healing may effect the subsequent range of motion, effectiveness, life expectancy of the implant, performance of the implant, and potentially cause deterioration of surrounding bones, discs, vertebrae, hips, knees, etc., or implants. For example, in a spinal implant, upon the abdominal and back muscles strengthening after the implant procedure, the spine may subsequently align. This alignment may result in the implant or articulation faces of the implant being impinged because of the resultant alignment. This may result in a revision-type surgery that requires the implant to be removed and a subsequent implant being repositioned at the implant site.

The surgical procedures performed during orthopedic medical procedures, including spinal procedures, require the use of various instruments, assemblies and jigs to perform the procedure. Typically, jigs are used to support a single instrument that must be attached to the area of interest when the instrument is being used. Multiple jigs are thus typically required to be attached and removed from the area of interest as the procedure progresses. Use of multiple jigs and instruments, along with attaching and reattaching to the area of interest provides for a tedious and time consuming procedure. Moreover, inherent inaccuracies due to this procedure may provide less than acceptable results.

It is, therefore, desirable to provide a method and apparatus for post-operative adjustment or tuning of an implant, such as a spinal implant using telemetric or minimally invasive techniques. It is also desirable to provide an instrument assembly that may be attached to the implant site, such as a spinal implant site, once during the entire procedure, thereby reducing surgical time, costs, as well as increasing surgical accuracy. It is further desirable to provide a system and apparatus that assist in precise preoperative planning and intraoperative navigation to position a selected implant. For example, it may be desirable to substantially determine a concise size, shape, volume, etc. of a implant prior to performing a procedure to ensure that the procedure will achieve a selected result. In addition, it is desirable to provide a system that will allow for substantially precise placement and performing of a procedure.

SUMMARY

A system may be used for both preoperative planning and navigation during an operative procedure. Preoperative planning may be used to plan and confirm a selected procedure and select an implant for performing the procedure. For example, though not intended to be limiting, a selected disc or nucleus implant may be selected depending upon an image acquired of a patient and various measurements, such as size, shape, volume, location in the spine, (cervical, thoracic, lumbar), range of motion, and others, relating to the disc or nucleus to be replaced. Various other procedures may be performed with the system, such as knee implant selection, a thermal hip stem selection and others. In addition, the system may be used to navigate and perform the procedure to ensure that the selected plan is followed to achieve a result.

According to various embodiments a surgical system for a procedure pertaining to an anatomy is disclosed. The system includes an imaging device to obtain an image of a selected portion of the anatomy. A planning system may also be provided that includes a processor to execute operations relating to the image. The imaging device is operable to image the selected portion of the anatomy prior to the procedure. The processor is operable to determine a selected dimension in the image from the imaging device.

According to various embodiments, a method of performing a procedure to position a prosthesis in a selected portion of an anatomy is disclosed. The method includes acquiring an image of the selected portion of the anatomy and forming a model of the selected portion of the anatomy. A dimension of the model may be measured and a prosthesis may be selected based upon the measurement.

According to various embodiments a method of planning a procedure to implant a prosthetic into a portion of an anatomy includes selecting the portion of the anatomy. A model may be formed of the selected portion of the anatomy that is manipulable with a workstation. A procedure may be selected to be performed on the selected portion of the anatomy and a prosthetic may be selected to be implanted during the procedure.

According to various embodiments a surgical system operable to obtain image data for a procedure pertaining to a selected portion of an anatomy is disclosed. The system includes a planning system having a processor to execute operations relating to the image data. The image data relates to the selected portion of the anatomy prior to the procedure. The planning system is also operable to determine a selected dimension of the selected portion of the anatomy from the image data.

According to various embodiments a method of performing a procedure to position a prosthesis in a selected portion of an anatomy includes acquiring image data of the selected portion of the anatomy. A dimension of the anatomical portion may be measured and a prosthesis may be selected based at least in part of the measurement.

According to various embodiments a surgical system for a procedure pertaining to an anatomy is disclosed. The system may include an imaging device to obtain image data of a selected portion of a spine of the anatomy The system may further include a planning system including a processor to execute operations relating to the image data. The imaging device may generate image data of the selected portion of the anatomy prior to the procedure. The processor may determine a selected dimension in the image data from the imaging device. An implant may be positioned relative to the selected portion of the spine based on the selected dimension.

According to various embodiments a method of performing a procedure to position a prosthesis in a selected portion of a spinal region is disclosed. The method includes acquiring image data of the selected portion of the spinal region and measuring an anatomical dimension of the selected portion of the anatomy with the acquired image data. A prosthesis may be selected based upon the measurement.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 8a-8g illustrate another medical procedure employing the display according to the teachings of the present invention;

DETAILED DESCRIPTION OF VARIOUS EMBODIMENTS

The following description of embodiments is merely exemplary in nature and is in no way intended to limit the invention, its application, or uses. Moreover, while the invention is discussed in detail below in regard to orthopedic/spinal surgical procedures, the present invention may be used with any type of medical procedure, including orthopedic, cardiovascular, neurovascular, soft tissue procedures, or any other medical procedures.

Figure 1:
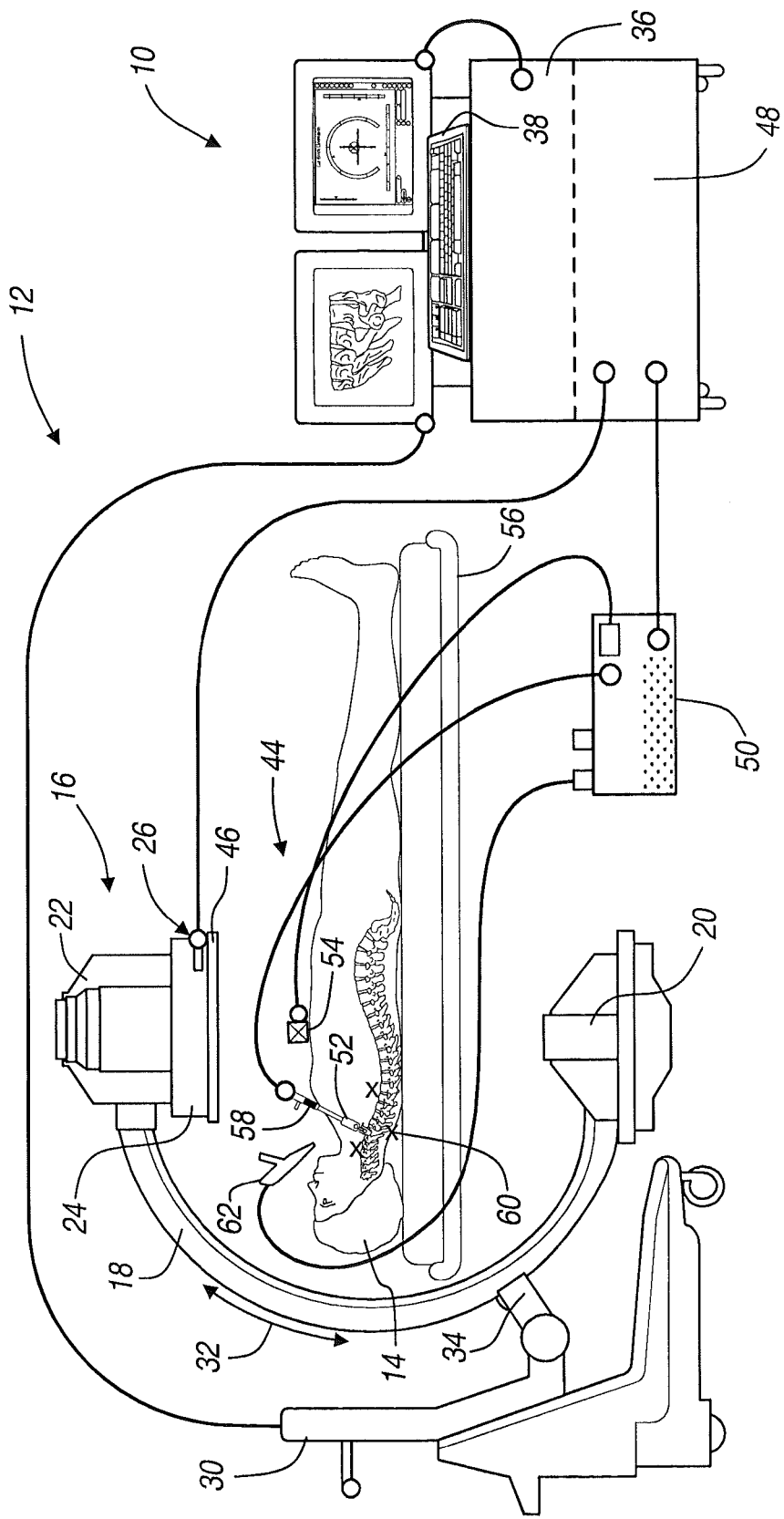
FIG. 1 is a diagram of a navigation system employing a display according to the teachings of the present invention.

FIG. 1 is a diagram illustrating a five or six degree of freedom (5 or 6 DOF) alignment display 10 employed with an image guided navigation system 12 for use in navigating a surgical instrument or implant during a medical procedure. It should also be noted that the display 10 may be used or employed in an image-less based navigation system, further discussed herein. The navigation system 12 may be used to navigate any type of instrument or delivery system, such as a reamer, impactor, cutting block, saw blade, catheter, guide wires, needles, Rongeur instrument, drug delivery systems, cell delivery systems, and nucleus implant delivery systems. The navigation system 12 may also be used to navigate any type of implant including orthopedic implants, spinal implants, cardiovascular implants, neurovascular implants, soft tissue implants, or any other devices implanted in a patient 14. The navigation system 12 may also be used to navigate implants or devices that are formed as an assembly or from multiple components where the location and orientation of each component is dependent upon one another to be effective in its use. For example, during a spinal procedure, the display may be used to track and align a spinal screw with a spinal rod to insure attachment of each device.

The navigation system 12 includes an imaging device 16 that is used to acquire pre-operative or real-time images of the patient 14. The imaging device 16 may be a fluoroscopic imaging device that is incorporated into a C-arm configuration that includes a moveable C-arm 18, an x-ray source 20, an x-ray receiving section 22, an optional calibration and tracking target 24 and optional radiation sensors 26. The optional calibration and tracking target 24 includes calibration markers 28 (see FIGS. 2a-2b), further discussed herein. It will be understood, however, that any appropriate imaging system may be used, including those discussed here.

A controller 30 captures the x-ray images received at the receiving section 22 and stores the images for later use. If a C-arm configuration is used to hold and/or move the imaging system 16, the controller 30 may also control the rotation of the C-arm 18, including the imaging system 16. For example, the C-arm 18 may move in the direction of arrow 32 or rotate about the long axis of the patient 14, allowing anterior or lateral views of the patient 14 to be imaged. Each of these movements involve rotation about a mechanical axis 34 of the C-arm 18. In this example, the long axis of the patient 14 is substantially in line with an axis of motion 34 of the C-arm 18. This enables the C-arm 18 to be moved relative to the patient 14, allowing images of the patient 14 to be taken from multiple directions or about multiple planes. An example of a fluoroscopic x-ray imaging device 16 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm configuration fluoroscopic systems, etc.

In operation, the imaging device 16 generates x-rays from the x-ray source 20 that propagate through the patient 14 and calibration and/or tracking target 24, into the x-ray receiving section 22. The receiving section 22 generates an image representing the intensities of the received x-rays. Typically, the receiving section 22 includes an image intensifier that first converts the x-rays to visible light and a charge coupled device (CCD) video camera that converts the visible light into digital images. Receiving section 22 may also be a digital device that converts x-rays directly to digital images, thus potentially avoiding distortion introduced by first converting to visible light. With this type of digital imaging device, which is generally a flat panel device, the calibration and/or tracking target 24 and the calibration process discussed below may be eliminated. Also, the calibration process may be eliminated for different types of medical procedures. Alternatively, the imaging device 16 may only take a single image with the calibration and tracking target 24 in place. Thereafter, the calibration and tracking target 24 may be removed from the line-of-sight of the imaging device 16.

Two dimensional fluoroscopic images taken by the imaging device 16 are captured and stored in the controller 30. These images are forwarded from the controller 30 to a controller or work station 36 having the display 10 that may either include a single display 10 or a dual display 10 and a user interface 38. The work station 36 provides facilities for displaying on the display 10, saving, digitally manipulating, or printing a hard copy of the received images, as well as the five or six degree of freedom display. The user interface 38, which may be a keyboard, joy stick, mouse, touch pen, touch screen or other suitable device allows a physician or user to provide inputs to control the imaging device 16, via the controller 30, or adjust the display settings, such as safe zones of the display 10, further discussed herein. The work station 36 may also direct the controller 30 to adjust the rotational axis 34 of the C-arm 18 to obtain various two-dimensional images along different planes in order to generate representative two-dimensional and three-dimensional images. When the x-ray source 20 generates the x-rays that propagate to the x-ray receiving section 22, the radiation sensors 26 sense the presence of radiation, which is forwarded to the controller 30, to identify whether or not the imaging device 16 is actively imaging. This information is also transmitted to a coil array controller 48, further discussed herein. Alternatively, a person or physician may manually indicate when the imaging device 16 is actively imaging or this function can be built into the x-ray source 20, x-ray receiving section 22, or the control computer 30.

Figure 2B:
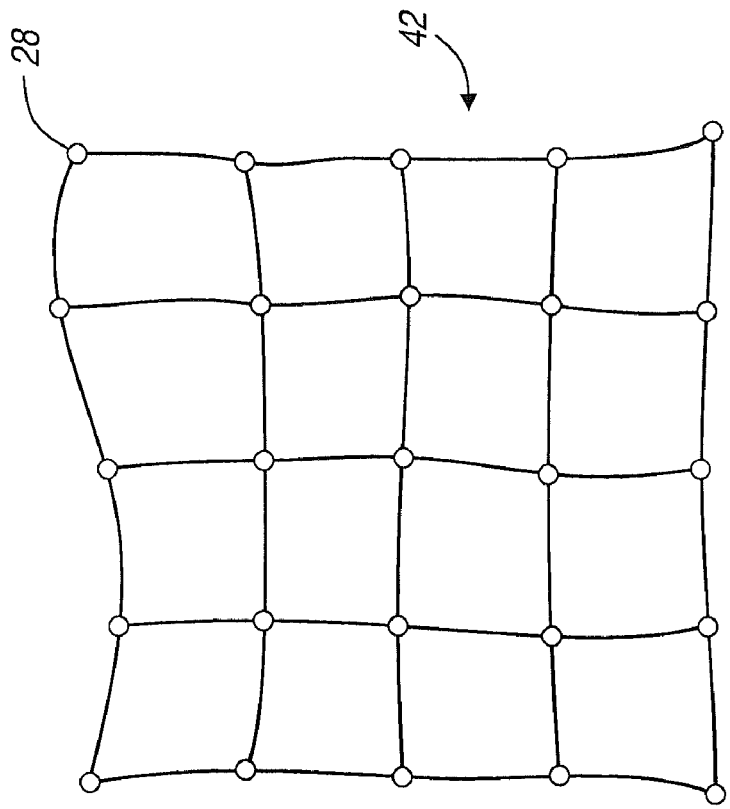
FIGS. 2a and 2b are diagrams representing undistorted and distorted views of a fluoroscopic C-arm imaging device.
Figure 2A:
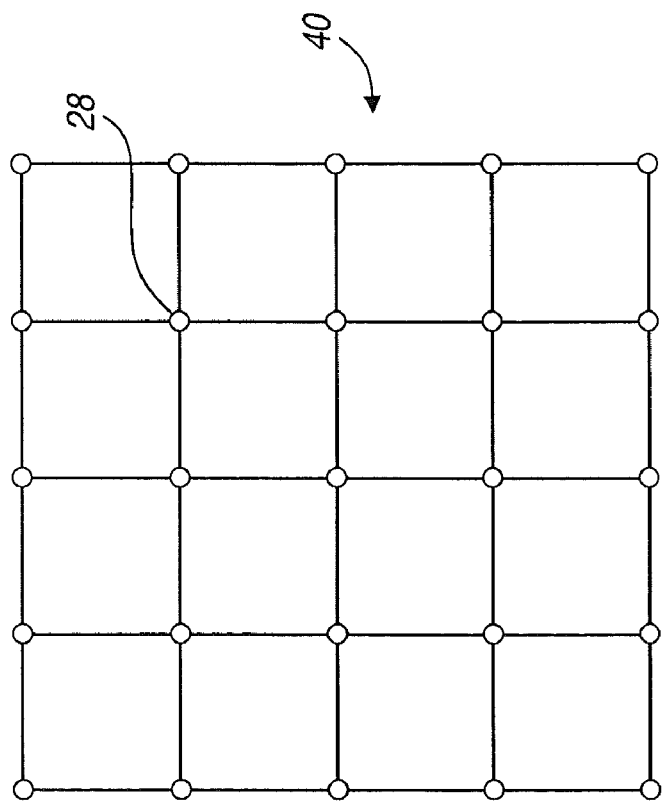

Fluoroscopic imaging devices 16 that do not include a digital receiving section 22 generally require the calibration and/or tracking target 24. This is because the raw images generated by the receiving section 22 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 40 of the checkerboard arranged calibration markers 28. The image taken by the receiving section 22, however, can suffer from distortion, as illustrated by the distorted calibration marker image 42, shown in FIG. 2b.

Intrinsic calibration, which is the process of correcting image distortion in a received image and establishing the projective transformation for that image, involves placing the calibration markers 28 in the path of the x-ray, where the calibration markers 28 are opaque or semi-opaque to the x-rays. The calibration markers 28 are rigidly arranged in pre-determined patterns in one or more planes in the path of the x-rays and are visible in the recorded images. Because the true relative position of the calibration markers 28 in the recorded images are known, the controller 30 or the work station or computer 36 is able to calculate an amount of distortion at each pixel in the image (where a pixel is a single point in the image). Accordingly, the computer or work station 36 can digitally compensate for the distortion in the image and generate a distortion-free or at least a distortion improved image 40 (see FIG. 2a). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the fluoroscopic imaging device 16 is shown in FIG. 1, any other alternative imaging modality may also be used or an image-less based application may also be employed, as further discussed herein. For example, isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), 2D, 3D or 4D ultrasound, intraoperative CT, MRI, or O-arms having single or multi flat panels receivers that move about the ring to acquire fluoroscopic images may also be used to acquire pre-operative or real-time images or image data of the patient 14. Image datasets from hybrid modalities, such as positron emission tomography (PET) combined with CT, or single photon emission computer tomography (SPECT) combined with CT, could also provide functional image data superimposed onto anatomical data to be used to confidently reach target sights within the areas of interest. It should further be noted that the fluoroscopic imaging device 16, as shown in FIG. 1, provides a virtual bi-plane image using a single-head fluoroscope 16 by simply rotating the C-arm 18 about at least two planes, which could be orthogonal planes to generate two-dimensional images that can be converted to three-dimensional volumetric images that can be displayed on the six degree of freedom display 10.

The navigation system 12 further includes an electromagnetic navigation or tracking system 44 that includes a transmitter coil array 46, the coil array controller 48, a navigation probe interface 50, an instrument 52 having an electromagnetic tracker and a dynamic reference frame 54. It should further be noted that the entire tracking system 44 or parts of the tracking system 44 may be incorporated into the imaging device 16, including the work station 36 and radiation sensors 26. Incorporating the tracking system 44 will provide an integrated imaging and tracking system. Any combination of these components may also be incorporated into the imaging system 16, which again can include a fluoroscopic C-arm imaging device or any other appropriate imaging device. Obviously, if an image-less procedure is performed, the navigation and tracking system 44 will be a stand alone unit.

The transmitter coil array 46 is shown attached to the receiving section 22 of the C-arm 18. However, it should be noted that the transmitter coil array 46 may also be positioned at any other location as well, particularly if the imaging device 16 is not employed. For example, the transmitter coil array 46 may be positioned at the x-ray source 20, within the OR table 56 positioned below the patient 14, on siderails associated with the OR table 56, or positioned on the patient 14 in proximity to the region being navigated, such as by the patient's pelvic area. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the instrument 52, further discussed herein. These induced signals from the instrument 52 are delivered to the navigation probe interface 50 and subsequently forwarded to the coil array controller 48. The navigation probe interface 50 provides all the necessary electrical isolation for the navigation system 12. The navigation probe interface 50 also includes amplifiers, filters and buffers required to directly interface with the sensors 58 in instrument 52. Alternatively, the instrument 52 may employ a wireless communications channel as opposed to being coupled directly to the navigation probe interface 50.

The instrument 52 is equipped with at least one, and may include multiple localization sensors 58. In this regard, the instrument 52 may include an orthogonal pair coil sensor 58 or a tri-axial coil sensor 58 or multiple single coil sensors 58 positioned about the instrument 52. Here again, the instrument 52 may be any type of medical instrument or implant. For example, the instrument may be a catheter that can be used to deploy a medical lead, be used for tissue ablation, or be used to deliver a pharmaceutical agent. The instrument 52 may also be an orthopedic instrument, used for an orthopedic procedure, such as reamers, impactors, cutting blocks, saw blades, drills, drill guides, distracters, awls, taps, probes, screw drivers, etc. The instrument 52 may also be any type of neurovascular instrument, cardiovascular instrument, soft tissue instrument, etc. Finally, the instrument 52 may be an implant that is tracked, as well as any other type of device positioned and located within the patient 14. These implants can include orthopedic implants, neurovascular implants, cardiovascular implants, soft tissue implants, spinal implants, nucleus implants, cranial implants, or any other devices that are implanted into the patient 14. Particularly, implants that are formed from multiple components where the location and orientation of each component is dependent upon the location and orientation of the other component, such that each of these components can be tracked or navigated by the navigation and tracking system 44 to be displayed on the six degree of freedom display 10.

In an alternate embodiment, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization or tracking may also be used with other types of navigation systems, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. These types of localization systems include conductive, active optical, passive optical, ultrasound, sonic, electromagnetic, etc. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54 is a small magnetic field detector or any other type of detector/transmitter that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as the patient's spinal region, as shown in FIG. 1 or on any other region of the patient. The dynamic reference frame 54 can be affixed to the patient's skin, by way of a stick-on adhesive patch. The dynamic reference frame 54 may also be removably attachable to fiducial markers 60 also positioned on the patient's body and further discussed herein.

Alternatively, the dynamic reference frame 54 may be internally attached, for example, to the spine or vertebrae of the patient using bone screws that are attached directly to the bone. This provides increased accuracy since this will track any motion of the bone. Moreover, multiple dynamic reference frames 54 may also be employed to track the position of two bones relative to a joint. For example, one dynamic reference frame 54 may be attached to a first vertebra, while a second dynamic reference frame 54 may be attached to a second vertebra. In this way, motion of the spine or vertebrae may be detected by the dual dynamic reference frames 54. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference.

The dynamic reference frame 54 may be affixed or connected to the vertebrae in any appropriate manner. For example a pin or rod may interconnect the dynamic reference frame 54 and the vertebrae. Other mechanisms may be provided to reduce rotation, such as teeth or barbs that extend from the rod and further engage the vertebrae that reduce rotation of the rod and the dynamic reference frame 54. Various exemplary systems are disclosed in U.S. Pat. Nos. 6,226,548 and 6,203,543, each incorporated herein by reference. This may allow the dynamic reference frame 54 to be attached to the vertebrae substantially percutaneously.

Also the workstation 38, or any appropriate portion of the system, may provide for a check of the placement of the dynamic reference frame in the image space. For example, unintended rotational or other movement may occur. The system, including software, may be used to determine that at least one of the dynamic reference frames 54 have moved. During a cycle of the software, or any other appropriate time, the system may check to ensure that the dynamic reference frame 54 is in a selected location. If it is not the user may re-register the patient 14. Alternatively a second dynamic reference frame, of known movement and relative location to the first dynamic reference frame, may be used to re-register or correlate the inadvertent movement of the first dynamic reference frame.

Regardless, the system may be able to determine that the dynamic reference frame is in a location other than a selected or known location. For example, the system may determine that the dynamic reference frame may have moved an amount greater than expected or a direction, such as rotation about its axis of fixation to the patient, other than one expected. The system, including the workstation 38, may then provide an alert, such as an audible or visual alert, to a user that the unexpected movement has occurred. The user can then re-register the patient 14 or an autonomous re-registration may be completed with the workstation 38.

Briefly, the navigation system 12 operates as follows. The navigation system 12 creates a translation map between all points in the radiological image generated from the imaging device 16 and the corresponding points in the patient's anatomy in patient space. After this map is established, whenever a tracked instrument 52 is used, the work station 36 in combination with the coil array controller 48 and the controller 30 uses the translation map to identify the corresponding point on the pre-acquired image, which is displayed on display 10. This identification is known as navigation or localization. An icon representing the localized point or instrument is shown on the display 10, along with five or six degrees of freedom indicia.

In addition, the dynamic reference frame 54 may include coils that are tracked with an electromagnetic (EM) tracking system. In such a system the dynamic reference frame may include a plurality of coils placed in a known geometry and distance from each other. Then, during a use of the dynamic reference frame 54 the system may determine whether interference is obscuring a true measurement of the dynamic reference frame 54. For example, a metal object may create eddy current induced in the EM coils. Thus the system may both determine a location of the dynamic reference frame 54 and the relative location of each of the plurality of EM coils in the dynamic reference frame 54. The system can then compare the relative sensed location and/or placement of the EM coils to the known geometry of the coils and select the most appropriate coil that is providing the signal. For example, if three coil are placed at a selected angle, such as 120 degrees, and a known distance, such as 2 mm, from the others this known information can be used to determine which coil is the least interfered. That is the coil that sensed most precisely relative to the other known coils is the coil that is more precise in that field.

To enable navigation, the navigation system 12 will detect both the position of the patient's anatomy 14 and the position of the surgical instrument 52. Knowing the location of these two items allows the navigation system 12 to compute and display the position of the instrument 52 in relation to the patient 14. The tracking system 44 is employed to track the instrument 52 and the anatomy simultaneously. While the display 10 is configured to show the instrument with six degree of freedom accuracy.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the sensor 58 location. The dynamic reference frame 54 is fixed to the patient 14 to identify the location of the patient 14 in the navigation field. The electromagnetic tracking system 44 continuously recomputes the relative position of the dynamic reference frame 54 and the instrument 52 during localization and relates this spatial information to patient registration data to enable image guidance of the instrument 52 within the patient 14.

Patient registration is the process of determining how to correlate the position of the instrument 52 on the patient 14 to the position on the diagnostic, pre-acquired, or real-time images. To register the patient 14, the physician or user will select and store particular points from the pre-acquired images and then touch the corresponding points on the patient's anatomy with a pointer probe 62. The navigation system 12 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks 60 that can be easily identified in the image data. Other types of registration may be point registration, contour surface registration, isocentric registration, automatic registration, and any other appropriate system or method of registering a patient space to an image space. The system 12, such as the system disclosed in U.S. patent application Ser. No. 10/644,680, entitled Method and Apparatus for Performing 2D to 3D Registration, filed Aug. 20, 2003, incorporated herein by reference, may also perform 2D to 3D registration by utilizing the acquired 2D images to register 3D volume images by use of contour algorithms, point algorithms, normalized mutual information, pattern intensity, or density comparison algorithms, as is known in the art.

In order to maintain registration accuracy, the navigation system 12 continuously tracks the position of the patient 14 during registration and navigation. This is necessary because the patient 14, dynamic reference frame 54, and transmitter coil array 46 may all move during the procedure, even when this movement is not desired. Therefore, if the navigation system 12 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

It should also be understood that localization and registration data may be specific to multiple targets. For example, should a spinal procedure be conducted, each vertebra may be independently tracked and the corresponding image registered to each vertebra. In other words, each vertebra would have its own translation map between all points in the radiological image and the corresponding points in the patient's anatomy in patient space in order to provide a coordinate system for each vertebra being tracked. The tracking system 44 would track any motion in each vertebra by use of a tracking sensor 58 associated with each vertebra. In this way, dual displays 10 may be utilized, further discussed herein, where each display tracks a corresponding vertebra using its corresponding translation map and a surgical implant or instrument 52 may be registered to each vertebra and displayed on the display 10 further assisting an alignment of an implant relative to two articulating or movable bones. Moreover, each separate display in the dual display 10 may superimpose the other vertebra so that it is positioned adjacent to the tracked vertebra thereby adding a further level of information on the six degree of freedom display 10.

As an alternative to using the imaging system 16, in combination with the navigation and tracking system 44, the five or six degree of freedom alignment display 10 can be used in an imageless manner without the imaging system 16. In this regard, the navigation and tracking system 44 may only be employed and the probe 62 may be used to contact or engage various landmarks on the patient. These landmarks can be bony landmarks on the patient, such that upon contacting a number of landmarks for each bone, the workstation 36 can generate a three-dimensional model of the bones. This model is generated based upon the contacts and/or use of atlas maps. The workstation 36 may also generate a center axis of rotation for the joint or planes, based upon the probe contacts. Alternatively, the tracking sensor 58 may be placed on the patient's anatomy and the anatomy moved and correspondingly tracked by the tracking system 44. For example, placing a tracking sensor 58 on the femur and fixing the pelvis in place of a patient and rotating the leg while it is tracked with the tracking system 44 enables the work station 36 to generate a center of axis of the hip joint by use of kinematics and motion analysis algorithms, as is known in the art. If the pelvis is not fixed, another tracking sensor 58 may be placed on the pelvis to identify the center of axis of the hip joint. If a tracking sensor 58 is placed on the femur and a tracking sensor 58 is placed on the tibia, upon moving this portion of the anatomy, a center of axis of the knee joint may be identified. Likewise, by placing a separate tracking sensor 58 on two adjacent vertebra and articulating the spine, the center of axis of the spinal region can also be identified. In this way, a target and/or model based on the center of the particular joint may be designated and identified on the six degree of freedom display 10. Movement of the instrument or implant 52 may then be tracked in relation to this target and/or model to properly align the instrument or implant 52 relative to the target and/or model.

Figure 3A:
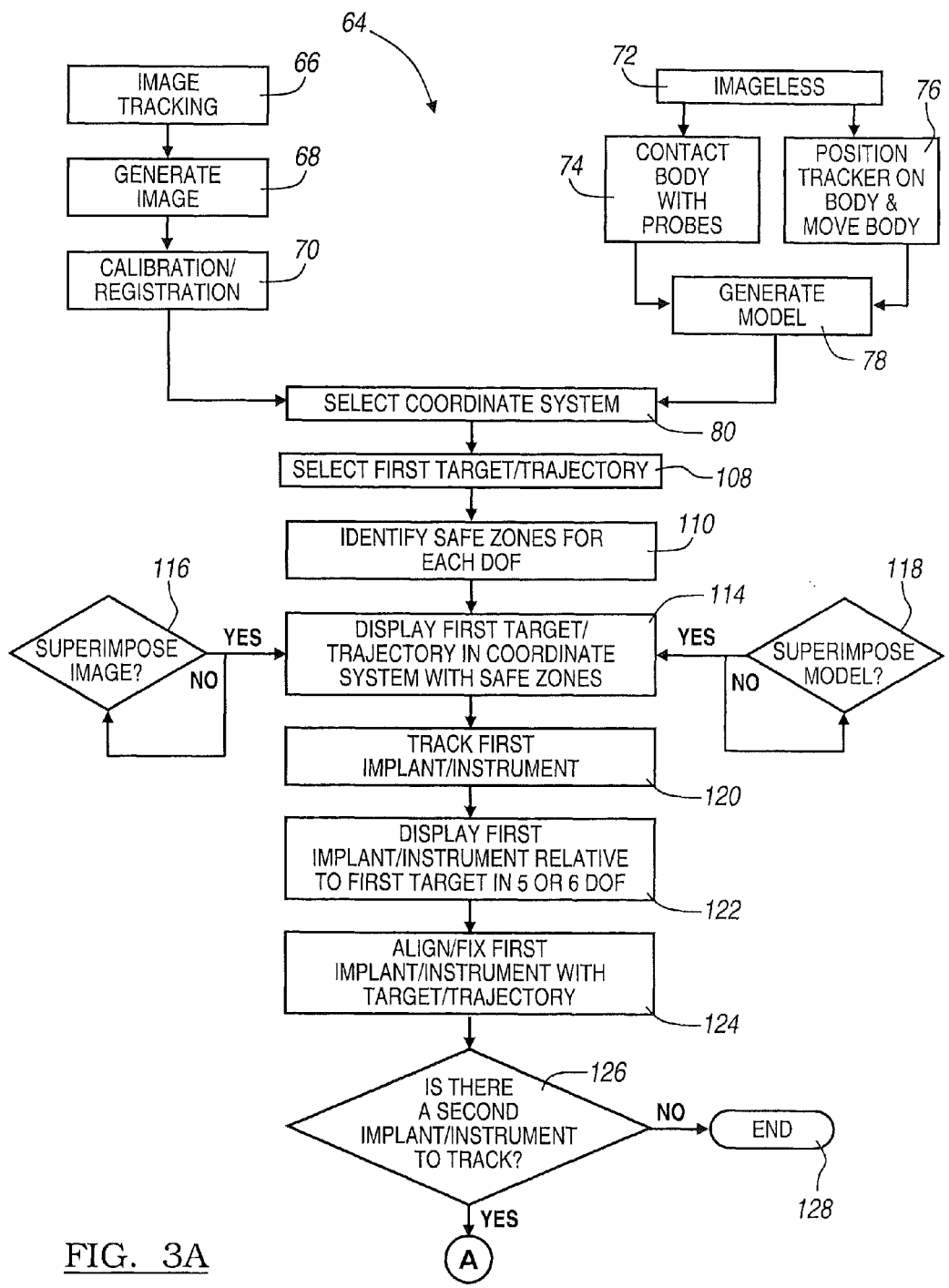
FIGS. 3a and 3b is a logic block diagram illustrating a method for employing the display according to the teachings of the present invention.
Figure 3B:
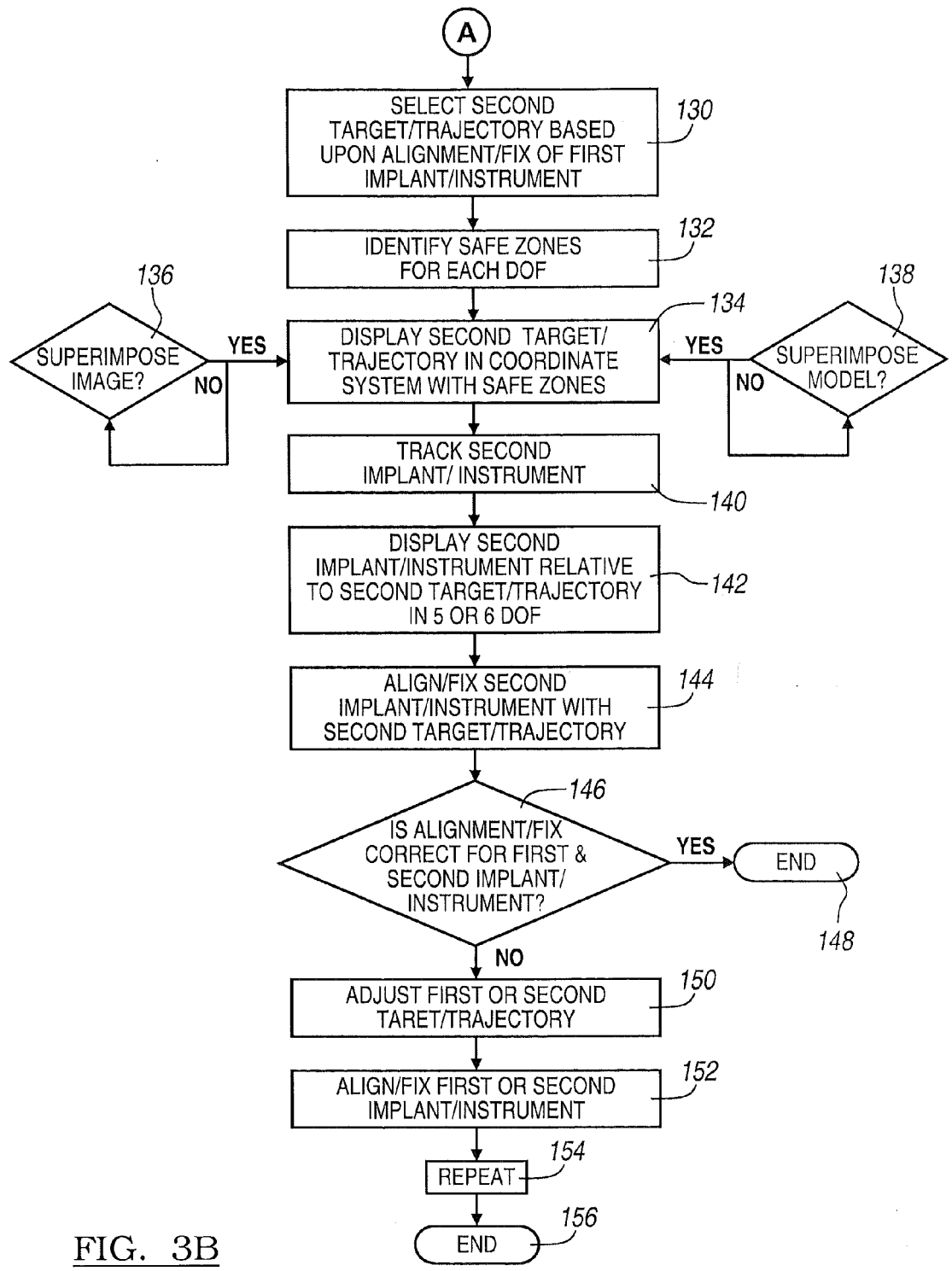

Turning to FIGS. 3a and 3b, the method of employing the six degree of freedom display 10 is described in further detail. The method 64 begins by determining whether an image based medical procedure will be employed or an image-less medical procedure will be employed. If the image based procedure is being employed, the method proceeds along the first branch. In this regard, when an image based procedure will be utilized, the method begins at block 66 identifying the image tracking procedure. From block 66, the method proceeds to block 68 where images are generated by the imaging system 16. This imaging is performed at the area of interest of the patient 14 by any type of imaging device as previously discussed. Once images have been generated at block 68, the method proceeds to block 70 where calibration and registration is performed. In block 70, calibration of the imaging device 16 takes place using the calibration targets 28. Additionally, registration of the pre-acquired images from block 68 are registered to the patient space of the medical procedure utilizing the fiducial markers 60 and probe 62 as previously discussed. This registration registers the current patient space with the pre-acquired image, so that the instrument 52 or other devices may be tracked during the medical procedure and accurately superimposed over the pre-acquired images generated from the imaging device 16.

If an image-less medical procedure is selected, the method begins at block 72 identifying that an image-less based medical procedure will be performed. This method proceeds to either block 74 identifying a first way to generate image-less models or block 76 identifying a second way to generate image-less models. At block 74, the probe 62 is used to contact the body at various anatomical landmarks in the area of interest, such as a bone. For example, by touching the probe 62 to the pelvis, knee, ankle, and spine, articulation planes can be defined using known algorithms and the center of each joint may also be defined. An example of this type of modeling is set forth in U.S. Pat. No. 5,682,886, which is hereby incorporated by reference. Alternatively, multiple anatomical landmarks can be contacted with the probe 62 to generate a 3-D model with the more points contacted, the more accurate the model depicted.

Secondly, to generate a model at block 76, a tracking device is placed on the body and the body rotated about the joint. When this is done, the plane of rotation and joint center can be identified using known kinematic and/or motion analysis algorithms or using atlas maps or tables, as is known in the art. Once the area of interest has been probed, via block 74 or block 76, a model is generated at block 78. This model can be a 3-D surface rendered model, a 2-D model identifying articulating planes or a 3-D model identifying articulating planes and rotation, as well as the center of the joints. This enables the display 10 to use the joint centers or articulating planes as the target or trajectory, further discussed herein.

With each of the procedures 74 or 76, the procedure may be initially based on the use of atlas information or a 3-D model that is morphed, to be a patient specific model. In this regard, should the femur be the area of interest, an accurate representation of an ordinary femur may be selected from an atlas map, thereby providing an initial 2-D or 3-D model representing a typical anatomical femur. As with block 74, upon contacting numerous areas on the actual femur with the probe 62, the atlas model may be morphed into a patient specific 3-D model, with the more points contacted, the more accurate the morphed model. Patient specific information may also be acquired using an ultrasound probe to again identify the shape of the patient's natural femur in order to morph the atlas model. A fluoroscopic image of the region may also be used to morph the patient's femur with the atlas model to provide a patient specific morphed model. Proceeding under block 76 and assuming that the area of interest is the hip joint, an atlas model of the femur and pelvis may be the initial starting point. Upon rotating and moving the femur relative to the pelvis, a patient specific morphed model may be created to generate accurate joint centers and axes of motion again using known kinematics and/or motion analysis algorithms Once the image data is calibrated and registered at block 70 or the model is generated at block 78, the method proceeds to block 80. At block 80, the specific type of coordinate system is selected, which will be displayed by indicia on the six degree of freedom display 10. The coordinate systems can be a Cartesian coordinate system, a spherical coordinate system, or a polar coordinate system. By way of example, the Cartesian coordinate system will be selected. The Cartesian coordinate system will include the X, Y, and Z axes, and X rotation, Y rotation, and Z rotation about its respective axes.

Figure 5:
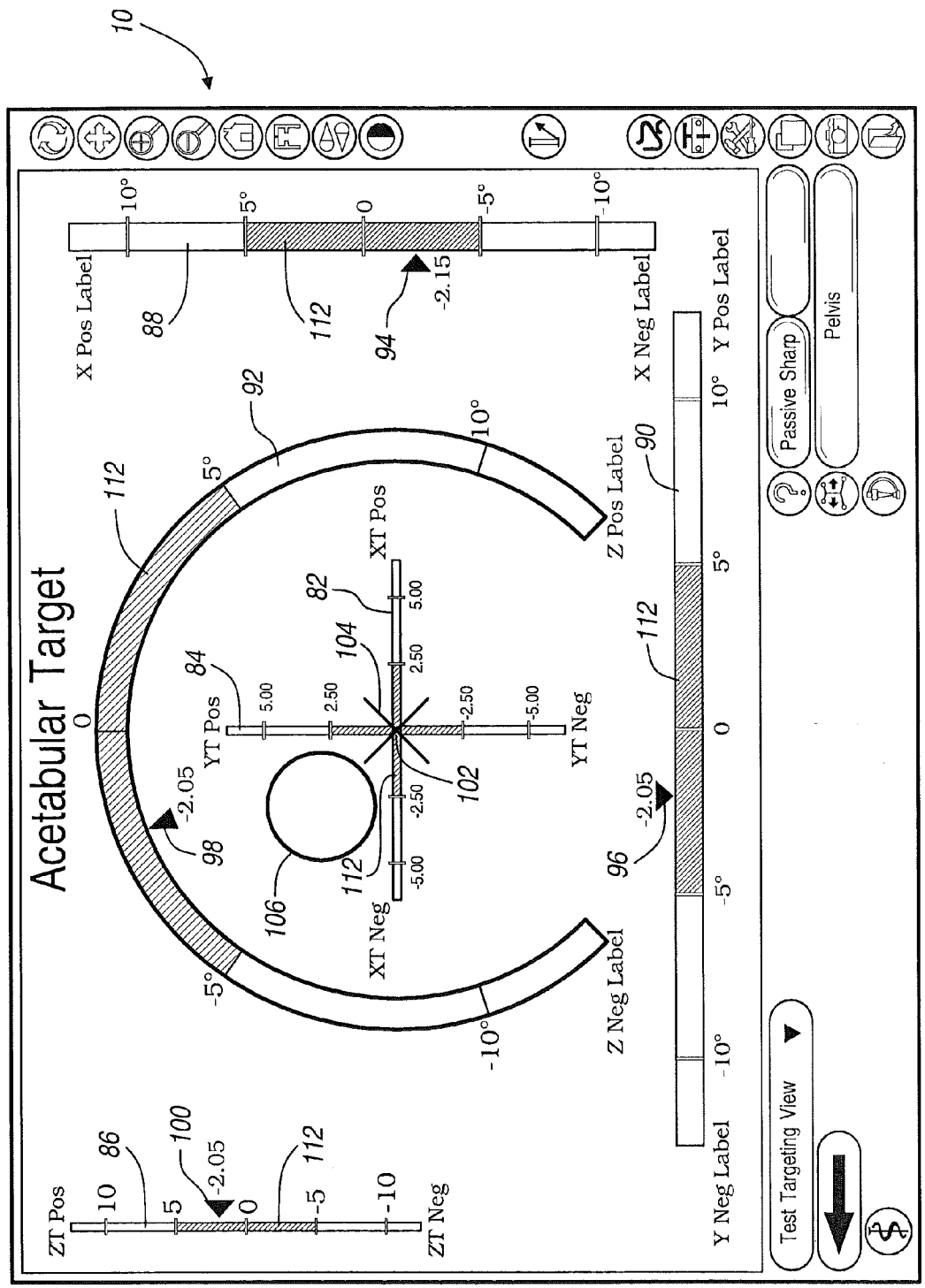
FIG. 5 is a figure of the display according to the teachings of the present invention.

With reference to FIG. 5, the six degree of freedom display 10 is shown in further detail employing the Cartesian coordinate system. In this regard, the X axis 82 and the Y axis 84 are shown positioned on the display 10. The Z axis 86 extends out from the display 10 and is shown in the upper left corner. Rotation about the X axis is shown by bar graph 88 to the right of the display 10 and rotation about the Y axis is shown by bar graph 90 positioned at the bottom of the display 10. Rotation about the Z axis is shown with the arcuate bar graph 92 oriented about the X and Y axes 82 and 84. Each axis, as well as the rotation axes identified by the bar graphs may be color coded to identify safe zones or regions for the item being tracked or navigated. In this regard, the safe zones can be defined as ranges around the planned trajectory path or target where the safe zones are determined by manufactured determined parameters, user determined parameters or patient specific parameter, further discussed herein.

Arrow indicator 94 identifies the degree of rotation about the X axis 82. Arrow indicator 96 shows the amount of rotation about the Y axis 84. Arrow 98 identifies the rotation about the Z axis, while arrow 100 identifies the depth being tracked along the Z axis 86. The origin 102 may be set to be the desired target position or trajectory path. The crosshairs 104 represents the tip of the instrument 52 being tracked, while the circle 106 represents the hind area of the instrument 52 being tracked. With the understanding that the instrument 52 can be any type of medical device or implant. Also, if five degree of freedom information is provided, one of the indicia 82, 84, 86, 88, 90, and 92 will be removed.

Once the coordinate system is selected at block 80, the method proceeds to block 108 where the target or trajectory is selected. The target or trajectory selected at block 108 is typically positioned at the origin 102 on the display 10. In this way, the object being tracked or aligned may be tracked and aligned about the origin 102. Alternatively, the target may be identified at any coordinate within the display 10 or multiple targets may also be identified within the single display 10. An indicia of the target may also be positioned on the display 10. The target is selected based upon the desired area to position the instrument 52 and can be selected from the pre-acquired images or from the 3-D model. Once selected, this target is correlated to the display 10 and generally positioned at the origin 102.

Once the target/trajectory is selected at block 108, such as the origin 102, the method proceeds to block 110 where the safe zones are identified for each degree of freedom. Referring again to FIG. 5, the safe zones 112 are identified for each degree of freedom by color coding. For example, the safe zone 112 for the X axis is between −2.5 and +2.5. The safe zone 112 for rotation about the X axis is between −50 and +50 of rotation about the X axis. The user can simply guide the instrument 52 using the cross hairs 104 and circle 106 to align the instrument 52 within these designated safe zones 112. Again, these safe zones 112 may be determined by manufacture specifications, such as tolerance range of the instruments or positions for implants. The safe zones 112 may also be determined based on the patient, the surgeon conducting the procedure, or any other factors to assist a surgeon in navigating the instrument 52 through the patient 14. These safe zones 112 may also be identified via an audible signal or tone or a varying tone. The safe zones 112 may also be identified by any other convenient manner to be set out on the display 10.

Figure 6:
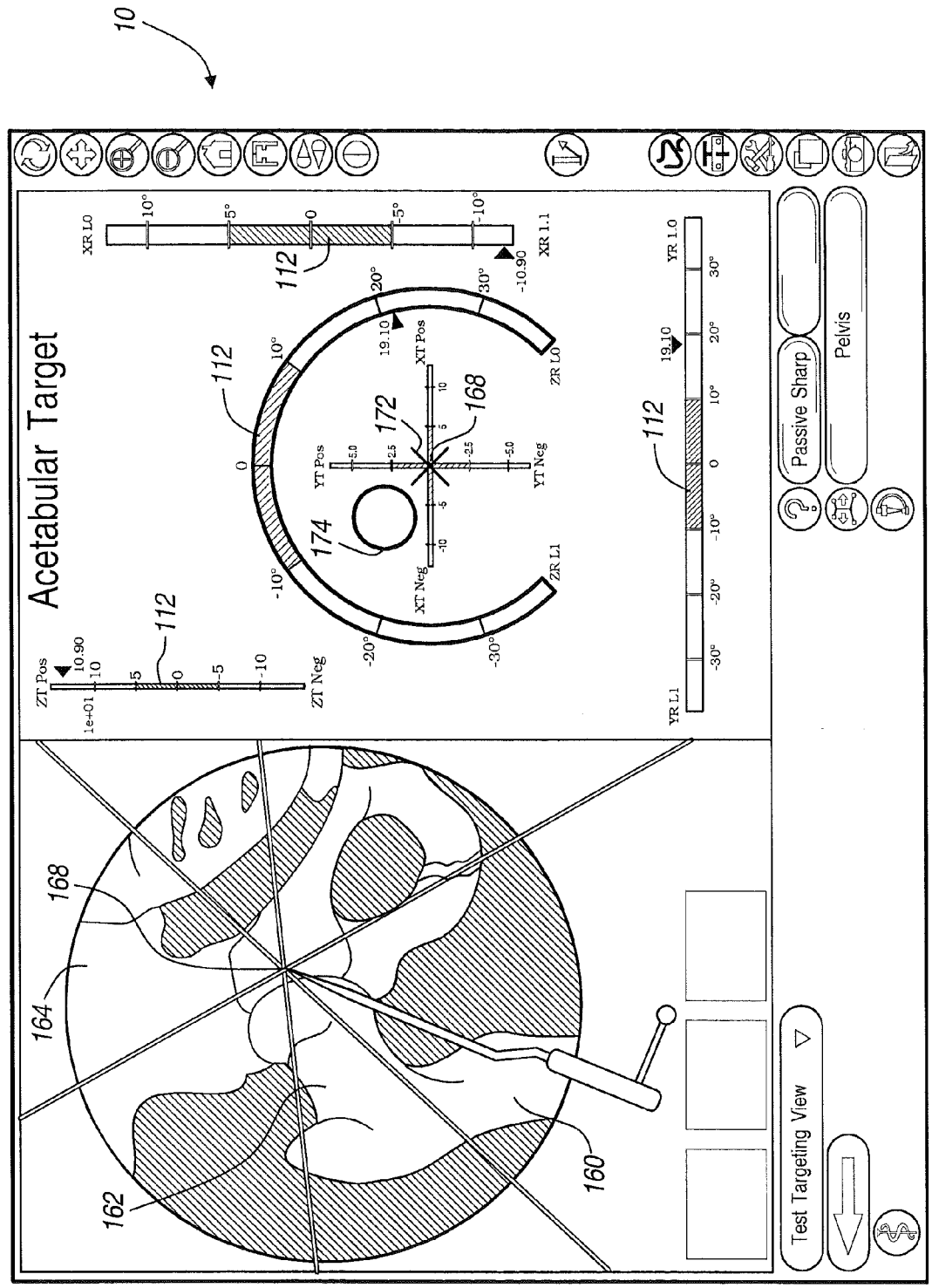
FIG. 6 is a split screen view of the display according to the teachings of the present invention.

Once the safe zones 112 are identified for each degree of freedom in block 110, the method proceeds to block 114 where the target trajectory in the selected coordinate system is displayed with the safe zones 112, as shown in FIG. 5. At block 116, if an image based method is being conducted, a decision whether to superimpose the image over the target/trajectory is made. Alternatively, the image may be placed adjacent to the target trajectory display, as is shown in FIG. 6, and further discussed herein. Should the image-less based medical procedure be conducted, at block 118, a determination is made whether to superimpose the model that was generated at block 78. Here again, this model may be superimposed over the target/trajectory display on display 10 or may be positioned adjacent to the target/trajectory display in a split screen or on a separate display.

Once the target/trajectory 102 is displayed along with the safe zones 112 in the proper coordinate system, as shown in FIG. 5, the method proceeds to block 120 where the first implant/instrument 52 is tracked with the navigation system 44. With the implant/instrument 52 being tracked at block 120, the method proceeds to block 122 wherein indicia representing the implant/instrument 52 is displayed on the display 10, with either five or six degrees of freedom information. Here again, referring to FIG. 5, the indicia representing the implant/instrument 52 is the crosshairs 104 and the circle 106 designating the tip and hind, respectively. The tip 104 and hind 106 is represented in relation to the target/trajectory path 102 in six degrees of freedom. This six degrees of freedom include the X and Y locations, as well as the depth Z of the implant/instrument 52 displayed. In addition, the rotation about each of the axes is also provided. This rotation can be helpful in many applications, including orthopedic, where rotation specific components need to be positioned relative to one another. For example, in a spinal application, alignment of a pedicle screw in relation to a spinal rod or spinal implant, would require information regarding the rotation of the screw relative to the rod or implant. In cardiac procedures, this may be useful where ablation is necessary on a certain side of an artery and the ablation electrode is only positioned on one side of the catheter. In this situation, rotation of the catheter relative to the target in the artery is critical. In a neuro procedure, a biopsy needle may only have a biopsy port positioned upon one portion of the circumference of the needle, thereby requiring the rotation of the biopsy needle to be known in order to provide the proper capture of the relevant biopsy sample. Without this display, this information would not be available.

With the indicia of the implant/instrument 52 being displayed, the implant/instrument 52 is aligned or fixed with the target/trajectory 102 at block 124. In this regard, the tip 104 and the hind 106 are aligned and fixed relative to the target/trajectory 102 at the origin and the rotational orientation is also aligned to the desired position. Again, the target/trajectory 102 may not be positioned at the origin and can be positioned anywhere within the coordinate system if desired. As shown in FIG. 5, the tip 104 of the implant/instrument 52 is shown aligned with the target 102, while the hind 106 is slightly offset from the target/trajectory 102. Once the implant/instrument 52 is aligned and fixed relative to the target/trajectory 102, the method proceeds to block 126.

At block 126, a determination is made as to whether there is a second implant/instrument 52 to be tracked. If there is not a second implant/instrument 52 to be tracked, the method ends at block 128. Should there be a second implant/instrument 52 to track, such as a corresponding implant component that articulates with the first implant, the method proceeds to block 130. At block 130, a second target/trajectory 102 is selected, which is based upon the alignment or fixation of the first implant/instrument 52 relative to the first target/trajectory 102. In this regard, if the surgeon is not able to position the first implant/instrument 52 at the desired target/trajectory 102, this offset from the target/trajectory 102 may affect the second implant, which possibly articulates or mates with the first implant. If this is the case, the second target/trajectory 102 will need to take into consideration this offset in order to provide proper articulation and alignment of the first implant component with the second implant component.

With minimally invasive types of procedures, the implant may also have numerous components with each component articulating or mating with another component, thereby requiring tracking of each component as it is implanted during the minimally invasive procedure. This second target/trajectory 102 may be displayed on a separate display 10 (see FIG. 1), positioned via a split screen of a single display 10 or may be superimposed upon the existing display that displays the first target 102 and implant position. In this way, orientation and placement of both the first and second implants, which are dependent upon one another can be shown in the display 10 providing the surgeon the opportunity to adjust either position of either implant intraoperatively before the implants are permanently affixed to the patient 14. These types of implants include knee implants, hip implants, shoulder implants, spinal implants, or any other type of implant, which has a bearing surface and an articulating surface or any type of implant having multiple mating and connecting components.

Once the second target/trajectory 102 has been selected at block 130, the method proceeds to block 132. At block 132, the safe zones 112 for each degree of freedom is selected for the second implant/instrument 52 similar to the way the first set of safe zones 112 were selected for the first implant/instrument 52. Once the second safe zones 112 are selected, the method proceeds to block 134. At block 134, the display 10 displays the second target/trajectory 102 in the same coordinate system with the second safe zones 112. Here again, at block 136, if it is an image based medical procedure, the pre-acquired image may be superimposed on to the target/trajectory 102. Alternatively, this image can be positioned adjacent the target screen in a split screen configuration (see FIGS. 6 and 7). If the method is proceeding as an image-less type medical procedure, at block 138, decision is made whether to superimpose the generated model from block 78. Once the target/trajectory 102 is in the proper coordinate system with the safe zone 112 are displayed at display 10, the surgical implant/instrument 52 is tracked at block 140. Here again, the second implant/instrument 52 can be tracked on a separate display 10 or be tracked on the same display as the first implant/instrument 52.

Alternatively, separate displays 10 may be used where information is linked between the displays showing the second implant/instrument 52 in relation to the first implant/instrument 52. With the second implant/instrument 52 being tracked at block 140, the second implant/instrument 52 is displayed in relation to the second target/trajectory 102 in five or six degrees of freedom at block 142. Again, this may be a separate display 10, a split screen display 10 with both the first target/trajectory 102 and the second target/trajectory 102 or the same display 10 displaying both targets/trajectories 102. While the second implant/instrument 52 is being displayed, the second implant/instrument 52 is aligned and fixed at the second target/trajectory 102 at block 144. Once the second implant/instrument 52 is fixed at block 144, the method proceeds to block 146.

At block 146, a determination is made whether the alignment or fixation of the first and second implants/instruments 52 are correct. In this regard, with two separate displays 10 linked or with a single display 10, showing both targets/trajectories 102, a surgeon can determine whether each implant/instrument 52 is within its desired safe zones 112 and, therefore, optimally positioned for proper articulation. Here again, these safe zones 112 may be color coded for the different safe zones provided. If both implants are positioned and fixed at the proper targets, the method ends at block 148. If one or both of the implants are not properly positioned, adjustment of the first or second target/trajectory 102 is performed at block 150. Once either or both targets are adjusted, realignment of the first and/or second implants/instruments 52 are performed at block 152. Here again, since multiple component implants are dependent upon one another with respect to their position and orientation, alignment and adjustments of the targets/trajectories 102 may be performed several times until the optimum placement for each is performed at repeat block 154. Thereafter, the method terminates at end block 156.

While the above-identified procedure is discussed in relation to an orthopedic medical procedure in which an implant having multiple implant components is implanted within a patient using the six degree of freedom display 10, it should be noted that the six degree of freedom display 10 may be used to track other medical devices as well. For example, as was briefly discussed, an ablation catheter generally has an electrode positioned only on one angular portion of its circumference. Likewise, the wall of an artery typically has a larger plaque build-up on one side. Therefore, it is desirable to align that ablation electrode with the proper side of the artery wall during the procedure. With the six degree of freedom display 10, the surgeon can easily identify the location, depth and angular rotation of the catheter relative to the artery wall. Other types of procedures may require the medical instrument or probe to be properly oriented and located within the patient, such as identifying and tracking tumors, soft tissue, etc. By knowing and displaying the six degree of freedom movement of the medical device on the display 10, the medical procedure is optimized.

It should also be pointed out that the method discussed above requires that the implant/instrument 52 have a tracking sensor associated therewith in order to identify the location of the tracked device in six degrees of freedom and display it on the display 10. The tracking sensors may be attached directly to implants, attached to the instruments that engage the implants or attach to members extending out from the implants. These tracking sensors again may be electromagnetic tracking sensors, optical tracking sensors, acoustic tracking sensors, etc. Examples of various targets, which may or may not be superimposed on the display again include orthopedic targets, spinal targets, cardiovascular targets, neurovascular targets, soft tissue targets, etc. Specific examples include again the location of the plaque on a wall of an artery, the center of an articulating joint being replaced, the center of the implant placement, etc. By displaying two targets, either on separate displays or on the same display, the surgeon can dynamically plan and trial implant placements by moving one component of the implant to see where the other articulating component of the implant should be positioned. In this way, the surgeon can trial the implant confirming its placement and orientation, via the display 10 before the implant is permanently affixed to the patient 14.

In a spinal procedure, two adjacent vertebra bodies can be tracked and displayed on two separate displays. In this way, if a single jig, such as a cutting jig is used to cut both the surface of the first vertebra and the surface of the second vertebra, orientation of the jig may be displayed on each separate display in relation to the corresponding vertebra being acted upon, thereby enabling simultaneous tracking of the two planes being resected for each separate vertebra on a dual display system. It will be understood that the tracked planes can be aligned or intersect in any appropriate manner or by any appropriate mechanism. For example, the planes may intersect at a selected point, such that the planes are not substantially parallel. In addition, the planes can be selected by a user, a system, a jig, an implant, or any other appropriate mechanism. Therefore, it will be understood that while two planes may be tracked substantially simultaneously, they can be defined or oriented in any appropriate manner. Additionally, each vertebra may be displayed on each of the dual displays so that the vertebra being tracked is shown with the adjacent vertebra superimposed adjacent thereto. Once the vertebra bodies are prepared, the implant is typically placed between each vertebra on the prepared site. Other ways of preparing this site is by using drills, reamers, burrs, trephines or any other appropriate cutting or milling device.

Briefly, the method, as shown in FIGS. 3*a* and 3*b*, demonstrates that the display 10 illustrated both the position and orientation of an object with respect to a desired position and orientation with six degrees of freedom accuracy. The display 10 may be automatically updated in real-time using the navigation system 44 to report the orientation of the tracked device. The user may also adjust the display 10 in order to control a device's orientation. The display 10 again consists of three rotational indicators (RX, RY, RZ) and three translational indicators or indicia (TX, TY, TZ). Each indicator shows both visual and quantitative information about the orientation of the device. Each indicator also displays a predetermined safe zone 112 and application-specific label for each degree of freedom. As noted, it may also be relevant to overlay the display 10 over anatomical image data from the imaging device 16. When working with 3-D image data sets, the anatomy normal to the tip 104 of the positioned device can provide the user with additional positional information.

Tones, labels, colors, shading, overlaying with image data can all be modified and incorporated into the display 10. The current display 10 is also shown as a Cartesian coordinate based display, but again could be based on a polar based display or a spherical based display and a quick switch between both can be supplied or simultaneously displayed. The display can also be configured by the user to hide parameters, location, size, colors, labels, etc.

Some medical applications that may be commonly displayed and linked to the display 10 are: 1) reaming of an acetabular cup with major focus upon RY and RZ, 2) length of leg during hip and knee procedures focused upon TZ and RZ, 3) biopsies and ablations focused upon RX, RY, and RZ for direction of the therapy device, and 4) catheters with side ports for sensing information or delivery of devices, therapies, drugs, stem cells, etc. focused upon six degree of freedom information.

Figure 4B:
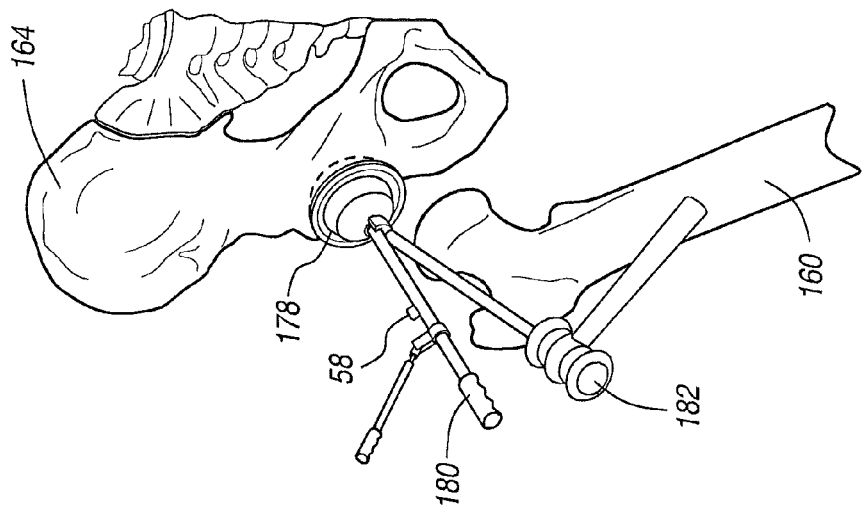
FIGS. 4a-4e illustrate a medical procedure employing the display according to the teachings of the present invention.
Figure 4A:
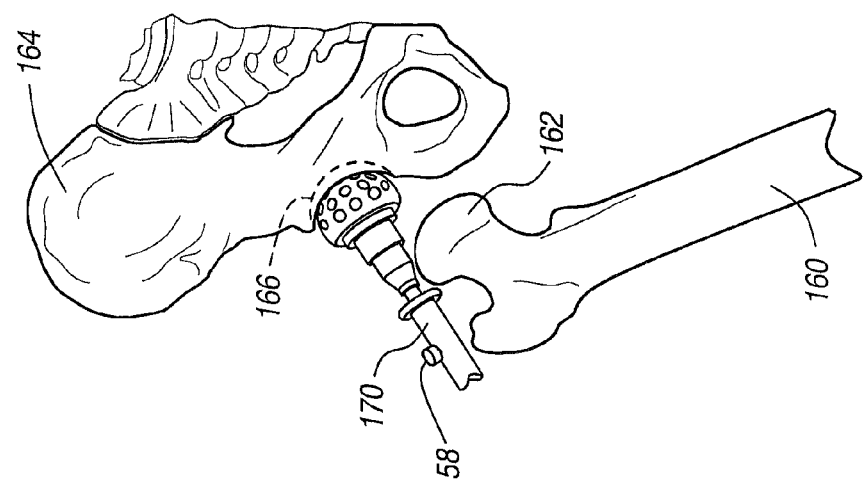
Figure 4E:
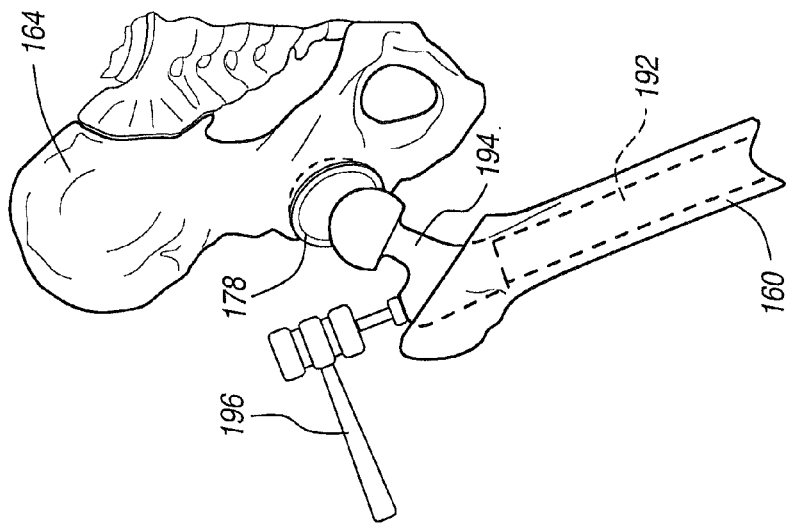

Referring now to FIGS. 4*a*-4*e*, a medical procedure employing a six degree of freedom alignment display 10 is shown in further detail. In this example, an orthopedic medical procedure replacing the hip joint is illustrated. During this procedure, various instruments 52, as well as the implants 52 are tracked and aligned using the six degree of freedom display 10. Referring specifically to FIG. 4*a*, a femur 160 having a femoral head 162 is illustrated, along with a pelvis 164 having an acetabulum 166. Assuming that the medical procedure being performed is an image based system, this area of interest will be imaged by the imaging device 16. Here again, the dynamic reference frame 54 may be attached to the femur 154 or the pelvis 164 or two dynamic frames 54 may be attached, one to each bone to provide additional accuracy during the medical procedure. With the head 162 dislocated from the acetabulum 166, a center of articulation of the acetabulum 166 is identified as the target 168, shown in FIG. 6.

In this regard, FIG. 6 illustrates the display 10 configured as a split screen with the right identifying the six degree of freedom display and the left illustrating the pre-acquired image with the center of articulation 168 being the intersection of the X, Y, and Z axes. As illustrated in FIG. 4a, a reamer 170 having a tracking sensor 58 is shown reaming the acetabulum 166. The tracking system 44 is able to accurately identify the navigation of the tip and hind of the reamer 170. As illustrated in FIG. 6, in the right half of the split screen, one can observe that the tip represented by the crosshairs 172 is properly positioned along the X and Y coordinates and within the corresponding safe zones 112, however, the hind portion of the instrument 170, as identified by the circle 174, is angularly offset from the target 168 at the origin. The surgeon can then angularly adjust the hind portion 174 of the instrument 170 until the hind portion 174 is shown in the display 10 as positioned over the crosshairs 172, thereby assuring proper alignment of the reaming device 170 for subsequent proper placement of the acetabular cup implant. By tracking the reamer 170, the surgeon can be relatively confident that an acetabular cup implant will be properly positioned before the implant is even impacted into the acetabulum 166.

Figure 7:
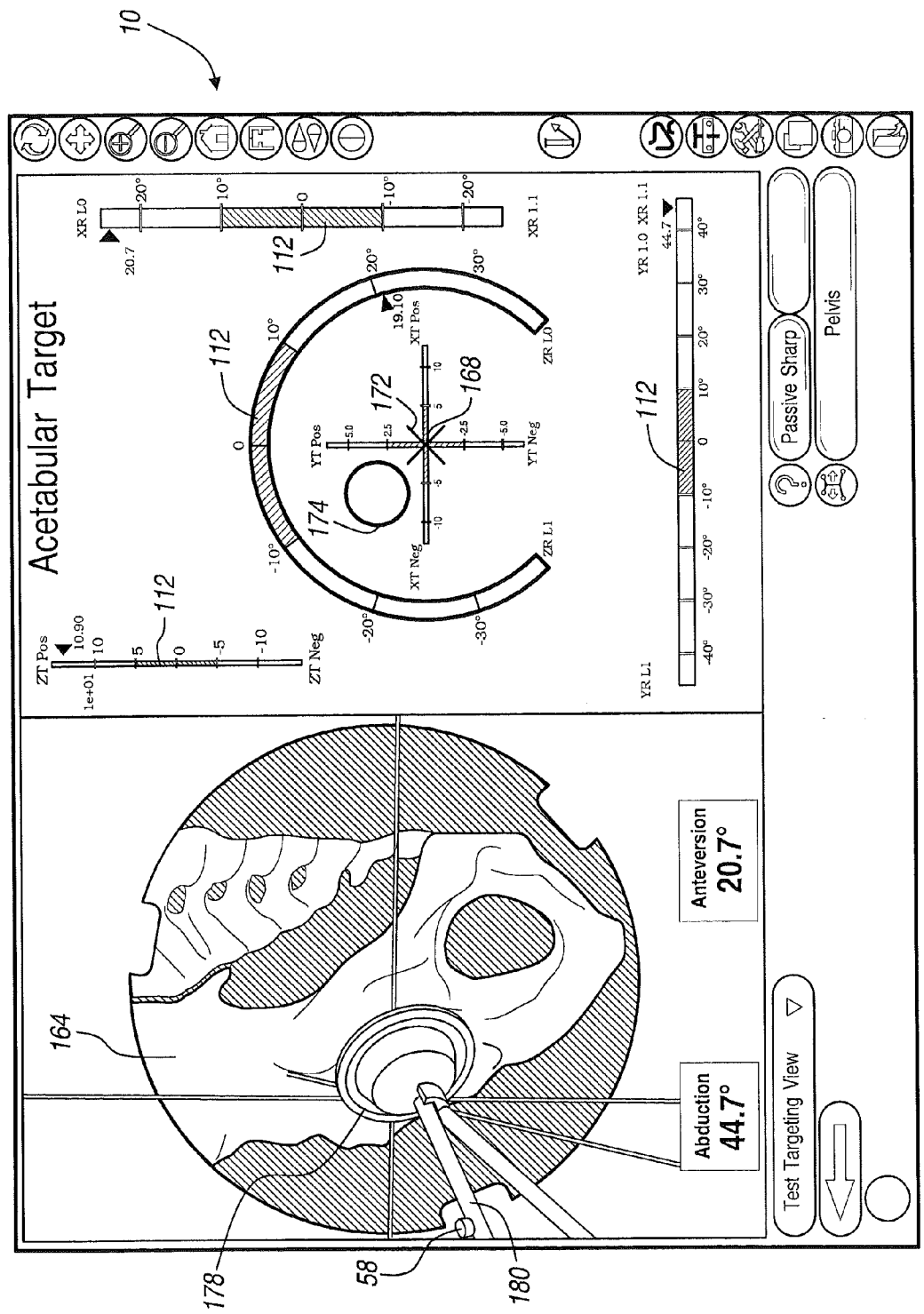
FIG. 7 is an additional split screen view of the display according to the teachings of the present invention.

Turning to FIG. 4b, an acetabular cup 178 is shown being impacted into the reamed acetabulum 166, via the tracked guide tool 180 with an impactor 182. The guide tool 180 has a distal end, which is nestingly received within the acetabular cup 178. Thus, by tracking the instrument 180, via tracking sensor 58, orientation of the acetabular cup 178 may be displayed on the display 10 in six degrees of freedom. In this way, before the acetabular cup 178 is impacted into the acetabulum 166, the surgeon can view on the display 10 whether the acetabular cup 178 is properly positioned at the proper angular orientation, as shown in FIG. 7, the impactor 180 is shown superimposed over an image generated by the imaging device 16. In this way, the proper orientation, including abduction and anteversion is achieved before the acetabular cup 178 is permanently implanted.

Once the acetabular cup 178 has been impacted, the femoral head 162 is resected along a plane 184 by use of a cutting guide 186, having the tracking sensor 58 and a saw blade 188. By using the center of the femoral head 162 as the second target, the cutting plane 184 may be properly defined to provide proper articulation with the acetabular cup 178 before a hip stem is implanted in the femur 160. Here again, the second target is dependent upon the first target. Thus, if the acetabular cup 178 was implanted somewhat offset from its target, the second target may be properly compensated to accommodate for this offset by use of the display 10. In this regard, a second display illustrating the target for the cutting plane 184 may be provided.

Figure 4D:
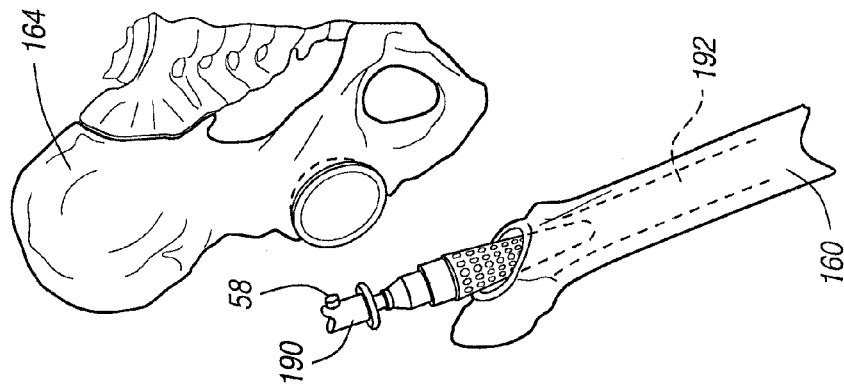
Figure 4C:
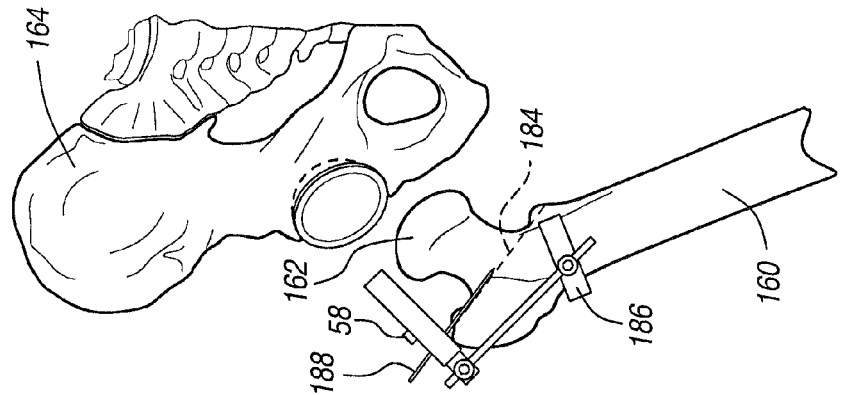

Once the femoral head 162 of the femur 160 has been resected, as shown in FIG. 4d, a reamer 190 is employed to ream out the intramedullary canal 192 of the femur 160. In order to provide proper angular orientation of the reamer 190, as well as the depth, a subsequent target can be defined and identified on the display 10 and tracked by use of the tracking sensor 58. This target may be displayed separately or in combination with the previously acquired targets. By insuring the proper angle of the reamer 190 relative to the longitudinal axis of the femur 160 is tracked and displayed on display 10, the surgeon can be provided a higher level of confidence that the hip stem will be properly positioned within the intramedullary canal 192.

Once the intramedullary canal 192 has been reamed by the reamer 190, a hip stem 194 is impacted with an impactor 196 into the intramedullary canal 192. By targeting the acetabular cup location, along with the resection plane 184 and the reaming axis of the reamer 190, upon positioning the hip stem 194, within the femur 160, proper articulation and range of motion between the acetabular cup 178 and the hip stem 194 is achieved without time consuming trialing as is conducted in conventional orthopedic procedures. Thus, by providing the safe zones 112 in relation to the hip stem 194 size, proper articulation with the acetabular cup 178 is achieved. Here again, while an example of an orthopedic hip replacement is set out, the six degree of freedom display 10 may be utilized with any type of medical procedure requiring visualization of a medical device with six degree freedom information.

The six degree of freedom display 10 enables implants, devices and therapies that have a specific orientation relative to the patient anatomy 14 to be properly positioned by use of the display 10. As was noted, it is difficult to visualize the correct placement of devices that require five or six degree of freedom alignment. Also, the orientation of multiple-segment implants, devices, or therapies in five and six degrees of freedom so that they are placed or activated in the correct orientation to one another is achieved with the display 10. Since the location and orientation is dependent upon one another to be effective, by having the proper orientation, improved life of the implants, the proper degrees of motion, and patient outcome is enhanced. Also, the six degree of freedom display 10 may be used as a user input mechanism by way of keyboard 38 for controlling each degree of freedom of a surgical robotic device. In this regard, the user can input controls with the joystick, touch screen or keyboard 38 to control a robotic device. These devices also include drill guide holders, drill holders, mechanically adjusted or line devices, such as orthopedic cutting blocks, or can be used to control and drive the alignment of the imaging system 16, or any other type of imaging system.

Since multiple implants and therapies, or multi-segment/compartment implants require multiple alignments, the display 10 may include a stereo display or two displays 10. These displays may or may not be linked, depending on the certain procedure. The target point/location (translation and orientation of each implant component is dependent upon the other implant placement or location). Therefore, the adjustment or dynamic targeting of the dependent implant needs to be input to the dependent implant and visually displayed. Again, this can be done by two separate displays or by superimposing multiple targets on a single display. Many implants such as spinal disc implants, total knee and total hip replacements repair patient anatomy 14 by replacing the anatomy (bone, etc.) and restoring the patient 14 to the original biomechanics, size and kinematics. The benefit of the six degree of freedom alignment display 10 is that original patient data, such as the images can be entered, manually or collectively, via the imaging device 16 or image-less system used for placement of the implant. Again, manually, the user can enter data, overlay templates, or collect data, via the imaging system 16. An example, as discussed herein of an application is the alignment of a femoral neck of a hip implant in the previous patient alignment. The previous patient alignment can be acquired by landmarking the patient femoral head by using biomechanics to determine the center and alignment of the current line and angle of the femoral head. This information can be used as the target on the display 10 in order to properly align the implant replacing the femoral head.

The six degree of freedom display 10 also provides orientation guidance on a single display. Separate visual and quantitative read-outs for each degree of freedom is also displayed on the display 10. Visual representations or indicia of procedure-specific accepted values (i.e., a "safe zone 112") for each degree of freedom is also clearly displayed on the display 10. These safe zones 112 are displayed as specifics or ranges for the user to align or place within. The procedure specific accepted values for the safe zones 112 can be manufacture determined, user determined, patient specific (calculated) or determined from algorithms (finite element analysis, kinematics, etc. atlas or tables). It can also be fixed or configurable. Safe zones 112 can also be defined as ranges around a planned trajectory path or the specific trajectory path itself (range zero). The trajectory paths are input as selected points by the user or paths defined from the patient image data (segmented vascular structure, calculated centers of bone/joints, anatomical path calculated by known computed methods, etc.).

Figure 8A:
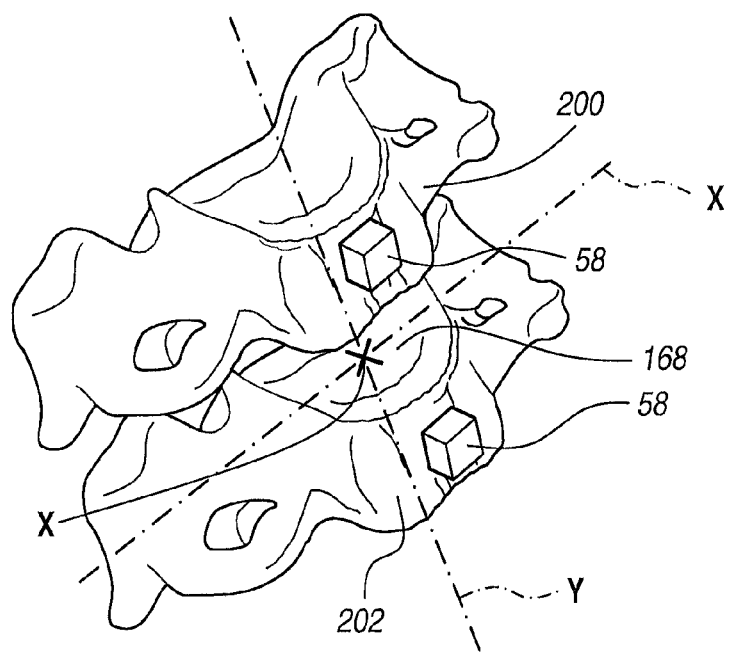
Figure 8B:
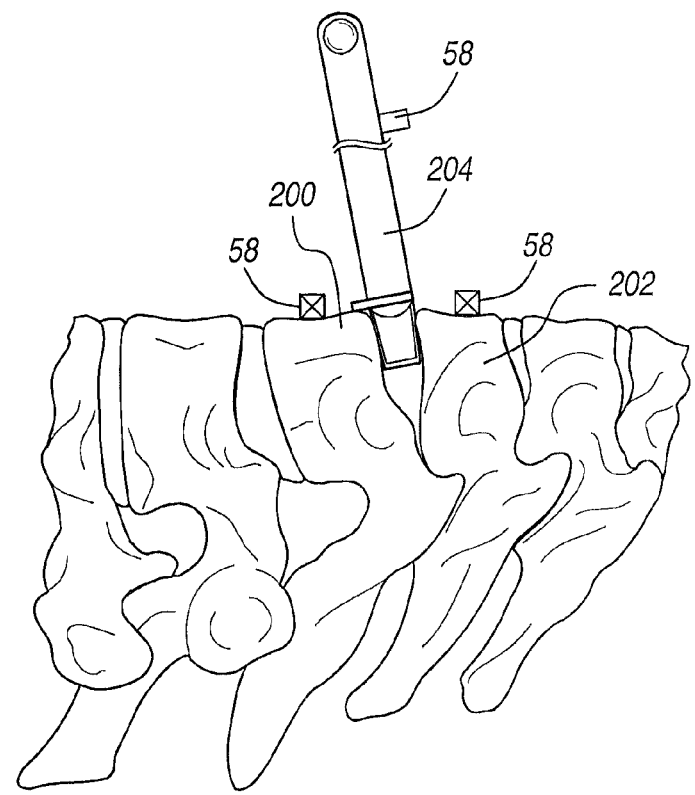
Figure 8C:
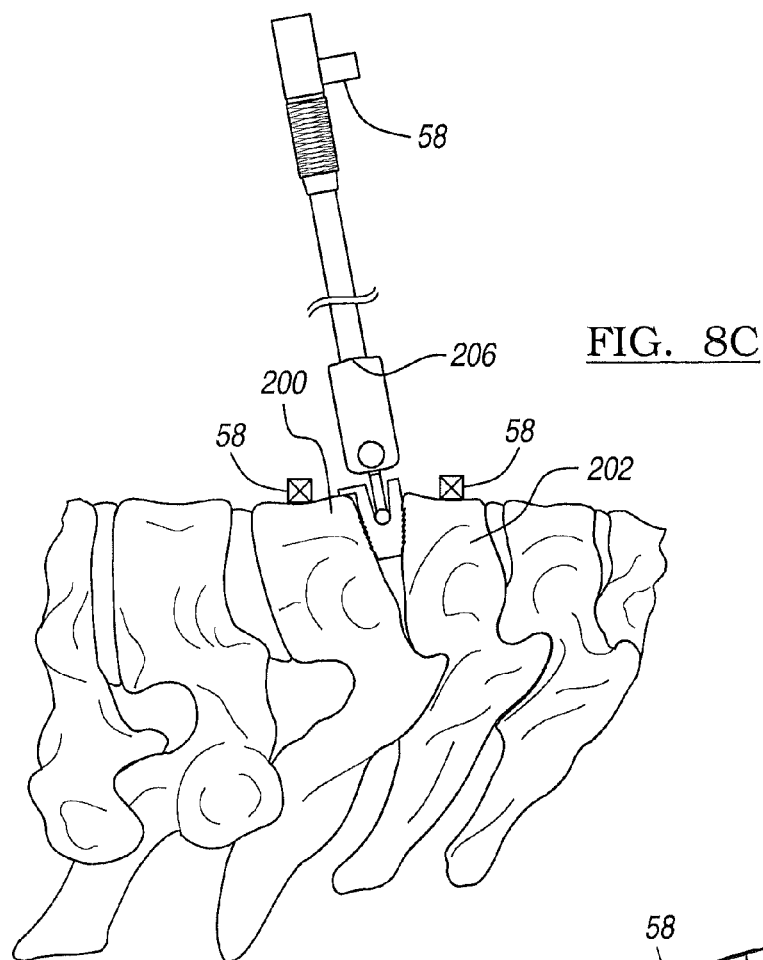
Figure 8D:
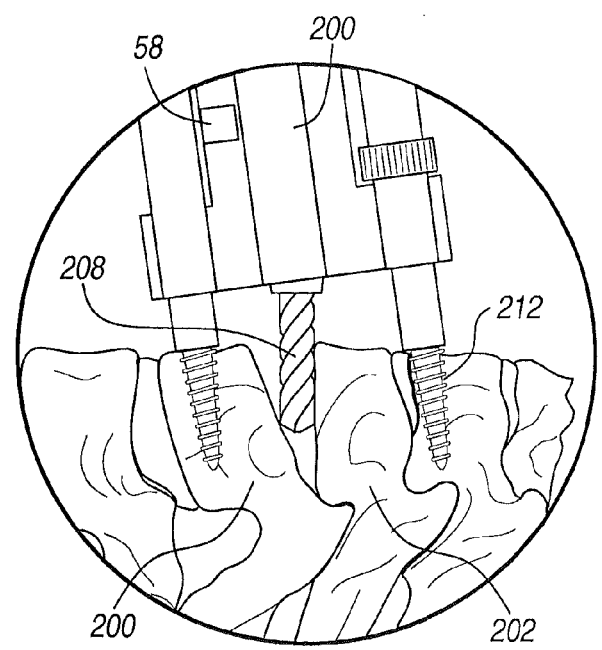
Figure 9:
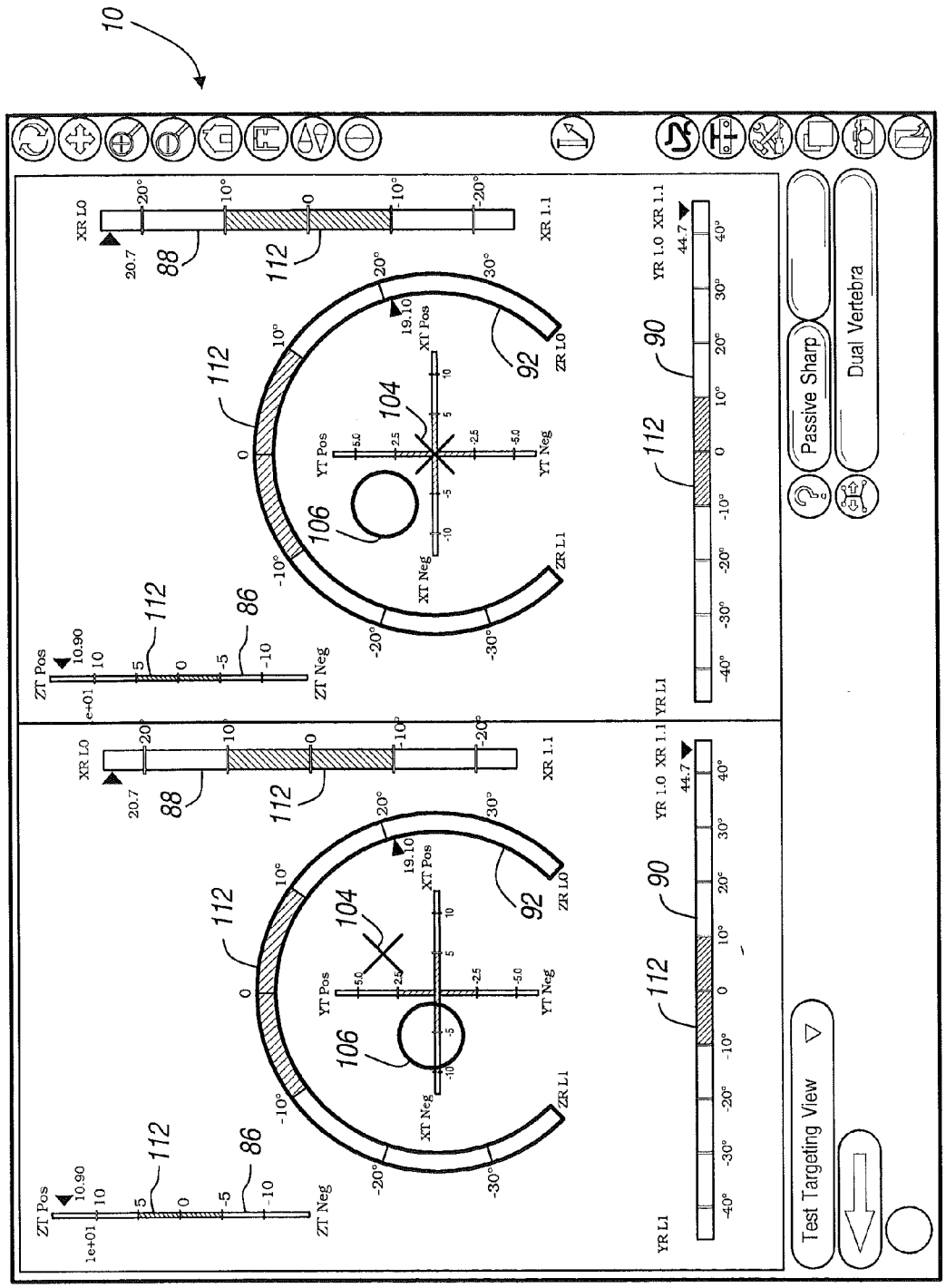
FIG. 9 is an illustration of a dual display according to the teachings of the present invention.

Turning now to FIGS. 8a-8g, another medical procedure that may employ the six degree of freedom alignment display 10 is shown in further detail, along with FIG. 9 illustrating the use of the display 10 during this medical procedure. In this example, a spinal medical procedure that implants a cervical disc implant between two vertebrae is illustrated. During this procedure, various instruments 52, as well as the implant 52 are tracked and aligned using the six degree of freedom display 10. Also, the bony structures during the procedure are also tracked.

Referring specifically to FIG. 8a, a first vertebra or vertebral body 200 is shown positioned adjacent to a second vertebra or vertebral body 202 of the spine. Assuming that the medical procedure is being performed in an image based system, this area of interest would be imaged by the imaging device 16. Again, a dynamic reference frame 54 may be attached to the first vertebra 200 and a second dynamic reference frame 54 may be attached to the second vertebra 202. These dynamic reference frames 54 may also be combined with tracking sensors 58, which are shown attached to the vertebral bodies 200 and 202. A center of articulation of the vertebra 200 and a center of articulation of a vertebra 202 may be identified as the targets 168 on the dual display illustrated on FIG. 9. In this way, by utilizing the center of articulation of each vertebral body with respect to each other as the targets 168, tracking of the instruments 52 used during the procedure, as well as the implant 52 with respect to these articulation centers may be achieved. This center of articulation or instantaneous center of rotation is identified as the "X" along axis Y. A plane or axis X is shown perpendicular to the longitudinal or spinal axis Y. This axis is where the implant, as well as milling should be performed or centered around. The implant may be positioned in any appropriate manner relative to the anatomical portions of the patient. For example, the implant may be positioned around and relative to the sagittal and/or coronal planes of the anatomy.

Referring to FIG. 8b, a cam distracter instrument 204 is shown distracting the vertebra 200 relative to the vertebra 202. The cam distracter 204 may be tracked, via another tracking sensor 58 affixed to the cam distracter 204. In this way, the six degree of freedom display 10 illustrated in FIG. 9 can illustrate a location of the cam distracter 204 relative to the center of each vertebra 200 and 202 independently on the display. Since the instrument 204 is rigid, by locating the tracking sensor 58 on the instrument 204, the distal end of the instrument 204 is known and may be illustrated on the display 10 using crosshairs 104 and circle 106 to represent the tip and hind, respectively.

Once each vertebrae 200 and 202 have been distracted by the cam distracter 204, a sagittal wedge 206 also having a tracking sensor 58 is utilized and shown in FIG. 8c. The sagittal wedge 206 is used to center each vertebrae 200 and 202, along the sagittal plane and again may be tracked and displayed with six degree of freedom on the display 10, as illustrated in FIG. 9. In this regard, the surgeon can confirm both visually and via the display 10 that the sagittal wedge 206 is centered on the sagittal plane between the vertebrae 200 and 202, as well as obtain the proper depth, via the Z axis display 86 on the display 10, illustrated in FIG. 9.

Once the sagittal centering has been achieved with the sagittal wedge 206, the medical procedure proceeds to burring as shown in FIG. 8d. In this regard, a burr 208 attached to a burring hand piece 210, also having a tracking sensor 58, is used to burr an area between the first vertebra 200 and the second vertebra 202. Here again, the orientation of the burr 208 relative to each vertebrae 200 and 202 may be displayed on the display 10 with six degree of freedom information. Therefore, burring along the proper X and Y plane, as well as the proper depth may be visually displayed with the appropriate indicia, as illustrated in FIG. 9. Rotational information about the corresponding X, Y and Z axes is also displayed. By burring within the safe zones 112 using the information regarding the surgical implant 52 as the safe zones 112, the surgeon can be assured to perform the proper burring between the vertebrae 200 and 202 to insure a proper oriented fit for the surgical implant 52. By tracking the burr 208 with six degrees of freedom information, the mounting anchors 212 for the hand piece 210 are optional and may not be required. Additionally, each single display in the dual display 10, as shown in FIG. 9, may also superimpose an image of each vertebrae 200 and 202 relative to one another on the display with each display having its coordinate system referenced to one of the vertebrae. The resulting milled vertebrae 200 and 202 are shown in FIG. 8e with a ring portion 214 milled to receive the spinal implant 52.

Referring to FIGS. 8f and 8g, the spinal implant 52 is shown being implanted between the vertebrae 200 and 202 using an implant inserter 216 that is also tracked by tracking sensor 58. The spinal implant 52 may be any type of cervical or other spinal disc implant for any other area of the spine. For example, the spinal implant may be the spinal implant disclosed in U.S. Pat. No. 5,674,296, entitled "Human Spinal Disc Prosthesis," issued Oct. 7, 1997, U.S. Pat. No. 5,865,846, entitled "Human Spinal Disc Prosthesis," issued Feb. 2, 1999, also known as the Bryan Cervical Disc System, offered by Medtronic Sofamor Danek of Minneapolis, Minn. or the Prestige Cervical Disc System, also offered by Medtronic Sofamor Danek, or any other spinal disc implant, all of which are hereby incorporated by reference. By tracking the implant inserter 216 relative to the vertebrae 200 and 202, proper orientation of the spinal implant 52, as well as rotational orientation about the Z axis can be clearly displayed on the six degree of freedom display 10, as shown in FIG. 9. Rotation about the Z axis is used to make sure that the flanges 218 of the implant 52 are properly oriented and centered along the sagittal plane, as shown in FIG. 8g. Again, by using the display 10, as illustrated in FIG. 9, the anchors 220 are optional since orientation of the implant 52 can be tracked continuously as it is inserted between the vertebrae 200 and 202. Here again, this eliminates the need for forming holes in the vertebrae 200 and 202. It should further be noted that the implant 52 illustrated in these figures is merely an exemplary type of spinal implant and any known spinal implants may also be similarly tracked. For example, another common type of spinal implant is formed from a two-piece unit that includes a ball and cup articulating structure that may likewise be independently tracked to assure proper fit and placement.

Here again, the six degree of freedom display 10, which is illustrated as a split or dual display 10 in FIG. 9 assists a surgeon in implanting a spinal implant 52 in order to achieve proper fixation and orientation of the implant 52, relative to two movable vertebrae 200 and 202. By tracking each vertebra 200 and 202 independently, and tracking its resection, should one vertebra be resected off-plane due to anatomical anomalies, adjustment of the plane at the adjacent vertebra may be achieved in order to still provide a proper fit for the spinal implant 52. In this way, each vertebrae 200 and 202 can be independently monitored, so that if one is off axis, the other can be manipulated accordingly to account for this adjustment. Additionally, by monitoring the entire process having six degree of freedom information, via display 10, further accuracy was achieved, thereby providing increased range of motion for the patient after implantation of the implant 52.

By use of the six degree of freedom display, for the various types of medical procedures, improved results can be achieved by providing the surgeon with the necessary information required. In regard to surgical implants, the range of motion may be increased while reducing impingement of two-part articulating or fixed implants. This also enables maximum force transfer between the implant and the body. With therapy delivery procedures, by knowing the location of the catheter delivery tube and the specific port orientation, accurately aiming at the site is enabled to provide maximum delivery of the therapy at the correct site. This procedure also enhances and enables better results when using an ablation catheter by again knowing the rotational orientation of the ablation catheter and the ablation electrode relative to the area in the wall of the artery that requires ablation. Finally, by knowing the rotational orientation of a ablation or biopsy catheter, this type of catheter may be easily directed and aligned to tumors, stem cells, or other desired sites in an easy and efficient manner.

Figure 10:
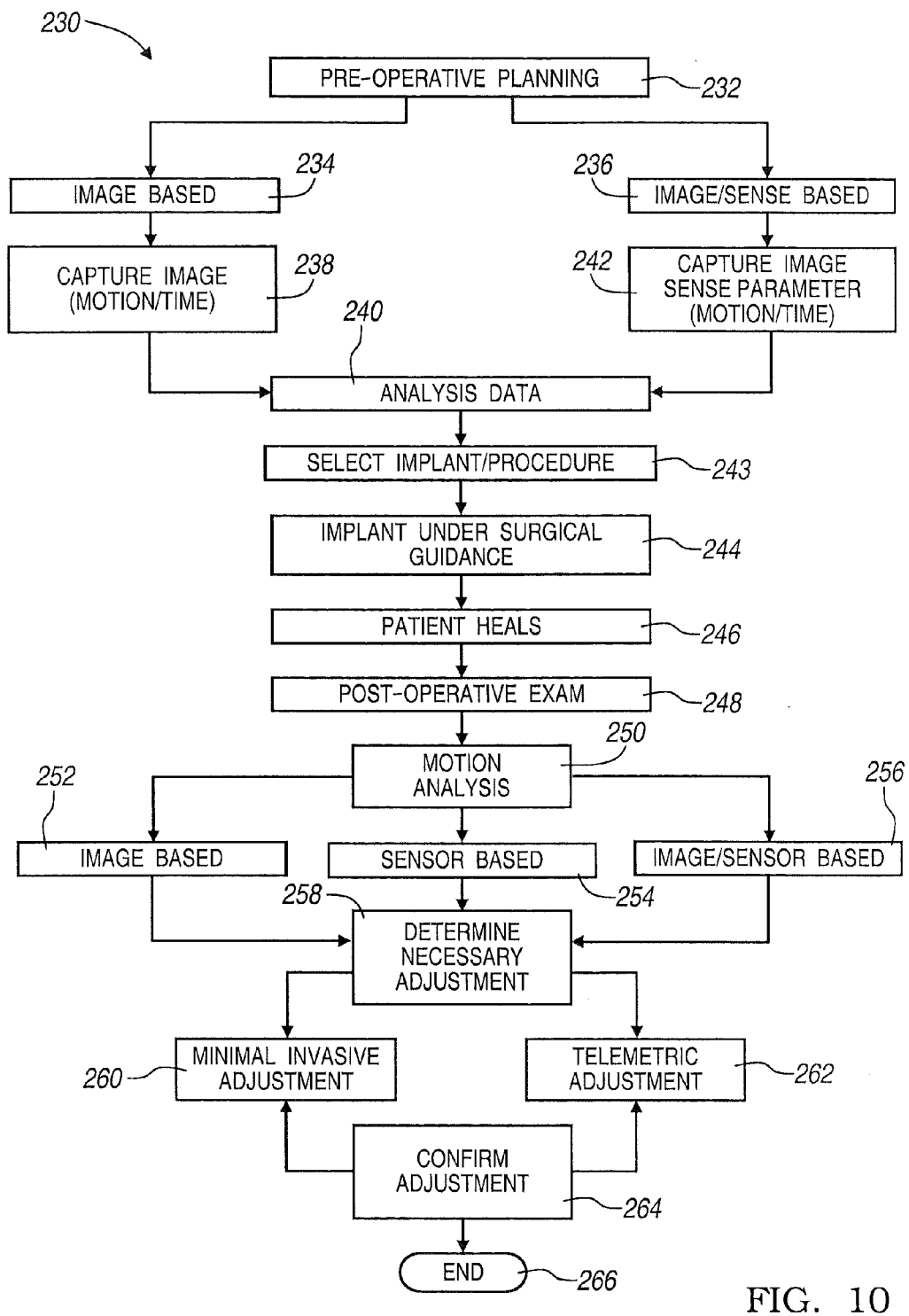
FIG. 10 is a logic block diagram illustrating a method for pre-operative planning and post-operative exam and tuning of an implant according to the teachings of the present invention.

Turning to FIG. 10, a method 230 for post-operative adjustment or tuning of implants, such as a spinal implant, according to the teachings of the present invention is disclosed. The method 230 also includes pre-operative planning, implanting, as well as the post-operative exam procedure. In this regard, the method 230 begins at block 232 where pre-operative planning of the medical procedure begins. The pre-operative planning proceeds from block 232 to either block 234 if an image based pre-operative plan is conducted or block 236 if both an image and sensing pre-operative plan is conducted. If an image based pre-operative plan is being conducted, the method proceeds to block 238 where pre-operative image data is acquired. The pre-operative images may be captured from a four-dimensional CT scan, which provides for capturing images over a specific time frame. In this regard, if the pre-operative planning is for implantation of a cervical disc, the patient may be asked to move his or her neck in different manners to capture the image data over time. Alternatively, any other type of imaging device 16 may be employed to either simply gather static image data or image data over time. The captured image data may also be used in conjunction with the electromagnetic tracking system 44, as discussed herein. Another example of pre-operative planning using a tracking system is disclosed in U.S. Pat. No. 6,470,207, entitled "Navigation Guidance Via Computer-Assisted Fluoroscopic Imaging," issued Oct. 22, 2002, which is hereby incorporated by reference. Other types of pre-operative planning using a tracking system may also be employed. This image data is then analyzed at the analysis data block 240, further discussed herein.

Should the pre-operative planning proceed to block 236, which employs the image and sense-based pre-operative planning, this procedure will capture image data and sense parameters at block 242. In this regard, the captured image data may be the same image data that is captured at block 238. In addition to the captured image data, various parameters in the area of interest may also be sensed during the pre-operative planning state. In this regard, probes or sensors maybe placed in the area of interest to sense the parameters, such as temperature, pressure, strain, and force motions. For example, in a cervical disc implant, sensors may be positioned between adjacent vertebrae of interest to measure temperature in certain areas, which may indicate friction or impingement. Likewise, strain gauges may be positioned to measure forces to identify areas having unacceptably high forces between the vertebrae. Again, this data is then analyzed at block 240.

At block 240, the data from either the image based or the image sense based pre-operative planning is analyzed. Should the data only include image data from block 238, this image data may be used to identify areas of interest, the patient size, and be used to assist in preparing the surgical plan. By viewing this data, such as 4D data, which is essentially 3D data over time or static image data, certain abnormal or irregular movements in the area of interest may be identified. These areas may be identified by visual examination, by performing finite element analysis or other known motion analysis to create a 3D model of the captured image. The finite element analysis may include calculating the instantaneous center of rotation "x" or make this determination from the image data itself. The overall shape of the spine may also be analyzed via the image data to identify and determine various force vectors on the discs of interest by analyzing the entire spine, the curvature of the spine and the articulation area of the angle of the spine relative to the ground. This information may be used to find force vectors and loading on the various regions of the vertebrae of interest. Should the sensed parameters also be used, or alternatively only be used, these sensor readings, which can be measured statically or actively while the patient is moving are utilized to again identify points of interest or potential abnormal activities by sensing parameters, such as temperature, pressure, stress, and strain in the area of interest.

Once the data has been analyzed at block 240, the procedure proceeds to block 243, where the implant and the type of procedure is selected. The implant is selected, based on the various abnormalities identified in order to enable the surgeon to resolve the noted abnormalities. The implant is selected based on various parameters, such as material selection, performance characteristics, stiffness, style or implant type and sizing. Once the type of implant has been selected, sizing of the implant may also be pre-operatively performed, based on the data captured and analyzed at block 240. Sizing may be performed using known sizing templates, which provides the surgeon with a visual means of correlating the size of the implant to the area of interest. Alternatively, various sized templates automated in software may also be included and stored within the work station 36 and superimposed in the area of interest to provide a visual indication of the sized implant to select. In addition to selecting the type and size of the implant, the type of procedure to position the implant may be determined pre-operatively.

Once the size and type of implant is selected, as well as the type of procedure, the procedure proceeds to block 244. At block 244, the selected implant is implanted generally under surgical guidance in the area of interest. For example, a cervical disc implant may be implanted, as illustrated in FIGS. 8a-8g. However, any other type of implant procedure may also be performed to position the selected implant, which may include a non-surgically guided procedure. Other exemplary types of surgically guided procedures are set out in U.S. Pat. No. 6,470,207, entitled "Navigation Guidance Via Computer- Assisted Fluoroscopic Imaging," issued Oct. 22, 2002; U.S. Pat. No. 6,434,415, entitled "System For Use in Displaying Images Of A Body Part," issued Aug. 13, 2002; and U.S. Pat. No. 5,592,939, entitled "Method and System for Navigating a Catheter Probe," issued Jan. 14, 1997, all of which are hereby incorporated by reference.

After implantation, there is a recovery period, exemplified by block 246. The recovery period will vary depending on the type of procedure, the type of implant, the patient's medical history and age, and other variables. During this period, the area of abnormality surrounding the implant may also heal and recover. For example, if a cervical disc was implanted, the muscular structure surrounding this area, which may have previously been overcompensating because of the abnormality may now have returned to a normal state. These surrounding structure changes, may affect the way the implant was positioned within the patient or the performance characteristics of the implant. In this regard, if the implant was positioned based upon abnormal surrounding structure, the implant may subsequently not provide the full range of motion as anticipated, thereby potentially resulting in further surgeries being required. Alternatively, the initially selected performance characteristics of the implant may have changed to due subsequent healing or other actions, thereby rendering the initial performance characteristics inappropriate for the current patient's condition. These performance characteristics can be any type of characteristics regarding the implant, including stiffness, actuation, loading, range of motion, etc. With the implant being an adjustable or tunable implant, corrections may be made to compensate for any subsequent anomalies observed by the surgeon. Again, the anomalies may result from healing of surrounding tissue, incorrect initial placement, changes in performance characteristics, or any other reasons. It should also be pointed out that if undesirable performance characteristics result after healing, the surrounding tissue and discs may also be damaged or deteriorate, thereby compounding recovery time and maybe requiring additional implants. This is the reason that providing the proper performance characteristics after healing is so critical.

After the patient has healed for some time, a post-operative exam is performed, exemplified at block 248. This post-operative exam may be conducted in different manners, depending upon the type of implant, the type of sensors and controls available with the implant, as well as the types of adjustments available with the implant. Some implants may have adjustment capabilities that require minimally invasive percutaneous type procedures, while other implants can be adjusted telemetrically or adaptively, as further discussed herein. The pre-operative exam may also be carried out using various types of equipment, again depending upon the capabilities of the implanted device, further discussed herein.

The pre-operative exam includes a motion analysis study, represented by block 250. This motion analysis study generally involves articulating the area of interest to determine range of motion, strength, etc. During this motion analysis study, the patient 14 is typically put through various motion testing. This testing may include various calisthenics, treadmill performance, weight lifting, gate analysis, etc. The motion analysis 250 can be performed and studied using an image-based procedure, set out at block 252, a sensor-based procedure, set out at block 254, or an image and sensor-based procedure, set out in block 256. It should also be pointed out that while block 250 is labeled motion analysis, the analysis can be performed via static image-based procedures or static sensor-based procedures, which are contemplated and included in the motion analysis study 250. In this regard, as opposed to putting the patient through various motion tests, the static image data or sensed data can be obtained and reviewed, via the image-based block 252 or the sensor-based block 254 to determine if the performance characteristics have changed. These static studies would simply look at the proper placement, impingement, etc. in the areas of interest to be used for subsequent post-operative tuning, further discussed herein.

The image-based procedure may be performed by either employing a localization or navigation tracking system or capturing image data, such as 3D or 4D image data, by an imaging device, such as a 4D CT imaging device. Should the motion analysis study be performed using localization or navigation technology, capturing image data and registration is performed as disclosed herein. U.S. Pat. No. 6,434,415, entitled "System for Use in Displaying Images of a Body Part," issued Aug. 13, 2002, also discloses pre-operative planning using navigation technology, which is hereby incorporated by reference. In general, pre-acquired image data may be obtained, for example, in the cervical spinal region. Before this image data is obtained, fiducial markers and localization sensors may be attached to each vertebrae of interest. Once the image data has been captured with these sensors in place, the patient 14 may be positioned on a treadmill with the tracking system 44 placed in proximity to track the motion of each vertebrae. This motion can include a gate analysis study of the patient's motion as well. Before the motion analysis begins, the navigation space of the patient 14 is registered to the pre-acquired images. Once the patient 14 begins the motion or movement for the motion analysis 250, tracking of the moving vertebrae may be captured and illustrated on a display, such as the display 10, or any other display.

If localization and navigation technology is not employed, image data may simply be captured over time during the motion analysis 250, for example, by the use of a four-dimensional CT scan. With this image data captured, each individual vertebrae may be segmented out using known segmenting algorithms. These types of algorithms generally involve thresholding or templates, which will segment out each vertebra in the scan. Once each vertebrae is segmented out, finite element analysis may be performed using known finite element analysis. The finite element analysis may also be used to calculate the instantaneous center of rotation "x". The information gathered during motion analysis 250 is used to determine the necessary adjustment of the implant at block 258. This information may include visualization of impinged areas around the implant, misalignment, etc.

Should the motion analysis be sensor-based, as illustrated at block 254, the sensor readings of various parameters are used to determine if there is any necessary adjustment, at block 258. The sensor based approach may either take readings from sensors located within the implant or from sensors attached to the patient during this analysis. The sensors may take temperature readings, which can indicate potential friction and higher forces, strain or stress readings, as well as load readings or any other parameter readings. Again, this information is used at block 258 to determine the necessary adjustment to the implant.

At block 256, both an image and sensor-based motion analysis may be conducted. This analysis essentially combines the image data at block 252 and the sensor data at block 254 to perform the post-operative analysis of the patient. Again, this information is used at block 258 to determine any necessary adjustments of the implant. When using both the image and sensor-based motion analysis, the sensed parameters may be synchronized in time with the image data to provide information on when the sensed parameters were captured relative to the time and the image.

At block 258, the data captured during motion analysis 250 is studied to determine whether any adjustments are necessary relative to the implant. For example, if a cervical disc was implanted and the patient healed and subsequent spinal alignment occurred, the range of motion may be compromised. In order to provide the proper range of motion, post-operative tuning of the implant may be necessary, based on the motion analysis study 250.

The post-operative tuning of the implant may also be necessary when the performance characteristics of the implant have changed. Performance characteristics may be selected, based on various criteria, such as when the patient is in a relatively static state, thus requiring certain performance characteristics, as compared to when the patient is in vigorous active state, where the performance characteristics must be changed. For example, the spinal implant may not need significant stiffness in a relatively static condition, while in very active condition, the spinal implant may require a stiffer cushioning. The performance characteristic may have been selected when the patient was disabled, so that once the patient heals, the performance characteristics may have to be adjusted accordingly. This adjustment may be conducted using a minimally invasive adjustment procedure at block 260 or a telemetric adjustment procedure at block 262.

In the minimally invasive adjustment at block 260, percutaneous adjustment of the implant may be performed by actuating various adjustment mechanisms within the implant, further discussed herein. For example, adjustment screws may be positioned at hinge points within the implant and engaged by a driver in a minimally invasive type procedure to provide the proper adjustment, thereby reacquiring the proper range of motion, via adjusting the articulating surfaces of the implant. Adjustment of the performance characteristic, such as stiffness may also be performed, as further discussed herein.

Should a telemetric adjustment procedure be performed at block 262, a non-surgical adjustment would be performed. In this regard, the implant may be driven telemetrically, using known telemetric type wireless systems, such as that disclosed in U.S. Pat. No. 6,474,341, entitled "Surgical Communication Power System," issued Nov. 5, 2002, which is hereby incorporated by reference or any other known wireless telemetric systems. The telemetric system may be an RF based or electromagnetic based telemetric system, as is known in the art. The implant may be a passive or active battery powered device that includes motors, pumps or any other devices used to adjust the implant, further discussed herein.

Once the adjustments have been performed, the procedure proceeds to block 264 where the adjustment is confirmed. If the adjustment is proper, the procedure ends at block 266. If not, further adjustments are performed. This pre-operative and post-operative procedure provides better initial implantation accuracy and implant selection, as well as the opportunity for post-operative tuning or adjustment of the implant. The post-operative tuning enables adjustment of articulating surfaces, supports, or other parameters within the implant post-operatively without requiring revision surgery.

Figure 11:
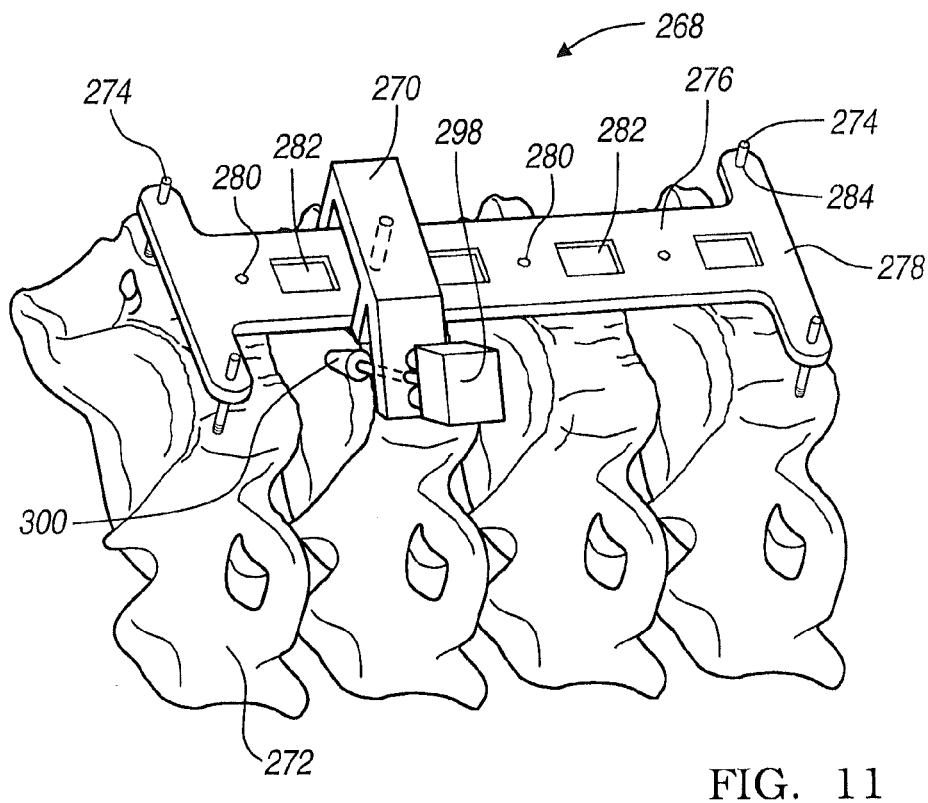
FIG. 11 is a perspective view of a platform and jig used in a minimally invasive surgical navigation spinal procedure.
Figure 12:
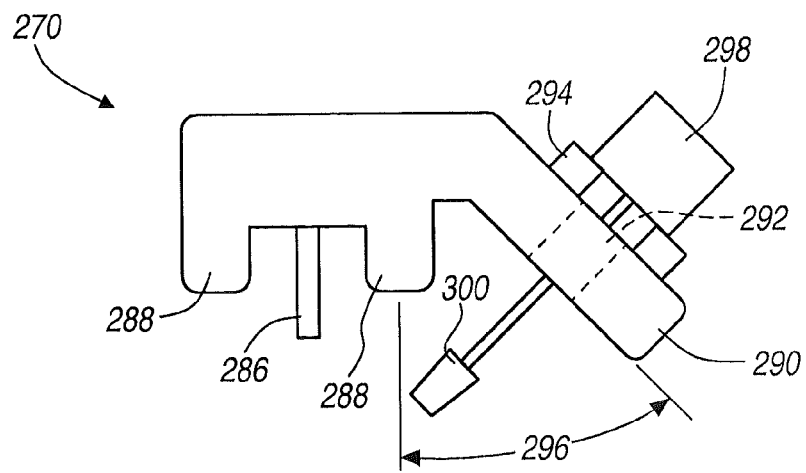
FIG. 12 is a perspective view of the jig that is operable to be attached to the platform of FIG. 11.

Referring to FIGS. 11 and 12, an instrument assembly that includes a mounting platform 268 and an attachment jig 270 for use in a surgical navigated spinal procedure is illustrated. The mounting platform 268 is percutaneously attached to a series of vertebrae 272, via multiple K-wires 274. In this regard, the mounting platform 268 is positioned outside the patient's body and above the vertebrae 272 of interest. The mounting platform 268 may be sized to span any number of vertebrae 272. In this example, four vertebrae 272 are spanned with the mounting platform 268 with the first and fourth vertebrae being secured to the mounting platform, via K-wires 274. The mounting platform 268 is designed to retain the spanned or captured vertebrae 272 in a relatively fixed or rigid manner during the spinal disc implant procedure. With the first and last vertebrae captured via the K-wires, the intermediate vertebrae 272 are generally held in a substantially fixed manner. Upon removing cartilage and other intermediate material between adjacent vertebrae, additional K-wires may be necessary for the intermediate vertebrae 272 to maintain the rigid structure.

The mounting platform 268 generally includes a rectangular-shaped beam 276 and a pair of outer attachment members 278. The rectangular beam 276 defines a plurality of peg holes 280, which are used to adjustably and removably retain the jig 270, along the member 276. The rectangular beam 276 also defines access and viewing holes or ports 282 enabling access from above and viewing of the relevant vertebrae. These access windows 282 can also be used to receive or pass surgical instruments during the medical procedure. Each attachment member 276 defines K-wire holes 284, which slidably receive the K-wires 274 in order to retain and secure the mounting platform 268 relative to the vertebrae 272.

An exemplary positioning jig 270 is illustrated in further detail in FIG. 12 and is operable to be removably attached to the mounting platform 268, as shown in FIG. 11. In this regard, the jig 270 includes attachment peg 286 that is slidably received within holes 280. Positioned adjacent to the peg 286 is a pair of shoulders 288 that extend on either side of the rectangular beam 276 as the peg 286 is received within the hole 280. The jig 270 may be positioned along any part of the rectangular beam 276 by simply slidably inserting the peg 286 into one of the selected holes 280. Alternatively, any type of attachment mechanism to attach the jig 270 to the mounting platform 268 may be used. Once the peg 286 is positioned in one of the selected holes 280, the jig 270 is positioned substantially between a pair of vertebrae 272 in which the surgical procedure will be performed. The jig 270 further includes a work platform 290 that defines a passage 292 and includes a securing mechanism 294. The work platform 290 is positioned at an angle relative to the mounting platform 268 to provide intervertebral body access. The angle 296 illustrated with jig 270 provides for a 45° working platform 290. It should also be pointed out that multiple jigs 270 may be provided with the working platform 290 being positioned at various angles or the jig 270 may be adjustable to vary the angle, via a hinge or an adjustment mechanism between the working platform and the body of the jig 270.

The working platform 290 enables various instruments to be attached to the working platform, via the attachment mechanism 294, which may be a screw attachment, quick lock attachment, snap-fit attachment, or any other type of attachment mechanism. In one embodiment, a robot 298 may be attached to the working platform 290. This robot 298 may be remotely controlled and be used to drive milling, drilling, resection, or other instruments 300 through the passage 292. The robot 298 can either actuate the motor for the instrument 300 or can simply provide and act as an adjustable guide tube that may be controlled directly or remotely. Any type of known robotically controlled instrument may be utilized. Alternatively, the jig 270 may retain a manually adjustable guide tube that receives various instruments to be used during the procedure. The adjustable guide tube may also be lockable into a desired position in order to provide a rigid guide tube. Still further, the jig 270 may simply be used to pass and guide various instruments between the vertebral bodies 272. In this regard, the instruments as illustrated in FIGS. 8a-8g may be used in accordance with the jig 270 or other jigs providing various types of access ports 292. These access ports may be circular, slotted or any other shaped port to enable access between the vertebral bodies 272.

Generally, the mounting platform 268 will not include any localization sensors 58 or fiducial markers 60. The localization sensors 58 are generally positioned relative to the jig 270. The localization sensors 58 may be positioned on the guide tube and on the surgical instrument to determine orientation and depth of the surgical instrument 300, respectively. The localization sensor 58 may also be positioned on the robotically controlled device 298 to determine both orientation and depth of the instrument 300. The mounting platform 268 may also include localization sensors 58 if desired, which may be used to provide further localization of the vertebrae 272. It should further be pointed out that the dynamic reference frame 54 may be attached or integrated into the mounting platform 268 in order to provide increased accuracy during the implant procedure. In this regard, since any motion of the mounting platform 268 would be identified, via an integrated dynamic reference frame 54, this motion is positioned substantially adjacent to the area of interest and the area being operated upon, providing increased registration and tracking of the instruments during the procedure.

By providing the mounting platform 268 that spans multiple vertebrae, multiple segment implantation may be performed in a minimally invasive and surgical navigated manner between the multiple vertebrae 272. For example, as illustrated, three separate cervical discs may be positioned between the four vertebrae 272 without requiring removal or replacement of multiple jigs as would typically be necessary. By providing a mounting platform 268 that can accommodate various size jigs and can be positioned between various vertebrae 272, a more precise and accurate implantation may be achieved in a more minimally invasive and efficient manner.

Figure 13:
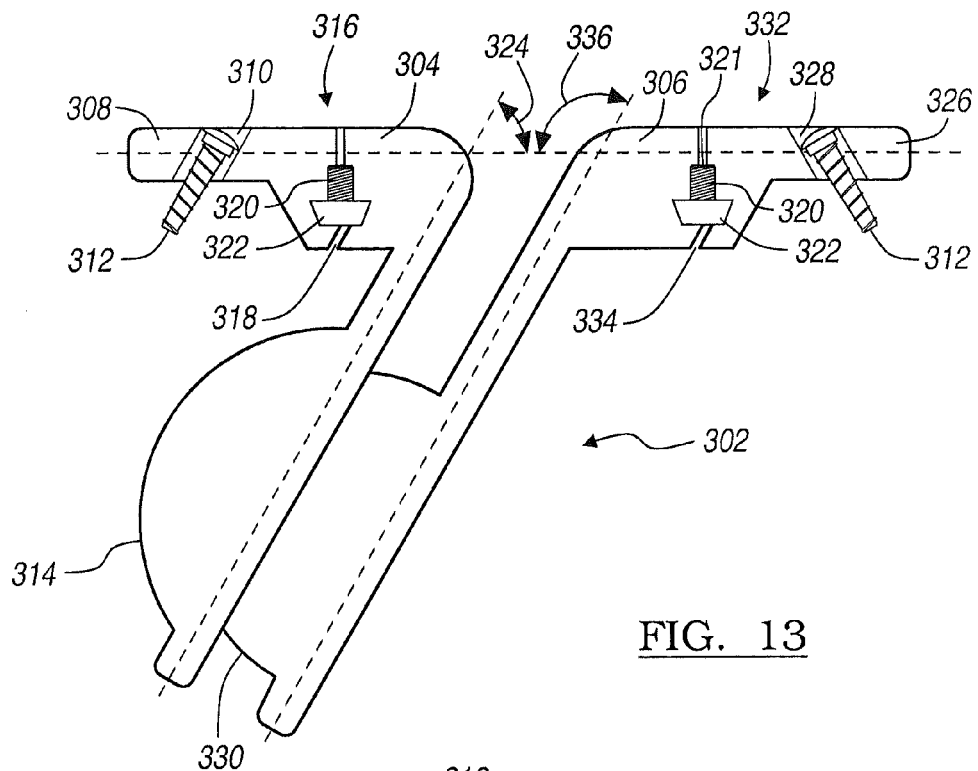
FIG. 13 is a side view of a cervical disc implant having a minimally invasive adjustment mechanism.

A ball and socket type cervical disc implant 302 is illustrated in FIG. 13 that provides for percutaneous adjustment. The cervical disc implant 302 is based upon the Prestige® and/or Brian® Cervical Disc System or the Maverick Lumbar System®, both provided by Medtronic Sofamor Danek of Memphis, Tenn., and may include a tuning or adjustment capability. It should also be pointed out that while a cervical disc implant is disclosed herein, the present invention is not limited to merely cervical disc implants, but may include thoracic and lumbar spinal implants, as well as any other type of orthopedic implant that may require post-operative tuning. The cervical disc 302 comprises two articulating members that include a socket member 304 and a ball member 306. The socket member 304 includes a mounting flange 308 that defines generally two mounting holes 310 for receiving bone screws 312. The socket member 304 also defines the articulating socket 314 and is generally placed at an angle relative to the flange 308. Located at the junction between the flange 308 and the socket 314 is an adjustment or hinge region 316 defining an adjustment slot 318. Located within the adjustment slot 318 is an adjustment screw 320. Upon percutaneously engaging a head 321 of the adjustment screw 320, via any known driving instrument, the angle 324 between the flange and the socket 314 may be adjusted, via a wedge portion 322, in a minimally invasive manner. The head 321 may include a hex, a Phillips, a slotted, or any other type of engagable drive mechanisms that can be engaged by any type of instrument. Moreover, the adjustment screw 320 may be reversed so that the head 321 is located opposite, at 90°, or at any other orientation other than as illustrated to provide a different access point for the head 321.

The ball member 306 also includes a flange 326 defining screw holes 328 to receive bone screws 312. The ball member 306 also includes an articulating ball or spherical surface 330 that articulates with the socket 314. The flange 306 also includes adjustment or tuning portion 332 that defines a slot 334 for receiving another set screw 320 having head 322. Again, upon adjustment of the set screw 320, the angle 336 between the flange 326 and the ball 330 is adjusted in a minimally invasive manner, via percutaneous placement of a surgical driver that engages the head 321 of the adjustment screw 320.

By providing tuning or adjustment portions 316 and 332 relative to the ball 330 and socket 314, adjustment of the articulating ball 330 relative to the socket 314 may be made. Again, after a motion analysis 250 has been performed, a minimally invasive adjustment of the implant 302, such as the implant shown in FIG. 13 may be performed by simply adjusting set screws 320. This adjustment may relieve impingement, increase range of motion, or provide other post-operative adjustments that would previously require a revision type surgical procedure.

Figure 14:
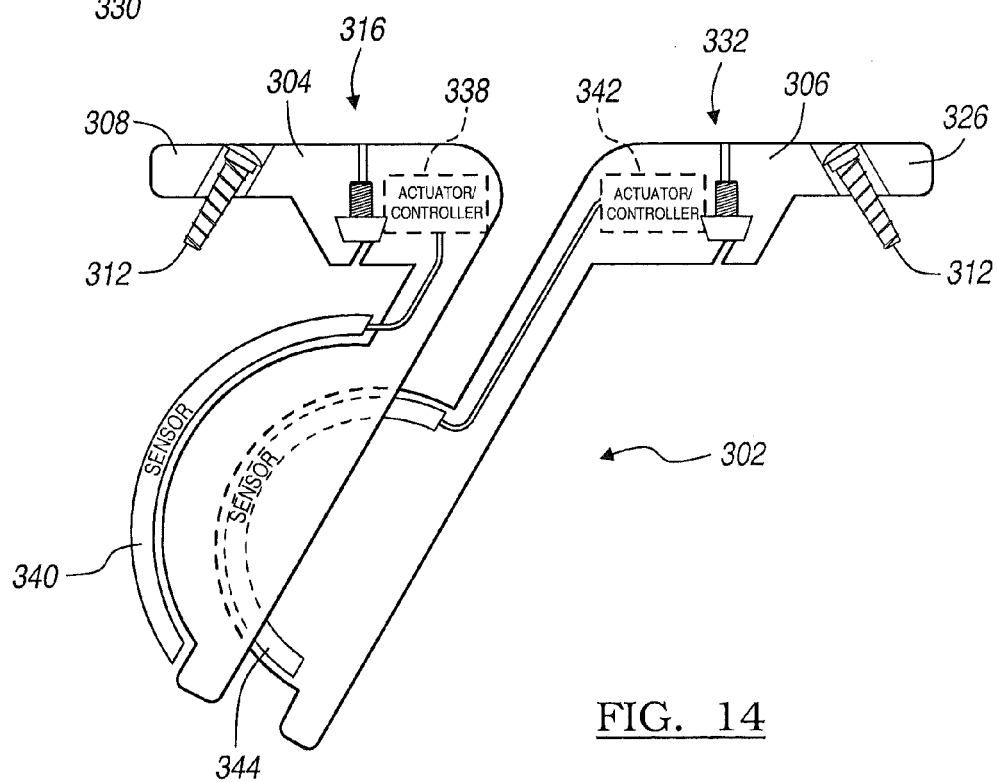
FIG. 14 is a side view of a cervical disc implant having a telemetric adjustment mechanism.

Referring now to FIG. 14, a modified embodiment of the cervical disc 302 is illustrated. In this regard, like reference numerals will be used to identify like structures as shown in FIG. 13. The implant 302 provides for a telemetric type adjustment, as well as telemetric sensing capabilities. In this regard, the socket member 304 includes an actuator/controller 338 and a sensor 340 positioned along the articulating surface of the socket 314. Likewise, the ball member 306 also includes an actuator/controller 342 and a sensor 344 positioned along the articulating ball surface 330. The sensors 340 and 344 may be used to sense various parameters in the articulating joint, including temperature, pressure, stresses, strain and other loading properties. These sensors 340 and 344 may be used during the sensor based motion analysis 254 to sense the noted parameters during the motion analysis study 250. This sensed information is sent to its corresponding actuator/controller 338 or 342, which is able to telemetrically transmit information, further discussed herein, during this sensor based motion analysis 354.

Each actuator/controller 338 and 342 may either be a passive type device or an active rechargeable battery powered device. If the actuator/controllers 338 and 342 are passive type devices, they may include resonant LC circuits, which will resonate when adjacent generating coils, generate an electromagnetic field, thereby enabling transmission of the sensed information from sensors 340 and 344. An example of such a system is set out in U.S. Pat. No. 6,474,341, entitled "Surgical Communication and Power System," issued Nov. 5, 2002, which is hereby incorporated by reference. Other types of known wireless telemetric systems may also be utilized. Actuator/controllers 338 and 342 may also be battery powered using rechargeable batteries that are either embedded within the implant or positioned remote from the implant and implanted within the patient, similar to known pacemaker technology. These rechargeable batteries may be recharged telemetrically similar to existing pacemaker batteries, as is known in the art.

Figure 15:
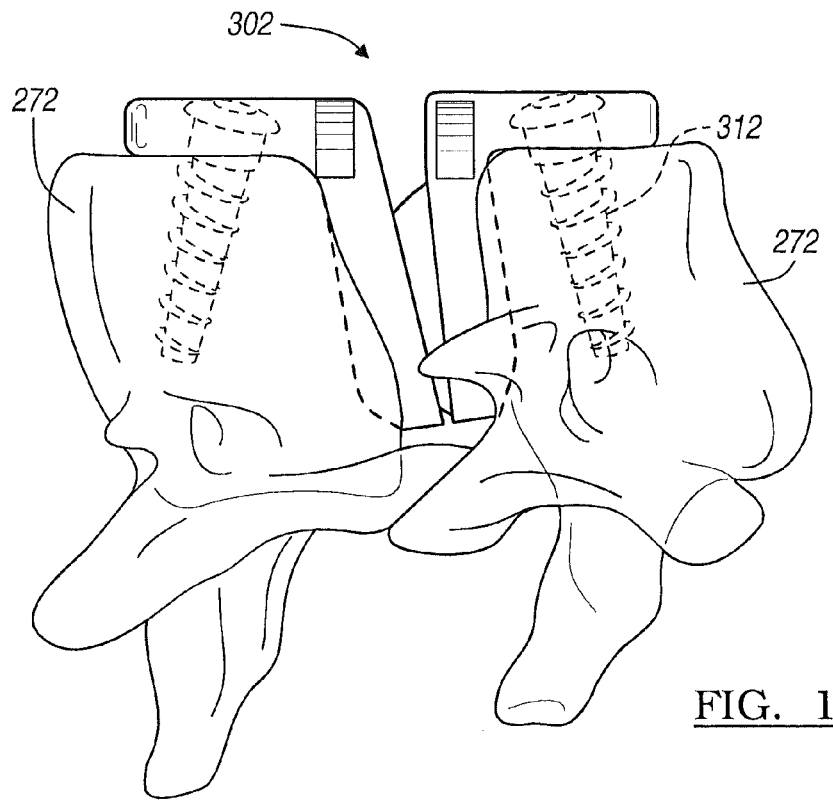
FIG. 15 illustrates an implant of FIGS. 14 and 15 implanted into a spine.

If the system is a passive system, the data may be acquired from the corresponding sensor during the motion analysis study 250 in the post-operative exam 248 during the various motion tests performed on the patient 14. This information is gathered at the time of the study and is used to analyze whether or not further adjustments are necessary to the implant 302. Alternatively, if the system is an active system and battery powered, data may be sampled over time, stored in memory and transferred during the motion analysis study 250 or during other transfer periods, as further discussed herein. With this type of telemetric system, the implant 302 may be adjusted remotely by driving either actuator/controller 338 or 342 to remotely adjust the adjustable set screw 320, via known actuation type mechanisms. Again, while a hinge/set screw adjustment mechanism is shown, any other appropriate adjustment mechanism may be employed, such as worm gears, pinions, etc. Thus, telemetric adjustment 262 may be performed by simply positioning a corresponding transmit and receiving instrument adjacent to the implant site to both receive sensor information and remotely drive the actuators/controllers 338 and 342 to provide remote telemetric adjustment of the implant in a non-surgical manner. By adjusting either the angle 324 or the angle 336, the range of motion, contact, articulating surface adjustments, or other type of adjustments to relieve impingement and increase the range of motion may be performed in a post tuning technique. Briefly, FIG. 15 shows the implant 302 implanted between a pair of vertebrae 272 and aligned, such that the instantaneous center of rotation are properly positioned within the center articulating longitudinal axis Y of the spine (see FIG. 8a).

Figure 16:
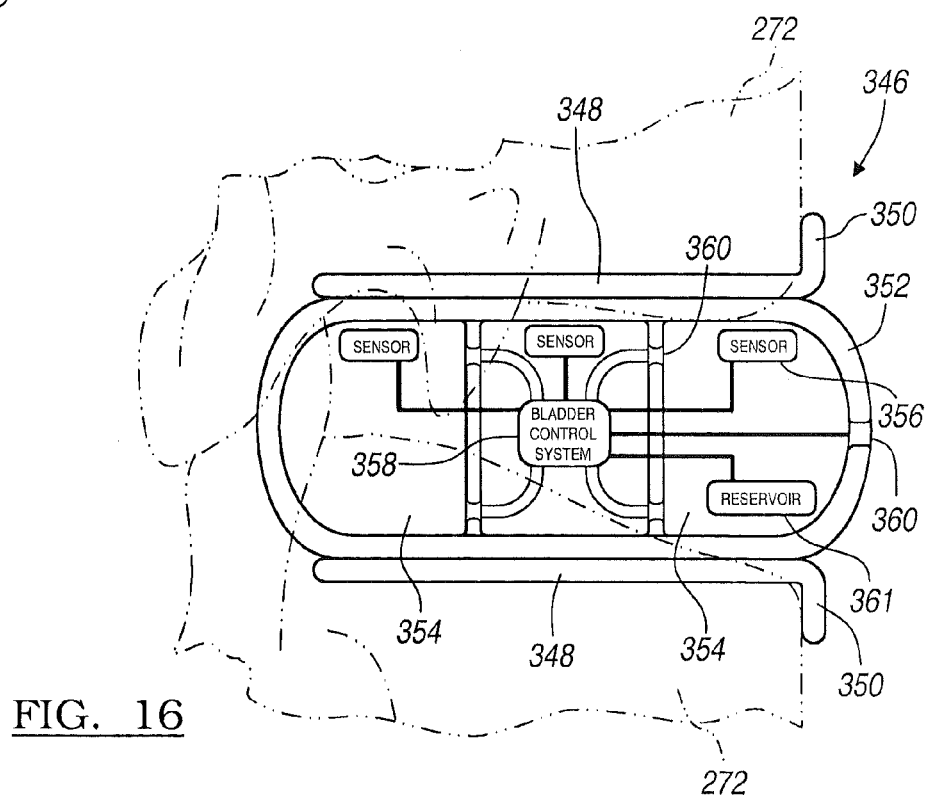
FIG. 16 is a side cross-sectional view of a cervical disc implant according to the teachings of the present invention.

Referring to FIG. 16, another embodiment of a cervical spinal implant 346 is illustrated. The spinal implant 346 is based on the spinal disc prosthesis, set out in U.S. Pat. No. 5,674,296, entitled "Human Spinal Disc Prosthesis," issued Oct. 7, 1997 and U.S. Pat. No. 5,865,846, entitled "Human Spinal Disc Prosthesis," issued Feb. 2, 1999, each of which are hereby incorporated by reference. That is also known as the "Bryan Cervical Disc System," offered by Medtronic Sofamor Danek of Minneapolis, Minn. The spinal implant 346, however, also includes a tuning and adjustment mechanism. The spinal implant includes a pair of rigid support plates 348 and a pair of attachment flanges 350 that define attachment holes to receive bone screws (see FIG. 8g). Positioned between the support plates 348 is a flexible bladder device 352.

In order to provide for either minimally invasive or telemetric adjustment of the implant 346, the bladder mechanism 352 is separated into a plurality of individual bladders 354. As illustrated, the implant 346 includes three adjacent bladders 354. Located within each bladder 354 is a sensor 356 that is used to sense the pressure within each bladder 354. These sensor readings are passed to a bladder control system 358. The bladder control system 358 may again be a passive device or an active battery powered device. If passive, the sensor information will be received during the motion analysis study 250 and adjustment may be performed telemetrically during this study using known telemetric driving devices. If the bladder control system 358 is an active powered system, the system may either operate similar to the passive system or may be an adaptive system that provides real time adjustment for the implant 346. In this regard, each sensor 356 may sense pressure differences in each bladder 354 while the bladder control system 358 attempts to equalize the pressures in the bladders 354 in a real time manner. The bladder control system 358 includes a processor controller 358 and either a battery or known passive driving device. The bladder control system 358 also includes a pump used to transfer fluid retained within the bladders 354 by controlling remote valves 360 and a memory if necessary for storing sampled data.

The implant 346 may also include a reservoir 361 that retains a drug that may be delivered through the external valve 360 and controlled by the bladder control system 358. In this way, controlled drug delivery to the surrounding bone may also be achieved with the implant 346. The drug can include a bone morphagenic protein (BMP) that is able to increase bone density and fusion of broken bones, by delivering the BMP over time to the surrounding infected bones. This drug delivery capability of the implant 346 may be actively delivered if the system is battery-powered, or telemetrically delivered, via an active or passive device during patient exams. Delivery systems may be any appropriate drug delivery system. For example, the drug delivery system may be substantially programmable, such that the drug is delivered according to a preprogrammed schedule from a selected reservoir. Alternatively, the drug delivery system may be substantially wireless, such that the drug is delivered due to a wireless command. Although it will be understood that any appropriate drug delivery system may be used in conjunction with an implant.

In operation, the implant 346 may be used to sense pressure in each individual bladder 354, via the sensors 356 during the post-operative motion analysis 250. With this information, a surgeon can direct the bladder control system 358 to compensate for any abnormalities in pressure in the bladders 354 in order to try to achieve uniform pressure throughout the implant 346. The bladders 354 generally include a saline solution that can be transferred between bladders 354, via the bladder control system 358 and control valves 360. In addition, there is an external valve 360 that may be used to release saline fluid harmlessly into the body to relieve pressure. Alternatively, the external valve 360 may be used to receive additional fluid percutaneously in a minimally invasive way. Thus, the implant 346 may be post-operatively adjusted or tuned, depending upon the healing of the patient, post-operative trauma, or to provide further refinement and increased performance of the implant 346.

Figure 16A:
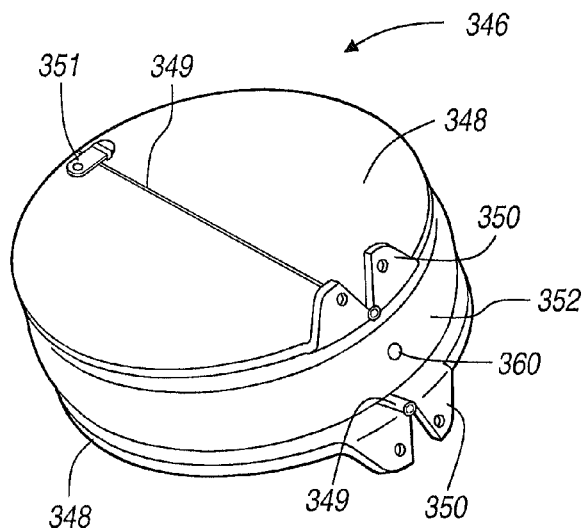
FIGS. 16a-16c are an unfolded and partially folded view of other embodiment of a cervical disc implant according to the teachings of the present invention.
Figure 16B:
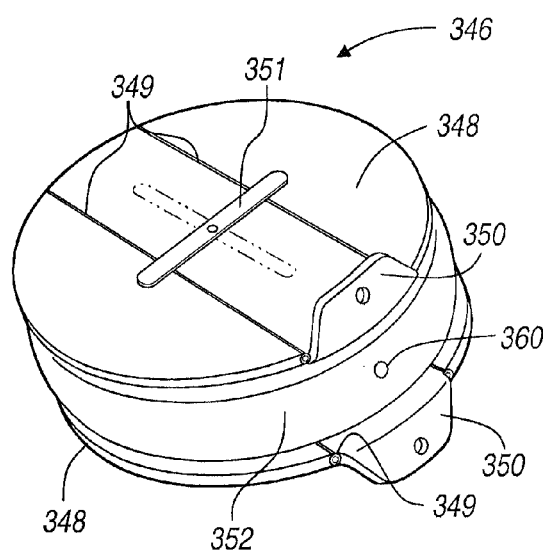
Figure 16C:
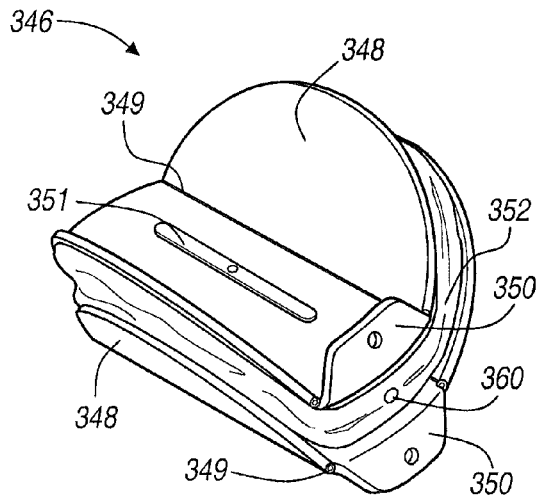

Alternate embodiments of the implant 346 is illustrated in 16a-16c. Here again, like reference numerals are used to identify like structures. The spinal implant 346 is substantially similar to the spinal implant illustrated in FIG. 16, except that the spinal implants illustrated in FIG. 16a-16c are multi-segment implants 346 that allow for a minimally invasive technique and a posterior implantation approach. The implant 346 illustrated in FIG. 16a includes a pair of rigid support plates 348 that include a hinged region 349. This hinged region 369 includes a single hinge that enables the implant 346 to be substantially compressed so that the plates 348 are adjacent to one another. Once adjacent to one another, the plates 348 may be folded via the hinge region 349 creating a semi-circular shape that is significantly smaller than the whole implant 346. This enables the implant to be implanted posteriorly in a minimally invasive manner by simply sliding the folded implant 346 into a small incision and re-assembling or unfolding the implant 346, along the hinge region 349 at the implant area. The hinge 349 also includes a lock 351 that is used to lock the hinge 349 to insure that each plate 348 is locked in a planar fashion. Once locked, the implant 346 is positioned between the adjacent vertebrae 242 similar to that shown in FIG. 16.

Implant 346, illustrated in FIGS. 16b and 16c also includes a hinged region 349 that consists of a pair of hinges positioned on either side of the flange 350. Again, the hinge region 349 enables the end plates 348 to be folded, as illustrated in FIG. 16c to enable a posterior minimally invasive procedure. This implant 346 also includes a lock 351 that rotates to lock the pair of hinges in the hinge region 349 in a substantially planar manner.

Figure 17:
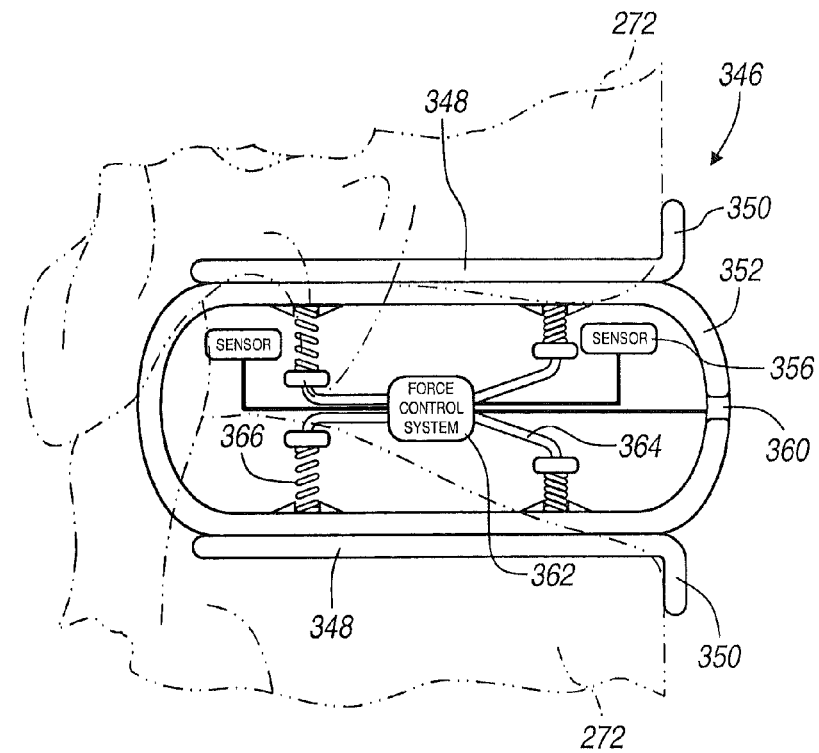
FIG. 17 is a side cross-sectional view of another cervical disc implant according to the teachings of the present invention.

Another embodiment of the spinal implant 346 is shown in FIG. 17, which provides a different type of adjustment mechanism. Here again, like reference numerals will be used to identify like structures. Again, the spinal implant 346 includes a pair of supporting plates 348, a pair of flanges 350 and a support or bladder device 352. Located within the bladder device 352 is a single bladder 354, which can be filled with a saline solution, or optionally not filled with fluid. Again, sensors 356 are located in different regions within the bladder 354 and used to either sense fluid pressure or used as a strain gauge to measure loading forces. The readings from the sensors 356 are read by a force control system 362, which can again either be a passive device or a battery powered active device. The force control system 362 operate similar to the bladder control system 358, except that as opposed to directing fluid between various bladder chambers, it includes force control beams or members 364 that are used to apply a force to the plurality of springs 366 positioned within the bladder 354. By compressing the springs 366 in different quadrants with the control beams 364, tension in the springs 366 are increased, thereby providing additional support within the implant 346. Each spring may be selectively adjusted, depending upon the desired tuning or adjustment necessary. Again, this adjustment is based upon the motion analysis study done during the post-operative exam 248.

The force control system 362 may be used to adaptively or actively adjust the implant 346 if the force control system is an active battery powered system. Alternatively, the force control system 362 may adjust the force within the implant 346 during the telemetric adjustment 262 if the system is simply passive. The bladder control system 358 and the force control system 362 may be formed using conventional micro electronics and mechanical devices or may be formed from micro electromechanical system (MEMS) technology, known in the art.

Figure 18:
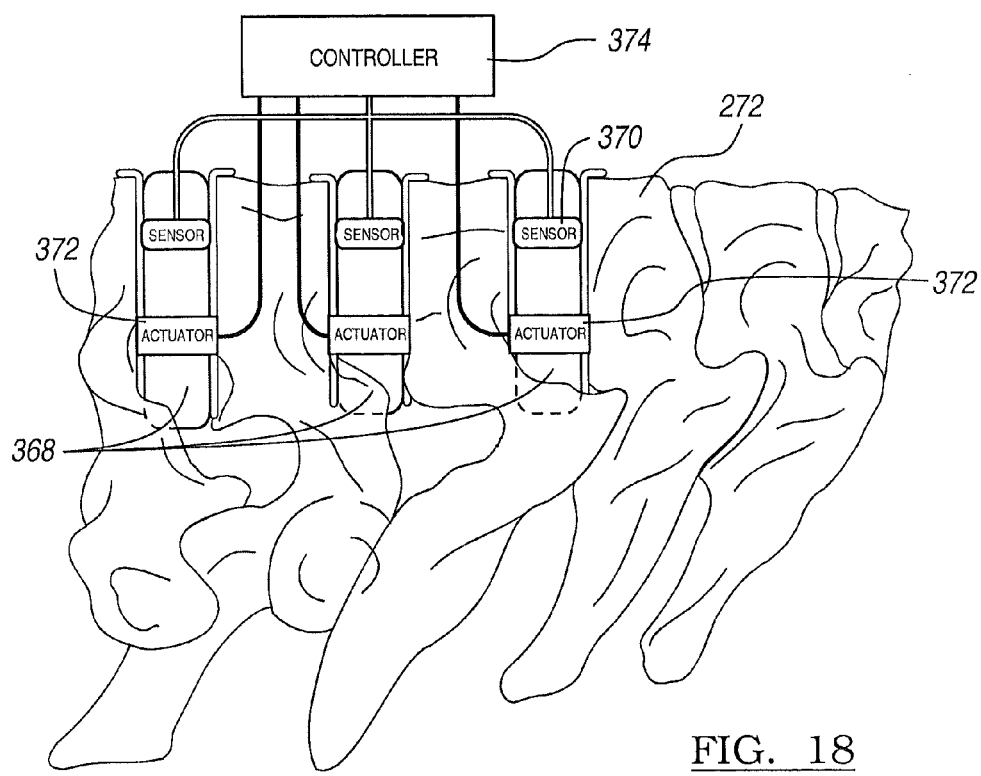
FIG. 18 illustrates a cervical disc system employing multiple cervical disc implants according to the teachings of the present invention.

A multiple segment implantation is illustrated in FIG. 18 that includes multiple implants 368. Each implant 368 may be implanted utilizing the mounting platform 268 and jig 270, as illustrated in FIGS. 11 and 12. Implants 368 may also be implanted using other procedures, such as that shown in FIGS. 8a-8g. Each implant 368 includes a sensor 370 and an adjustment actuator 372, similar to that shown in FIGS. 14, 16, and 17. However, each implant 368 is controlled and actuated, via an active rechargeable battery powered external controller 374. Optionally, each implant 368 may include its own individual internal controller 374 that can communicate to the other implants 368, via a wireless or wire connection. Alternatively, a single internal master controller 374 may be positioned within one of the implants 368, which is used to control and drive the remaining implants 368 in a master/slave relationship.

Controller 374 is used to sense various parameters again, such as temperature, pressure, etc. where actuators 372 are used to tune or adjust each implant 368 accordingly. The controller 374 may be implanted adjacent to the spinal region, similar to a controller and battery for a pacemaker. The multiple segment implantation with each implant 368 communicating with the other surrounding implants 368 enable real time adaptive control of this spinal region, such as the cervical spinal region of the patient 14. In other words, the controller 374 may sense, via the sensors 370 whether any one of the implants 368 is under too much pressure or one may be too laxed and adjust accordingly, depending upon the patient's movements. In this regard, when the patients at rest, extra support between the vertebrae 272 may not be necessary. However, when the patient 14 is doing physical activities or exercise, additional support may be necessary between each vertebrae 272 and each implant 368 may be expanded during this period in an adaptive manner. Alternatively, the controller may again simply be a passive controller or an active controller and used to send and receive information, as well as adjust the implants 368 during the post-operative exam 248, via the telemetric adjustment 262.

Figure 19:
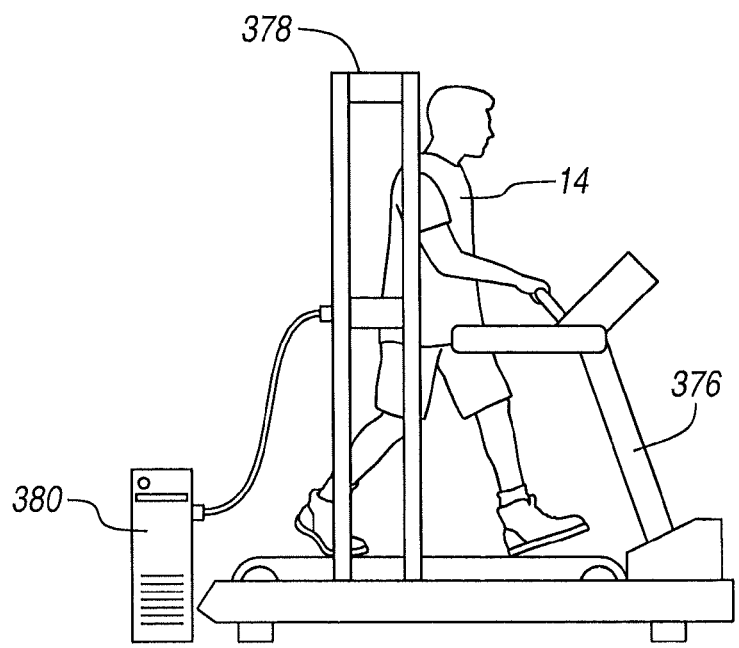
FIG. 19 illustrates a transmit/receive module used during the motion analysis study of a patient according to the teachings of the present invention.

Turning to FIG. 19, an exemplary telemetric system used for performing the motion analysis 250 is illustrated. In this regard, the patient 14 may undergo the motion analysis 250 by exercising on a treadmill 376. The treadmill 376 is positioned within a transmit/receive module 378. When the patient 14 is positioned within the transmit/receive module 378 and exercising on the treadmill 376, information can be collected from the particular implant during the motion analysis 250 using the sensor based 252 data analysis, via the telemetric adjustment 262. In other words, the transmitter/receive module 378 includes signal transmitters and receivers to either actuate a passive or active controller to receive sensed information. This information is forwarded to a control processor 380 where the surgeon can analyze the collected sensed data. Once the data has been analyzed, the controller 380 is used to actuate the transmit/receive module 378 to adjust one or more implants in the patient, via the control actuator circuits, disclosed above. It should also be noted that an imaging device may also be positioned adjacent to the patient 14 while the patient is on the treadmill 376 to provide both an image-based and a sensed-based motion analysis 250, as previously discussed.

Figure 20:
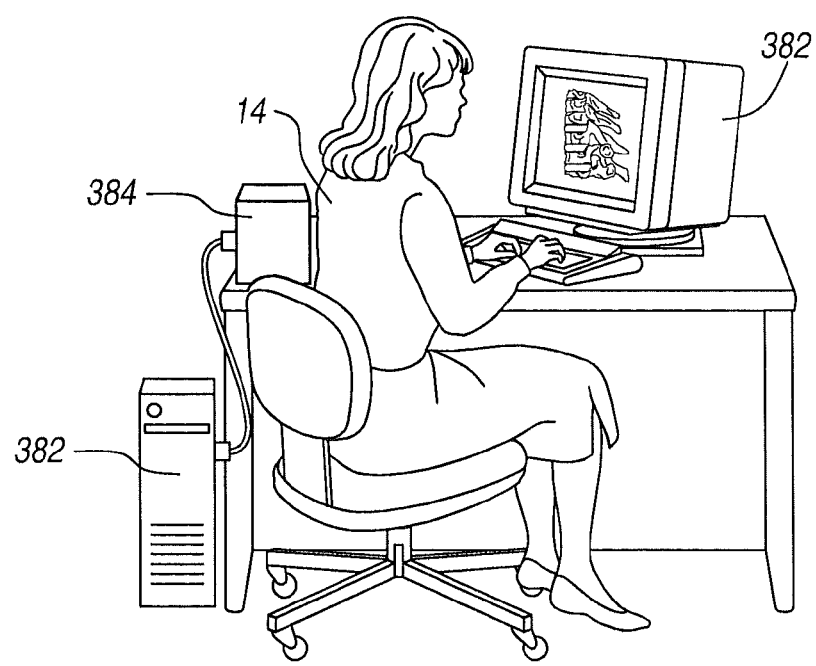
FIG. 20 illustrates a home based transmit/receive module used for a motion analysis study according to the teachings of the present invention.

Referring now to FIG. 20, another telemetric system used to transmit motion analysis information to the doctor is disclosed. With this technique, the patient 14 can simply conduct a self analysis by positioning him or herself adjacent to a computer 382. Attached to the computer 382 is a transmit/receive module 384. The transmit receive module 384 operates similar to the transmit receive module 378, except that the patient 14 can simply run through a set of suggested motions, while the transmit receive module 382 telemetrically receives information from the implant positioned within the patient 14. This information can be transmitted, via the computer 382 online to a receiving hospital or doctor's office. The doctor may then analyze this information, make a recommendation to the patient 14 whether the patient 14 should come in to the office for a telemetric adjustment 362 of the patient's implant. Alternatively, the doctor may also simply instruct the transmit control module 384, via the computer 382, to perform the telemetric adjustment of the patient 14 in the patient's home.

The procedure 230, as well as the associated implants, systems and instruments, enables both pre-operative and post-operative review and analysis. Additionally, post-operative tuning of the implant may also be achieved without requiring revision surgery or highly invasive types of procedures. In this regard, either minimally invasive or telemetric adjustments of the implants may be achieved.

As discussed briefly above, with reference to FIG. 10, an analysis of data in block 240 can be performed prior to selecting an implant or procedure in block 243 and implanting an implant under surgical guidance in block 244. As discussed briefly above, various considerations can be used when selecting an implant and a procedure in block 243. For example, the abnormalities to be corrected, a selection of implants or grafts to fix the abnormality and various procedures to resolve an abnormality may be considered together or individually. Therefore, it will be understood that a plurality of substeps or steps may occur when selecting the implant/procedure, such as briefly described in block 243 and implanting an implant under surgical guidance as in block 244.

The following description may be a separate procedure or may be understood to be any part of the procedure 230 and particularly included within block 243 and 244, regarding selecting an implant and implanting an implant under surgical guidance 243, 244. It will be further understood that although the following discussion may relate generally to a disc or nucleus replacement or implant, that any appropriate implant or procedure may be used. For example, the procedure and systems may be used to plan and select a procedure for any appropriate abnormality such as a humeral head or stem abnormality, a knee abnormality, a shoulder abnormality or any other abnormality. Therefore, the planning and implantation of the disc or nucleus is merely exemplary and not intended to be limiting.

Figure 21:
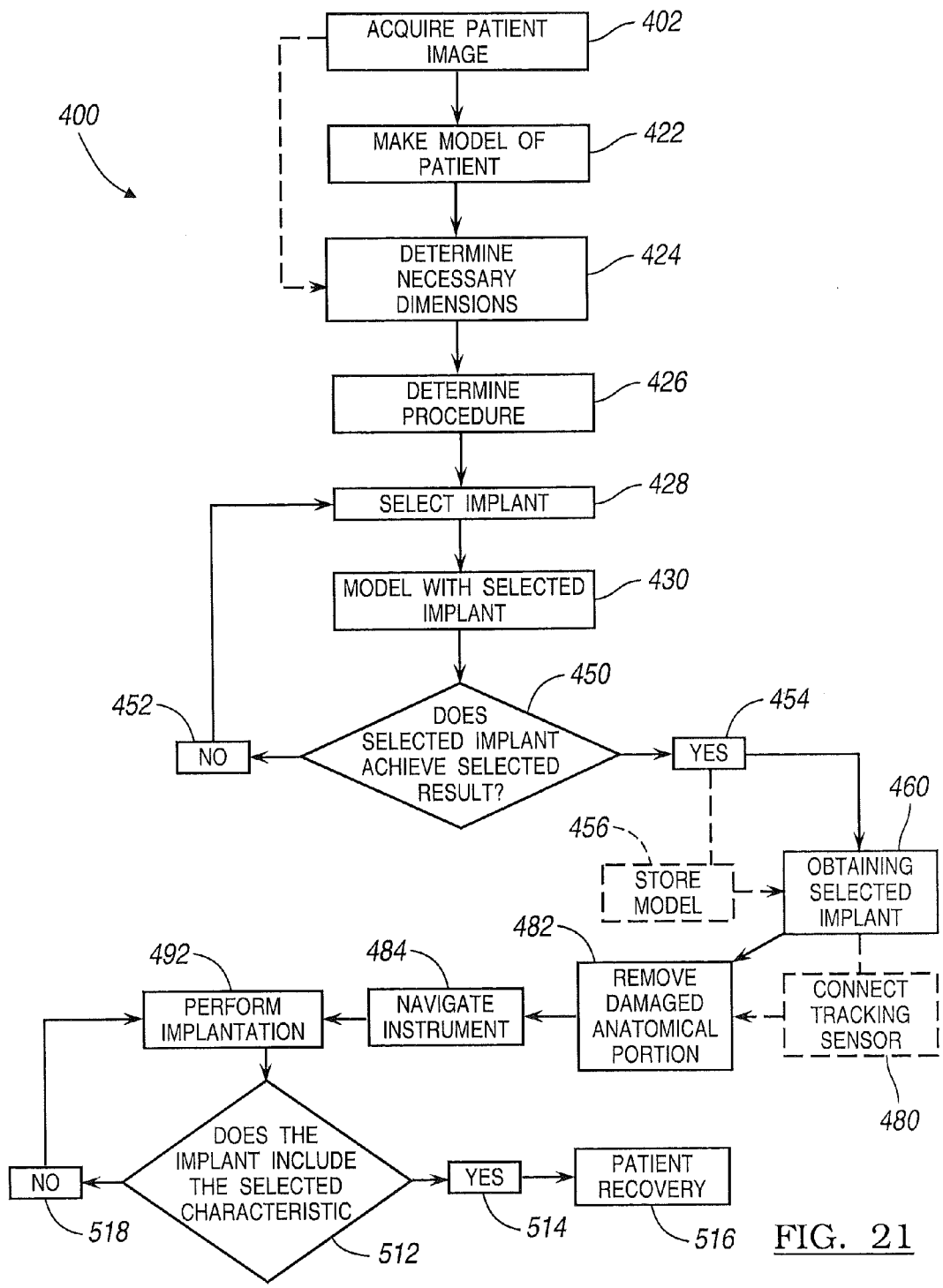
FIG. 21 is a diagrammatic representation of a method according to various embodiments of planning a procedure.

With reference to FIG. 21, a method of selecting an implant and procedure, such as in block 243 in FIG. 10, is illustrated in diagram or method 400. Briefly, the method 400 may also be referred to as a planning system or software that may be used to select an implant and procedure for assistance in resolving or in improving abnormality of the anatomy. The planning system may include software integrated into the workstation 36 for planning a procedure and selecting an appropriate implant for the patient.

Broadly, the system 400 can assist a surgeon or user in making judgments regarding a selected implant, such as size, geometry, volume and the like and performing a procedure to achieve a result once the selected implant is positioned. For example, the system and method may assist a surgeon in removing a selected amount of tissue before placing an implant relative to the anatomy. Determining a substantially precise amount of tissue to be removed may assist in performing a procedure within fairly strict boundaries such that it may be helpful to achieve a selected outcome that may be most preferable for a patient.

In addition, the method may assist in selecting an implant that most precisely meets a predetermined size, shape, and other requirements to assist a patient. For example, for a motion preserving device, such as a nucleus, prosthetic disc, femoral implants, knee implants, or the like, substantially precise placement and preoperative planning may be used to increase the effectiveness of the implant. Therefore, various image gathering techniques and devices can be used to assist a user, such as surgeon, in selecting an implant for a procedure and ensuring that a patient is substantially prepared for the procedure. This preparation and planning may ensure that the most appropriate implant is selected and precisely placed for completing the procedure. Therefore, using various navigation systems and techniques and image acquisition systems may assist in substantially precise planning to assist in a procedure. The parameters that may be considered include the type of implant, implant shape or geometry, implant size, placement and kinematic analysis of proposed implants.

The method 400 starts at block 402 by acquiring a patient image. The patient image may be acquired in any appropriate manner, either a time before the operative procedure or during the operative procedure, as in an operating room prior to performing a surgical procedure on any portion of the patient. For example, as discussed exemplary herein, the images may be acquired of the patient prior to removing a selected portion of the spinal column, such as a nucleus or a disc. Therefore, the acquired images of the patient in block 402 are generally of the patient in a preoperative or natural state. The images may be acquired with the patient in any appropriate manner. For example, the images may be acquired using a MRI, a CT scan, x-rays, fluoroscopic C-arm, ultrasound or any other appropriate method including imaging methods discussed above. Therefore, it will be understood that the images may be collected in any appropriate manner.

The images may be collected to be displayed on the display 10, or any appropriate display, prior to and during an operative procedure. The display 10 may be connected to the work station 36 for use during an operative procedure. In addition, the display 10 may be connected to a different work station for different portions of the procedure. For example, the work station 36 may be provided for an operative procedure to ensure that the planned procedure occurs and for navigation. Nevertheless, a different work station may be provided for the planning of the procedure, as described herein and the procedure and images stored for later use. It will be understood that various images may be acquired of the patient to allow for modeling and planning of a selected procedure as discussed herein.

Figure 22:
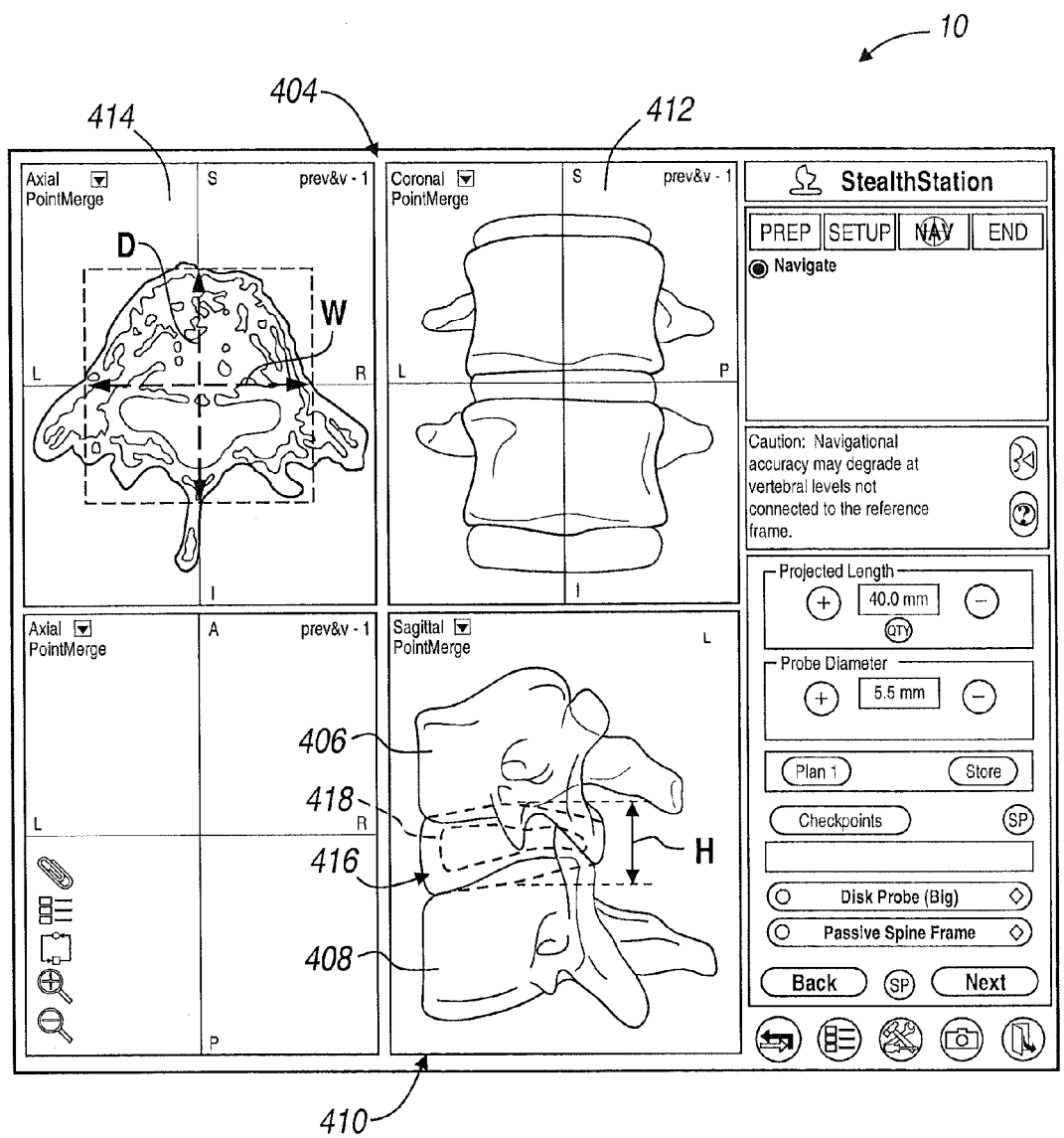
FIG. 22 is a view of a display including a model of a portion of an anatomy for planning a procedure.

With additional reference to FIG. 22, the display 10 may first display a preoperative or planning screen 404. The preoperative or planning screen 404 may include a plurality of images that may be different depending upon a selected procedure. For example, in a spinal procedure, the preoperative display screen 404 may include a plurality of images including a first vertebrae 406 and a second vertebrae 408. The images may include a sagittal plane view 410, a coronal plane view 412 and an axial view 414. The various views may allow for a substantial visualization of an area of interest such as a selected disc 416 that may include a nucleus 418.

The disk 16 may include an annulus which surrounds the nucleus 418. This difference between the annulus and the nucleus may be a difference in the viscosity of the materials or rigidity of the materials. Generally, the annulus surrounding the nucleus 418 may be substantially more rigid or less fluid than the nucleus 418. Therefore, it will be understood that an implant to replace either the annulus of the disk 416 or the nucleus 418 of the disk 416 may include similar properties or may be cured, such as with materials, time, radiation and the like, to achieve selected properties.

During the preoperative stages, the various images may be achieved by obtaining a plurality of images of a patient, such as through various known methods and any appropriate method. In addition, the views may include models, such as a multi-dimensional model or 3-D model, of the selected portion of the anatomy. Therefore, various images, such as plurality of CT, MRI or X-ray images may be used to create the various views 410-414 and may be also used to create two, three, or other dimensional models of the area of interest or an atlas model may be used as well. The various models or images formed of the models may also be used for aligning or selecting an implant during an implant procedure. For example, the models may be moved and the implant aligned along the plurality of planes, such as the coronal or sagittal plane and any other appropriate view, such as an axial view. Alternatively, no model may be made and simply the two, three, or four dimensional images or image data acquired may be used for planning and carrying out the procedure.

These various views and models may allow a user, such as physician, to determine various dimensions of selected areas such as the disc 416. Therefore, the physician may be able to measure a distance H that may include a height of the disc 416. Various other measurements such as width W of the disc 416 and depth D may also be measured. These measurements may be found due to various modeling that allows for a coordinate system including at least three axes, X, Y and Z. This may allow a physician to determine a selected volume of the disc 416. A volume of the nucleus 418 may also be determined using these or other various measurements. In addition, the model may be used to precisely determine a plurality of measurements, greater than the height, width, and depth of the disc 416 to precisely determine a volume of the nucleus 418. Alternatively, as discussed herein, a template program may be used to position an image relative to the models or image data of the patient to determine various dimensions. Therefore, the preoperative images may be used to determine a selected size or shape of a portion of the anatomy.

In addition to determining a selected size, geometry, volume, and dimension or other size characteristics, a user may also determine various other characteristics of the anatomical portion or an implant to replace the anatomical portion. For example, the user may determine that a selected viscosity of rigidity of the implant may be positioned in the area determined in the planning screen 404. For example, an user may determine that a selected viscosity is required to provide an implant to replace the nucleus 418. As discussed herein, during the planning stage the user may also determine an amount, type, duration and other specifics to cure a selected material to achieve various characteristics of material to achieve a planned procedure. These determinations may be provided with kinematic analysis performed by the workstation 38.

It will be understood that although the display 10 exemplary includes a view of the spinal area that any appropriate portion of the anatomy may be imaged. For example, a proximal portion of a femur may be imaged to determine a volume of a femoral head and intramedullary canal for various procedures, such as a femoral head implant. Therefore, it will be understood that acquiring a patient image in block 402 may be used to acquire any appropriate image of the patient and an image of the spine is merely exemplary.

With reference to FIGS. 21 and 22, as discussed above, the images acquired in block 402 may be used to form the model of the patient in block 422. This model may be two, three, or four-dimensional model, as discussed above, and may be placed in a coordinate system and can be used to determine a plurality of dimensions and volumes in block 424. The dimensions and volumes, including height H, depth D, width W, and volumes of selected portions, such as the nucleus 418, may be determined by positioning a navigable probe or instrument such as the probe 62 relative to selected portions of the anatomy such as the disc 416 or the vertebrae 406, 408.

In addition, various reference frames may be attached to selected portions of the anatomy, such as the dynamic reference frame 54. In addition, separate dynamic reference frames may be affixed to the vertebrae 406, 408 to allow for a dynamic determination of the real time position of vertebrae 406 relative to the vertebrae 408 and vice versa. Also, various fiducial markers or anatomical landmarks may be used to reference the anatomical portions for registration, as discussed above, such as the vertebrae 406, 408, in the system.

Alternatively, the images or models positioned in the coordinate system may be used to relatively determine sizes. Therefore, the measurements may be substantially precise in determining the various dimensions and volumes of the selected portions of the anatomy. The dimensions determined in block 424 can be known to be substantially correct due to the actual image data acquired of the patient to form the digital model of the anatomy in question.

The image produced on the planning screen 404 may be used to model the anatomical portion with a selected implant or with a selected anatomical motion. The model of the anatomical motion may assist a user in selecting an appropriate implant to achieve a desired or selected anatomical motion. Therefore, it will be understood that the images and planning screen may be used to plan a plurality of characteristics for an implant or procedure as discussed herein. The system and method 400 may be used to determine a selected size, geometry, type of implant, position, physical characteristic including viscosity and malleability and other appropriate characteristics. It will be understood, therefore, that those characteristics discussed herein are merely exemplary of the characteristics that may be planned and selected using the system 400.

With reference to FIG. 21, it will be understood, however, that forming a model is not necessary. Although a model may be useful to assist in navigating and planning a procedure, the image data alone may be sufficient to perform the procedure. The image data may be used to determine or select an implant to achieve a selected result by substantially matching or providing a dimension of the anatomical portion with an implant or procedure.

The dynamic reference frames may be any appropriate type such as optical, acoustic, electromagnetic, and the like. It will be understood that any appropriate dynamic reference frame may be used. It will also be understood that a dynamic reference frame may not necessarily be used if the portions of the anatomy are substantially fixed relative to one another. The images on the display 10 may be referenced with an instrument, such as the probe 62, and the relative spatial positions of the various portions of the anatomy are then known as long as the portions of the anatomy do not substantially move relative to one another. Therefore, dynamic reference frames may not be necessary, but may be used to assist in tracking the real time position of the patient during the surgical procedure, further discussed herein.

With reference to FIG. 21, once the dimensions are determined in block 424, a procedure may be determined in block 426. Again, although a selected portion of the spine, including vertebrae 406 and 408, are illustrated in the display 10 any appropriate portion of the anatomy may be modeled in block 422 and dimensions thereof or relative thereto are determined in block 424. Therefore, although a procedure may be determined relative to the vertebrae 406, 408, any appropriate procedure may be determined in block 426. Nevertheless, the procedure determined in block 426 may include preparing the disc 416, replacing the disc 416 with a prosthetic disc, or replacing the nucleus 418 with a prosthetic nucleus. Any other appropriate procedure may be determined in block 426, such as fusing various vertebrae, such as the vertebrae 406, 408 in the spine. A medication or material may be provided, such as a bone morphogenic protein (BMP), when fusing selected vertebrae of the spine. The material may be provided during the procedure or after the procedure, such as being released from the implant. In addition, the model formed in block 422 and the dimensions obtained in block 424 can be used to verify the appropriateness of a procedure for a patient. The method 400 may be used to confirm a procedure that was pre-selected. The models and the implant dimensions that may be modeled can confirm the appropriateness of the selected procedure.

Determining a procedure in block 426 may also include determining exactly what will occur during an operative procedure. In addition, it may also include determining the amount of tissue to remove, determining an amount of resection, determining a substantially ideal distraction height, and the like. For example, if it is determined that the nucleus 418 must be removed or replaced, determining the procedure in block 426 may also include determining the volume of the nucleus 418 to be removed and from where. Therefore, if the volume of the nucleus to remove is about 10 cc, this may be determined by determining the procedure in block 426. The exact amount may be determined because of the dimensions taken in block 424 using the model formed in block 422. An exact amount of removal may also assist in achieving a selected result. The procedure may include a selected volume of material removal and the selection and positioning of an implant may substantially rely on material removal. Therefore, the tracking and planning system and method allows for a substantially pre-operatively chosen resection plan and implant.

Figure 24A:
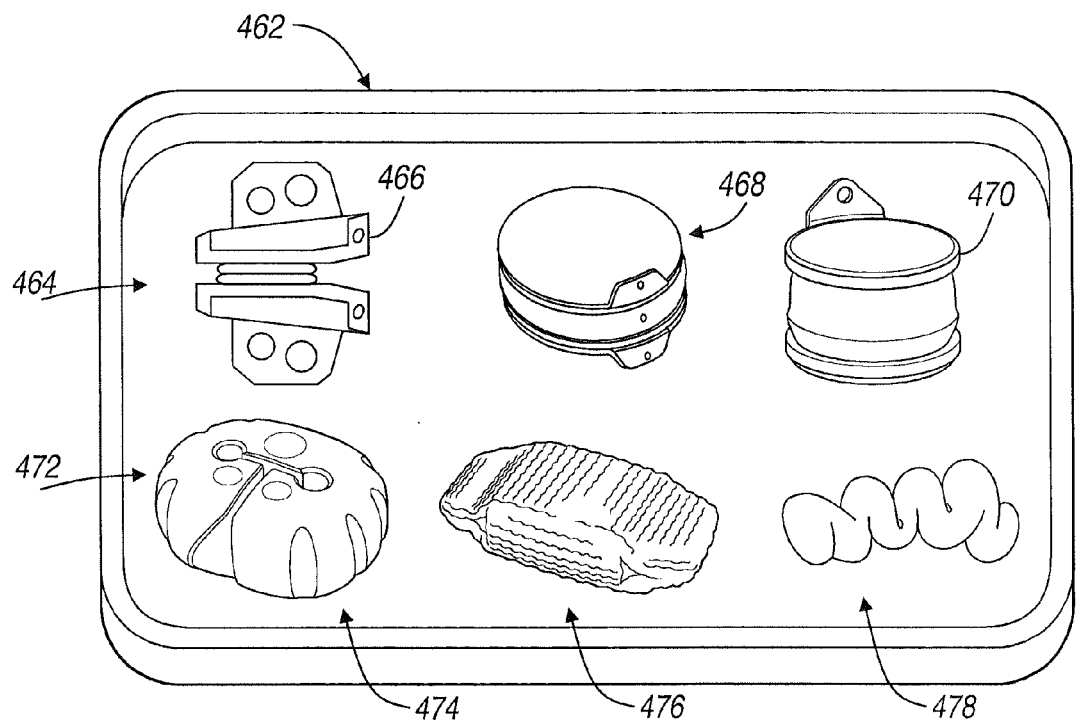
FIG. 24A is a plan view of an exemplary implant kit.

Once the procedure is determined in block 426, an implant may be selected in block 428. Selecting the implant in block 428 may include selecting an appropriate type of implant, selecting an appropriate size of an implant, including a volume, size, geometry and other appropriate considerations and confirming that the implant may achieve selected results from the patient. These results may also include kinematic studies based on using a selected modeled implant. It will be understood that a kit 462 (FIG. 24) may be provided having a plurality of implants from which an implant may be selected to perform the procedure selected in block 426. Alternatively, an implant may be substantially custom designed for the procedure determined in block 426. Therefore, the implants may be preformed or formed after determining the procedure in block 426 to achieve selected results.

If the kit 462 includes a plurality of known implants, including a known size, shape, geometry and other known characteristics, the implant may be modeled in the images from the patient in block 430. Therefore, the implant selected in block 428 can be modeled with the model made in block 422 and block 430. Because the dimension and size of the implant selected in block 428 is known, it can be positioned in the model of the patient formed in block 422 to ensure that the selected implant will achieve a selected result. It is generally known in the art to provide selected algorithms in computer programs to provide for dynamic, kinematic, or static modeling of a selected portion of the anatomy to ensure that a result is achieved.

Also, an implant may be modeled in block 430 that has been digitally augmented or digitally created to achieve a selected result. Therefore, a template or general sizing program may be provided. The work station 36 may be able to operate the template program which includes a plurality of template shapes, sizes, geometries and volumes to form the implant selected in block 428 which can be modeled in the anatomy in block 430.

Figure 23:
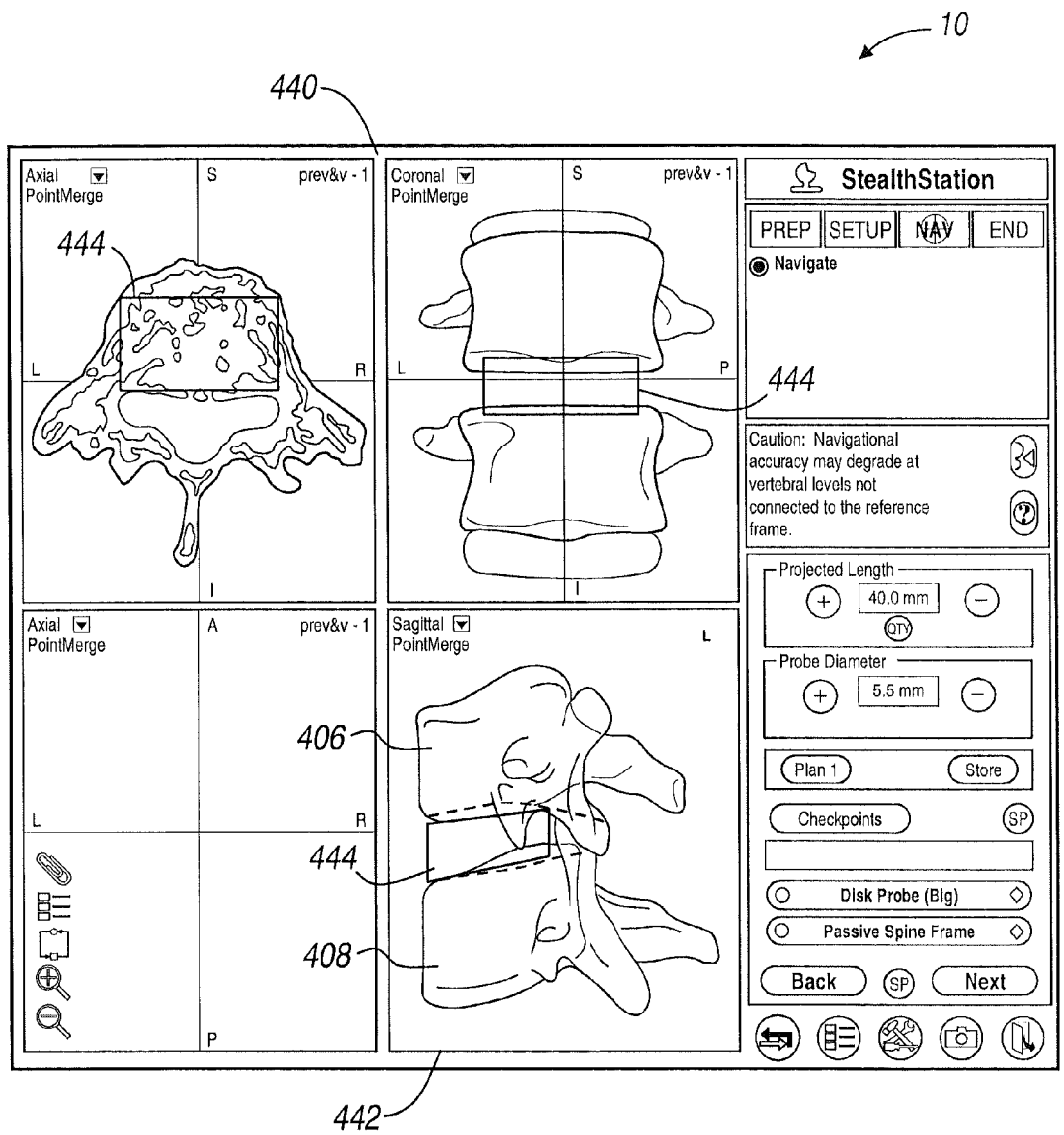
FIG. 23 is a view of a display including a model of a portion of an anatomy for planning a procedure with a template sizer program.

For example, with reference to FIG. 23, the display 10 may include a plurality of views of the anatomy substantially similar to the plurality of views of the anatomy of a display 10 including the screen 404. Here a screen 440 may include a display of a selected portion of the anatomy including a template program. With reference to a sagittal plane view 442, a template shape, such as a square 444, may be illustrated relative to the vertebrae 406, 408. Because of the modeling, various dimensions of the template shape 444, such as height, width, depth, volume and other appropriate dimensions may be known, changed and/or adjusted. The template shape 444 may be moved, sized, and the like by a user, such as a physician, to achieve a selected fit between the vertebrae 406, 408. Once the physician has determined that a selected or desirable shape and size has been achieved, the dimensions of the template shape 444 may be known due to the fact that the model has been substantially rendered and determined in three dimensions. This modeling with the template shape 444 can also be used to determine precise dimensions, such as volume, geometry, size, and the like as discussed above.

The template 444 may also be any other appropriate program. For example, the template 444 can be a portion of the program that allows for computer aided designing of an implant. In addition, relatively more simple drawing programs can be used to draw an implant to form the template shape 444 that may be used to later define an implant for the spine. That is the template program 444 or template design may be any portion of a program that allows a user, such as a physician, to model a selected portion of the anatomy, such as the selected position or removal area of the disc 416 for selecting and/or designing an implant to be used in the procedure. In addition, various implants may be imaged and positioned in the system to be used as the template program 444. Regardless, it will be understood that any appropriate method or program may be used to define the template 444 for defining and selecting an area of the anatomy for an implant or designing an implant.

Therefore, the generic template 444 may be sized on the display screen 440 to meet a selected result to allow for choosing a non-pre-saved implant. In addition, the template shape program 444 may be used to form a substantially custom implant for implantation into the portions of the anatomy. It will be understood that the template shape 444 as a part of a template program can be used to determine a size and model it in block 430 to determine whether the template shape dimensions and sizes 444 may be used to achieve selected results within the patient. Also, any appropriate shape may be used including oval, spherical and others. Moreover, the shape need not be uniform, but may include a unique geometry. The shape may also be used to determine the volume of tissue to be removed, as well as from where the tissue should be removed.

In addition to the template shape program 444, a non-saved implant shape may be substantially real-time modeled into the work station 36. Briefly, an implant may be referenced or shaped defined with an instrument. For example, the probe 62 may be used to touch a plurality of points on the non-saved implant to determine a plurality of points in shape relative to the implant. The plurality of points can then be integrated using the work station 36 to substantially model the non-saved implant shape within the work station 36 such that the real time model implant can be modeled in the block 430 to determine whether it will meet the determined procedure in block 426.

In addition, an implant may be modeled using a plurality of methods, such as an MRI, a fluoroscopic imaging device, and the like. In an intraoperative procedure to form a model of the implant that may then be positioned relative to the images on the screen 10. Therefore, rather than having the work station 36 model the implant from a plurality of points determined with the probe 62, the work station 36 may model the implant using image data captured by selected imaging devices. Even other imaging devices, such as a scanner, including a three-dimensional scanner, and the like may be used to scan the image of an implant.

Therefore, it will be understood that all types of implants may be used in the method 400. Implants using predetermined dimensions may be modeled in block 430 as may be a general template program shape 444 and a substantially real time shape determined implant. The method 400 may be substantially used with any appropriate implant or procedure. Similarly, it will be understood that known implants, sizes and dimensions, template shapes and real time determined implants may be used for a plurality of procedures in addition to a spinal procedure. For example, knee portions, femoral portions, humeral portions and the like may also be modeled in block 430 with a selected portion of the anatomy.

Once the implant has been modeled in block 430, it can be questioned in block 450 whether the model implant modeled in 430 achieves the selected results or characteristics. If the answer is No in block 452, the selection of the implant can be reselected in block 428 and then remodeled in block 430. Therefore, it will be understood that the selection of the implant may be iterated until the selected implant achieves the selected results or characteristics and the answer is Yes in block 454. The decision can be determined either by the surgeon doing the procedure, or the processor, either in the workstation 36 or other processor, can assist in its determination based upon running known anatomical kinematic modeling.

The processor in the workstation 36 can be used to determine an implant that may best relieve the modeled abnormality. For example a plurality of similar procedures may be saved such that the processor may determine a possibility that a previously used implant may achieve a similar result in the instant situation. For example, the system may suggest a particular implant based upon the size of the patient and a previously performed procedure with a patient of similar size. Moreover, the processor may use the modeled patient and the known implant dimensions, types, etc. to replace a selected volume or tissue or achieve a natural or selected kinematic motion.

A plurality of implants may be provided to be modeled in block 430. The plurality of implants may assist in assuring that a substantially selected outcome is achieved. The selection may be substantially reduced due to determining the procedure in block 426 and selecting an implant to substantially achieve the procedure in 428. In addition, it will be understood that each of these steps to block 456 may be performed substantially preoperatively. The images of the patient may be obtained in block 402 and the model made of the patient in block 422 may be performed substantially before the patient ever reaches an operating room. Therefore, known and unknown implants may be modeled in the patient model in block 430 to determine whether a selected result can be achieved in block 450. That is, known implants can be modeled in the model in block 430 or the template program 444 can be modeled in the patient in block 430 to ensure that the implant selected during the procedure may achieve a selected result. Nevertheless, it will be understood that the modeling may occur substantially intraoperatively to assist in assuring that the implant selected for implantation may achieve the result without later confirmation or that later confirmation may substantially ensure achievement of the selected result.

Nevertheless, once the implant has been selected in block 428 and it has been determined that the implant will achieve selected results in block 450 and the Yes determination block 454 is achieved, the procedure of implanting the implant may proceed.

In selecting and determining an appropriate implant, it will be understood that various models, both static and dynamic, may be created. Any of these models may be optionally stored in block 456. That is, the models may be electronically stored in the work station 36 or may be stored in a substantially permanent form, such as printout. Nevertheless, the model that may be stored in block 456 may be used in assisting a physician during an operative procedure. As discussed herein, the stored models may assist a user, such as physician, in ensuring that an appropriate positioning of the implant has been obtained and that an operative procedure has been successful in implanting the implant. Moreover, by storing and identifying the proper implant for a particular shape and size patient, the method or system 400 may also suggest an appropriate size implant based upon the pre-acquired image data and upon storing and identifying the implants to the particular size patients. In this way, the selection process may be quicker by saving or providing implants that are initially suggested that are very close to the proper size and shape.

Regardless, it will be understood that the steps 402-456 of the method 400 may occur substantially preoperatively. That is, the images may be acquired of the patient in block 402 and the various models and testing performed to select an appropriate implant and procedure for the patient. This may be done prior to the patient being brought to an operative theater and may reduce trauma to the patient and time in the operating theater. It may also reduce the time of the operative procedure to decrease time of healing and increase post-operative return to a normal life of the patient. In addition, it will be understood that each of the steps may occur during an operative procedure. Even during the operative procedure, the planning and selecting of a particular procedure and implant may reduce the time of the operative procedure, for example, in place testing and trialing may be reduced due to the preoperative modeling of the implant.

Whether or not the planning and modeling occurs pre or intra-operatively, the procedure may proceed to implanting the implant in the patient. Similar to block 244 in FIG. 10, the implant may be implanted with surgical guidance. It will be understood that the implant may be implanted in any appropriate manner and need not be guided using any appropriate mechanism, but navigation of various portions may be provided. Nevertheless, it will be understood that the procedure may be substantially guided to assist in performing the operative procedure.

As described herein, each of the instrument for removing or resecting selected anatomical portions, the instrument for positioning or implanting the implant, and the implant itself may be substantially navigated or tracked using appropriate mechanisms. For example, tracking sensors may be affixed to any of the appropriate portions (FIG. 24B) and the tracking sensors may include acoustic, optical, electromagnetic, radiative and the like to be tracked by a tracking array to determine a position of any portion of the assembly. For example, a probe or instrument may be tracked which may position a selected implant, such as a nucleus implant, to assure that the nucleus implant is positioned in a selected position. If the nucleus implant includes a curable material, such as with UV curing, the UV source may be tracked as well to ensure that a selected portion of the material is irradiated with the UV radiation. Therefore, it will be understood that substantially all portions of removing, implanting, and curing selected implants may be navigated. In addition, the positions and properties or characteristics of the implant may be substantially confirmed, as discussed herein, using various tracking sensors.

With reference to FIG. 21, generally the operative procedure may begin by obtaining the selected implant in block 460. With additional reference to FIG. 24A, the exemplary implant kit 462 may be provided either pre- or intraoperatively. The kit 462 may include a plurality of implants from which a selected implant, such as the selected implant selected in block 428 may be selected. The kit 462 may include a plurality of types and sizes of implants. For example, the kit 462 may include a plurality of disc prosthesis 464. For example, the prosthesis may include a disc prosthesis such as a Maverick™ 466, a Prestige™ 468, or a Brian™ 470 offered by Sofamor Danek of Memphis, Tenn. These various types of disc prosthesis 466-470 may also come or be obtained in a plurality of sizes depending upon the selected implant selected in block 428. Furthermore, the kit 462 may also include a plurality of nucleus implants such as an implant described in U.S. Pat. No. 6,620,196 entitled "Intervertebral Disc Nucleus Implants and Methods"; U.S. Patent Application Publication No. 2003/0023311 entitled "Intervertebral Disc Nucleus Implants and Methods: and U.S. Patent Application Publication No. 2003/0199984 entitled "Intervertebral Disc Nucleus Implants and Methods"; the disclosures of each incorporated herein by reference. The implant 474 may be used to replace a selected volume of the nucleus 418. It will be understood that other nucleus prosthesis or implants may be provided such as a prosthesis 476 which may be known as the PDN™ by Raymedica, Inc. of Bloomington, Minn., and described in U.S. Pat. Nos. 5,674,295; 5,824,093; 6,132,465; and 6,602,291, each is incorporated herein by reference.

Figure 24B:
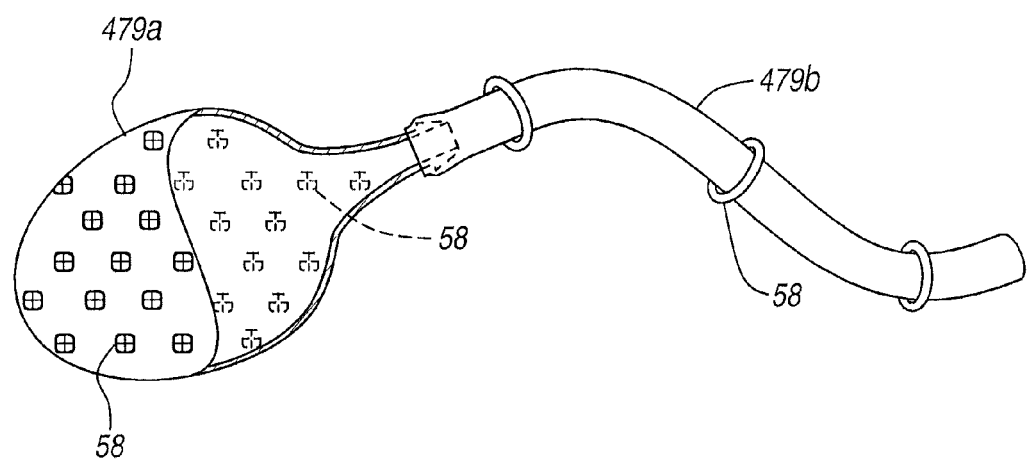
FIG. 24B is a plan view of an implant according to various embodiments that may be included in the kit of FIG. 24A.

Alternatively or in addition, a volume filling material such as a braided implant 478 or flowable material may be provided in a bladder implant 479a, illustrated in FIG. 24B, or alone. The bladder implant 479a may be positioned and filled with a flowable material with an instrument 479b. The bladder 479a may include one or a plurality of the tracking sensors 52. Likewise, the instrument 479b may also include one or a plurality of the tracking sensors 52. Therefore, the position of the instrument 479b, the position of the bladder 479a, the shape of the bladder 479a, and size of the bladder 479a may all be tracked, as discussed herein. The tracking may occur for both implantation and verification of a characteristic of the implant. Various flowable materials may be positioned relative to the anatomical portion, such as to replace the nucleus 18 or the disk 416. Various implants include those described in U.S. Pat. No. 6,306,177, incorporated herein by reference.

The flowable material may be free flowed into the area of the nucleus or may be flowing into a package which is implanted in the area of the nucleus 418 or the disk 416. The material that is flowed into the implant may also be substantially cured to achieve selected characteristics, such as a selected rigidity or viscosity. As discussed herein, various instruments may be tracked relative to portions of the anatomy and portions of the implant. For example, the implant package may include tracking sensors such that various portions of the package may be tracked as it is filled with a selected flowable material. A curing source, such as a UV source, can then be tracked relative to the flowable material to determine a selected curing of the material. The curable material may include a characteristic that changes depending upon the amount of curing that occurs. Therefore, the tracking of the UV source or any other appropriate curing source can be used to achieve selected characteristics that are substantially heterogeneous, yet precisely positioned, within the implant.

As discussed above, the volume of a selected area, such as the volume of a nucleus 418 may be determined using the various modeling techniques. Therefore, a selected volume of the volume filling implant 478 may be provided to substantially precisely fill the planned removed volume of the nucleus 418.

Regardless, it will be understood that the kit 462 may provide or include a plurality of various implants. The various implants may either be part of a pre-formed kit or may be pre-selected and determined depending upon the implant selected in block 428. Therefore, the kit 462 may be substantially customized for a particular procedure because of the implant selected in block 428. The kit 462 may also include a plurality of implants from which a selection may be made after the planning and substantially intra-operatively. Nevertheless, obtaining the selected implant in block 460 may include selecting an implant from the kit 462. Alternatively, it may include designing and obtaining a substantially custom implant for a selected patient. Because the implant selected in block 428 can be modeled and altered for a selected patient and verified in block 450, the implant obtained in block 460 may be substantially customized for a particular patient.

Once the implant is obtained in block 460, a tracking sensor may be attached in block 480 to the selected implant obtained in block 460. The tracking sensor 58 may be any appropriate tracking sensor such as those discussed above, including electromagnetic, optical, and acoustic. Connecting the tracking sensor in block 480 may optionally allow for substantially dynamically determining the location of the obtained implant relative to the selected portion of the anatomy. As discussed herein, the implant may be substantially guided with selected navigation systems, such as those described above, to allow for substantially precise placement of the implant. As discussed above, the implant may be modeled in the anatomy and a selected position confirmed in block 450 for efficiency. Therefore, navigating the implant to a selected position using navigation systems may assist in assuring that the implant achieves its selected or preselected location or the target can be super-imposed on the image data. Nevertheless, it will be understood that connecting a tracking sensor to the implant is not required or may occur at any appropriate time before implanting the implant into the selected anatomical position. If a tracking sensor is used, it may be registered within the patient space. This allows the position of the implant to be determined in a real time manner.

Once the implant has been obtained, the selected area of damaged tissue may be removed in block 482. The damaged tissue being removed may generally include the tissue that is selected during selecting the procedure in block 426. Removing the damaged tissue in block 482 may include removing a selected portion of the nucleus 418, removing a selected portion of the disc 416 or other appropriate portion. It will be understood, however, that removing the damaged anatomical portion in block 482 may also include removing any selected portion of the anatomy depending upon the selected procedure such as a femoral head, a humeral head, or other appropriate portions. Therefore, removing a selected portion of the nucleus 418, as discussed herein, is merely exemplary and not intended to limit the scope of the following claims.

In removing the damaged anatomical portion in block 482, an instrument may be navigated in block 484. Navigating the instrument in block 484 may be performed using any appropriate navigation system or technique. As discussed above, the tracking sensors 58 may be connected to the instrument 52 to perform a selected procedure. It will be understood that the instrument 52 may be any appropriate instrument, such as a scalpel, a reamer, a suction device, and the like. In addition, the tracking sensors 58 may be any appropriate sensors such as optical sensors, electromagnetic sensors, acoustic sensors and the like. It will also be understood that the sensors 58 can be registered and tracked within the patient space to assist in removing a selected portion of the anatomy in block 482. This area in which tissue is to be removed may also have a template super-imposed onto the image data of the tissue that should be removed, as discussed herein. By also super-imposing the surgical instrument on the image data, a real time precise image of the amount of tissue removed can be tracked by the system. Once the procedure is planned, it will be understood that any appropriate mechanism may be used to perform the procedure. As discussed herein, the tool or the navigation of the procedure may be displayed on the monitor 10.

Alternatively, a substantially automated or robotic system may be used to perform the predetermined or pre-selected surgical plan, substantially autonomously or with supervision. Therefore, it will be understood that the selected or determined plan may be performed according to any appropriate method, such as with a user or with a robotic system. In addition, the robotic system may be a partial robotic system that includes a portion that is exterior to the patient or that is substantially contained within the patient, such as that illustrated in FIGS. 11 and 12.

Figure 25:
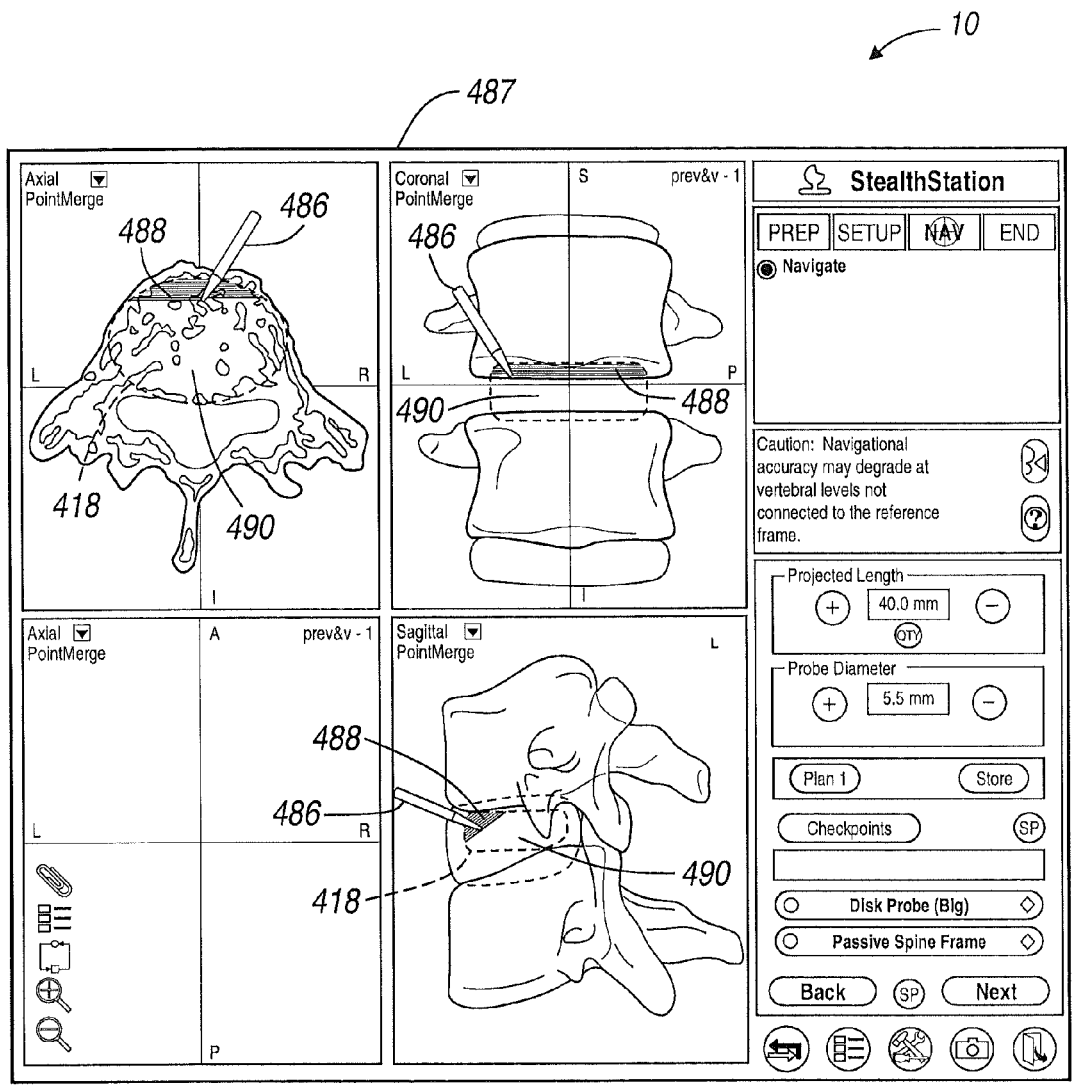
FIG. 25 is a view of a display including a model of a portion of an anatomy for navigating an instrument according to a pre-operative plan.

With reference to FIG. 25, a cutting or removing tool may be displayed as an icon 486 and may be displayed on a screen 487 on the display 10. The instrument 486 may be graphically illustrated relative to the nucleus 418. The graphical display of the instrument 486 may allow a user, such as physician, to graphically see where the instrument 486 is relative to the image of the anatomy and/or nucleus 418. For example, it may be selected to substantially remove the nucleus 418 during a procedure. Therefore, on the screen, a graphical display of the nucleus 418 may also be shown. Alternatively, the icon 486 may be displayed relative to an acquired image of the patient. In addition, a graphical display of an area removed 488 and a selected area to be yet removed 490 may be illustrated. Therefore, a physician may graphically see which portion of the nucleus 418 has not been removed 490 and which portion has been removed 488 and the boundaries of the nucleus 418. Therefore, a selected amount, that may be preselected, may be removed and which portion has and has not been removed may be illustrated on the display 10. In this way, by preselecting the volume of tissue to be removed and tracking and verifying that the tissue has been removed the selected implant may properly fit within the patient.

Navigating the instrument and illustrating it graphically 486 on the screen 488 may ensure that the selected procedure in block 426 is substantially achieved. During the selection of the procedure in block 426 it may have been selected to remove a selected volume of the nucleus 418 and navigating the instrument may ensure that the planned procedure is achieved. As discussed above the various instruments may be registered and then tracked within the selected space, such as the patient space to ensure that the location of the instrument is known and can be displayed properly as the graphical display 486.

Navigating the instrument in block 484 may assist in ensuring that the determined procedure, determined in block 426, is substantially achieved. This may be useful when providing an implant for a spinal procedure, such as replacing the nucleus 418. Briefly the nucleus 418 may include a selected volume that is desirable to be substantially replaced. Therefore determining the procedure in block in 426 may include determining a selected volume of the nucleus 418 to be removed. Using the tracking system, the instrument 486 may be displayed on the screen 487 to be used to ensure that the determined procedure is performed. This may allow the selected implant selected in block 428 to substantially achieve the selective results determined in block 450.

After navigating the instrument in block 484 to remove the damaged anatomical portion in block 482, the implants obtained in block 460 may be positioned in block 492. Positioning the implant may also performed with use of the tracking system. As discussed above a tracking sensor may be connected in block 480 to the implant prior to attempting to position the implant in block 492. Also the implant may be substantially positioned by visualization of a user, such as a physician. Regardless after the damaged tissue is removed in block 482 the implant can be positioned in block 492.

Figure 26:
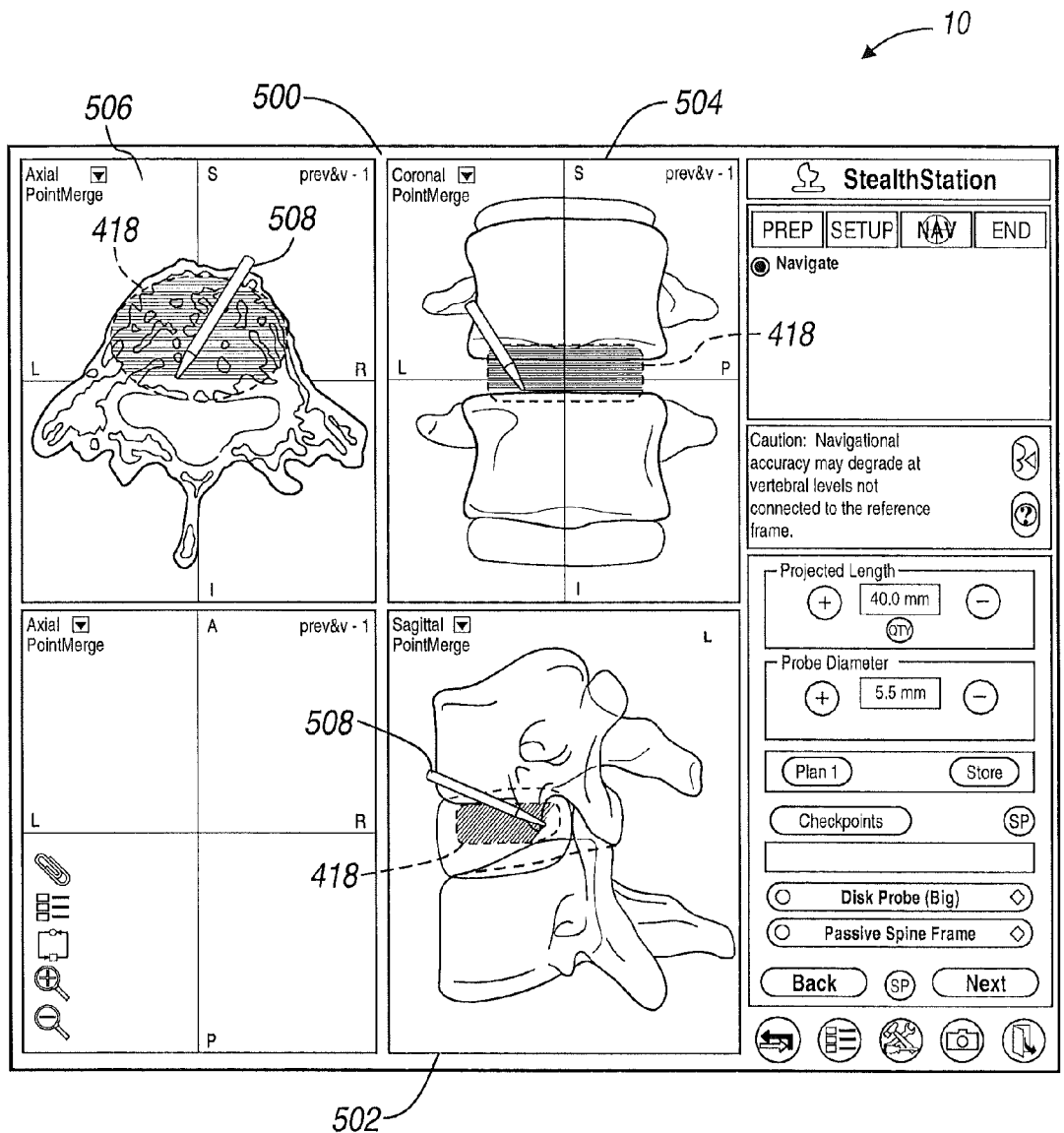
FIG. 26 is a view of a display including a model of a portion of an anatomy for navigating an instrument according to a pre-operative plan.

With reference to FIG. 26, the display 10 may display an implant navigation screen 500. The implant navigation screen 500 may include a plurality of views of the selected portion of the anatomy such as a sagittal plane view 502, a coronal plane view 504 and an axial view 506. Each of these views may show the removed nucleus 416 as a darkened area, or any appropriate manner. Alternatively, the representation may be of the area to be filled with the implant. In addition an implant instrument 508 may also be graphically illustrated. The implant instrument 508 may also be generally navigated and may include tracking sensors, such as the location sensors 58. Again, it will be understood that the location sensors 58 may be any appropriate location sensors and may be used to create the graphical view of the implantation instrument 508 in a substantially correct location. In addition, the implant instrument 508, such as the instrument 479b (FIG. 24B), may include a plurality of tracking sensors. The plurality of tracking sensors may be positioned along a length or shape of the implant instrument 508 such that the implant instrument may be substantially flexible, yet a precise location of each portion of the implant instrument may be determined and illustrated on the screen 500.

A selected implant, such as the substantially deformable braid implant 478 may be passed through the instrument graphically illustrated as 508 and positioned in the area where the nucleus 418 was removed. Therefore a pre-selected volume of the deformable tissue material 478 may pass through the instrument that may be navigated to a selected position using the display 500. Due to the determination of the procedure, the proper volume of the tissue implant can be positioned in the selected portion of the anatomy to ensure that selected results are achieved.

Alternatively, a deformable or shape memory implant, such as those described in U.S. Pat. No. 6,620,196 may be deformed and passed through an instrument that is graphically illustrated as 508. The shape memory implant may be placed under a force to deform it to allow it to be passed through a selected portion of the anatomy into the area to which the nucleus 418 was removed. Once the forces have been removed, such as when the implant passes out of the instrument 508, the implant 474 may achieve a substantially shape memory shape to fill the area of the removed nucleus 418.

As briefly discussed above (FIG. 24B), various implants may be implanted that include a material, such as a flowable or curable material, that is positioned within the portion of the anatomy, such as to replace the nucleus 418 where the flowable or curable material may be positioned in the bladder 479a that is positioned within the portion of the anatomy or the flowable material may simply positioned within the portion of the anatomy. If the material is positioned within the bladder 479a, the bladder may include a plurality of tracking sensors, such as an electromagnetic tracking sensors, such that a size, geometry and the like of the latter may be determined during the filling of the bladder. Therefore, during the filling of the bladder, it can be determined, with the tracking sensors and the tracking array, the size, shape, position, and other characteristics of the bladder as it is being filled. This allows the planned or preselected procedure to be performed by tracking the filling, positioning, and the like of the bladder 479a during the operative procedure.

In addition, the flowable material that may be flowed into the bladder or into the anatomy itself may include any appropriate material. For example, substantially natural materials such as bone particles or the like may be injected, alternatively, substantially synthetic materials may be implanted. For example, a curable material, such as polymer that is cured with a radiation, such as UV radiation, or a polymer that is cured with an activation component, such as a generally known bone cements, may be used.

If a curable material is used that is cured with a selected curing procedure, such as radiation with UV radiation, tracking of a probe which applies UV radiation to the curable material may be performed. This may allow substantially precise curing of a selected area of the implant to a selected amount. For example, it may be selected to cure a substantially posterior portion of the implant to a selected amount to provide a selected characteristic of the material while curing an anterior portion of the implant to a different amount to provide a substantially different characteristic of the material. For example, a longer curing time may make the curable material substantially more viscous or rigid and that a shorter cured time portion of the material is substantially soft relative to the longer cured time material. Therefore, the curing probe, such as the UV probe, can be substantially precisely navigated relative to the curable material to allow for precise curing times of various portions of the material to provide various types of characteristics of different regions of the material.

It will be understood, however, that various types of radiation may be used, such as gamma or electron beam, to cure portions of the material. Nevertheless, being able to substantially precisely locate and track the position of the curing probe may allow for a substantially heterogeneous implant, which is one that includes different characteristics for different portions of the implant. Also, other fillers, such as inorganic or organic fillers, including calcium carbonate, titanium dioxide and the like may be provided in a substantially precise places to alter the viscosity of a material in that location. Again, the positioning of the probe which introduces the materials into the implant may be tracked with tracking sensors. In addition, or alternatively, various reinforcing materials, such as metallic and non-metallic meshes, may be used to reinforce portions of the implant to provide a selected characteristic at a selected portion of the implant.

In addition, such as with the use of an inflatable bladder, the bladder may include portions that may be adhered or interconnected with the curable material such that the bladder may move at a selected rate with the curable material or a portion of the material, including a selected characteristic, is held relative to a selected bladder portion. Therefore, it will be understood, as discussed above, that the bladder may be substantially navigated to ensure that the portion of the material that is engaging a selected portion of the bladder is in a selected area, dimension, and the like.

It will be understood that various other portions may be navigated as well, such as coatings for the implant, modular portions of the implant and the like. It will be further understood that the tracking assembly may be used to substantially position an implant to a substantially minimally or small invasive procedure without substantial visualization or visually guiding of the implantation. Therefore, the system 400 can be used to plan a procedure and selection of an implant according to various selected characteristics. For example, the system 400 may model the anatomy through a substantially dynamic modeling and chose an implant to achieve the desired dynamic model. Thereafter, the system 400 may be used to substantially guide the implantation and procedure, substantially non-visually, to achieve the selected results. Therefore, visual implantation of the implant may not be necessary due to various features, such as the tracking sensors and the like.

Regardless of the implant selected, the implant may be selected due to the determined procedure to ensure that the volume removed in block 482 may be substantially filled or a selected anatomical position be obtained after positioning the implant in block 492. It may be possible that the determination of the procedure in block 426 and the selection of the implants in block 428 that the implant may be pre-selected without trialing to ensure a proper or selected fit. Therefore, positioning an implant may be done in substantially a single step without necessity of trialing.

After positioning the implant in block 492, the position of the implant may be confirmed in block 512. The confirmation of the position of the implant can be confirmed in block 512 intra-operatively or post-operatively. If the position of the implant is desired to be confirmed intra-operatively it may be confirmed with an instrument such as the fluoroscopic imaging system 16. The imaging system 16 may be used to obtain an image of the selected area of the anatomy and display the image of the selected area of anatomy on the screen 10. The implant may be substantially viewable using the x-ray instrument or may include markers, such as tantalum markers, dyes, or other appropriate radio-opaque materials, to ensure that the instrument or implant may be viewed post-operatively. Regardless, the confirmation may be used to ensure that the implant has been positioned in the predetermined position.

In addition, as mentioned above, various other wireless sensors may be positioned in the implant. For example, electromagnetic tracking sensors may be positioned in the implant, such that after the implant is positioned a determination of a location, orientation and the like may be determined for the implant using the tracking system 44. Therefore, the position of the implant may be confirmed using selected procedures, such as obtaining an image of the implant, which may include substantially radio-opaque portions or determining a location of the implant using various wireless sensors. As discussed above, the implant, which may include the bladder 479a or other appropriate portion, may include the tracking sensors 58, such as electromagnetic sensors, that may be tracked by a tracking array. Therefore, the tracking array, either intra or post operatively, may be used to track a position or other characteristic of the implant relative to the anatomy to ensure that the position of the implant is the preselected position of the implant. In addition, the tracking sensors may be used to ensure that a selected volume, such as filled volume of the bladder, has been achieved. Therefore, various portions, such as radio opaque material, including dyes, tantalum or other marker, and the like may be viewed using an X-ray source and/or tracking sensors may be used to track a position of the implant such that the position or characteristic of the implant can be substantially verified or confirmed after the implant has been positioned relative to the anatomy to ensure that the implant has been positioned in a preselected portion of the anatomy in a preselected manner.

In addition or alternatively, the probe 68 may also be used to indicate or touch a portion of plurality of points of the implant, such that the work station 38 or the system may be used to determine the precise location of the implant. The precise location of the implant may then be modeled relative to the anatomical portion and displayed on the screen 10. Regardless, it will be understood that the implant may be modeled or viewed as an image on the screen 10 relative to the anatomy to insure that the implant is positioned in a selected position. In addition, a predetermined or preselected position may be superimposed or underimposed relative to the image of the patient to insure that a substantially matching of the implant implanted position is relative to the selected position.

In addition, further modeling may occur in the confirming of the position in block 512 to ensure that the dynamic movement of the implant as positioned will achieve selected results. In addition, a virtual or digital subtraction method may also be used to determine or confirm a selected location of the implant. Such a system is generally described in U.S. patent application Ser. No. 10/116,631, entitled Method And Apparatus For Virtual Digital Subtraction Angiography, filed Apr. 4, 2002 the disclosure of which is incorporated herein by reference. Briefly, the work station 38 may be used to intraoperatively subtract or compare a preoperative or planned position with the post implantation position. For example, an image of the patient may be taken preoperatively for the planning procedure and an image of the patient may be taken after the implant has been positioned, both may also be substantially intraoperatively. The two images may then be compared and both may be enhanced substantially virtually to substantially insure a selected position of the implant or a selected position of the anatomy after positioning of the implant. The images may be taken in any appropriate manner, such as with a fluoroscope or MRI, or the like. Therefore, the images may be substantially virtually compared along a plurality of planes, such as two-dimensional planes, or comparing various three-dimensional models of the anatomy.

Therefore, it will be understood that the implant may be positioned in any appropriate manner as discussed above, and the position of the implant may be confirmed in block 512. The confirmation of the position of the implant may be performed in any appropriate manner, such as with imaging the implant relative to a previous planned image or modeling the implanted anatomy or implant relative to a previous image. Regardless of the method used to confirm the position of the implant, the confirmed position of the implant may be done substantially intraoperatively to allow for a substantially precise placement of the implant and a correct surgical procedure.

The position, correct volume, geometry, and other appropriate considerations, of the implant may also be confirmed with a track-able probe or other instrument. The position of a probe may be determined by use of tracking sensors positioned relative to the probe that may be used to touch or determine the position of the implant. This allows determining a position of the implant without connecting tracking sensors directly to the implant. Tracking sensors, however, may be included in the implant to be tracked to ensure proper positioning of the implant.

After the position is confirmed by Yes in block 514, the patient may recover in block 516. It will be understood that the confirmation of positioning of the implant may result in a No in block 518 and an additional placing in block 492 occurs. Therefore, positioning the implant may be iterative until the decisions block 512 is Yes 514. Because the procedure was predetermined or preselected in block 426, the implant may substantially be in a position necessary to achieve selected results, such as a range of motion. Therefore, the confirmation in block 512 may simply assure the user that the implant has been positioned in the selected location.

In addition, the patient recovering in block 516 may be reduced due to the planning and reduced trialing. The planning procedure can help ensure that an implant that may achieve a selected result in a first instance rather than providing a plurality of trialing instruments to attempt to achieve a selected result. As discussed above, a selected volume of the anatomy may be removed substantially precisely using the planning and navigation systems. Then the implant may be selected to achieve a selected result, such as substantially precisely replacing the resected anatomical portion. Therefore, the trialing may be substantially reduced or eliminated. In addition, optionally, if the implant is not confirmed to be in a proper position then the implant may be repositioned or positioned again in block 492. Only after proper positioning of the implant or a confirmation thereof may the patient be removed from the operative theater. This may also reduce a need for a later procedure and assist in the recovering of the patient.

It will be understood that the above-described system may be used with any appropriate implants or for any appropriate implantation device or system. For example, a bladder or other container device may be positioned relative to a selected portion of the anatomy, such as between the two vertebrae 406, 408 to be filled with a material. Various systems may be used, such as those described in U.S. Pat. Nos. 6,443,988; 6,306,177; and International Publication No. WO97/26847, each incorporated herein by reference. The bladder may be positioned relative to a selected portion of the anatomy after the planning procedure has been determined and only a selected or determined volume of material is then positioned within the bladder. Therefore, the system may be used to preselect or predetermine the volume of fluid to be positioned in the bladder to allow for a selected result. Alternatively, other inflatable devices may include those disclosed in U.S. Pat. Nos. 6,663,647; 6,641,587; 6,623,505; 6,607,544; 6,423,083; 6,235,043; and 5,927,015, each incorporated herein by reference.

In addition, various materials may be injected relative to a selected portion of bone, such as bone cements and the like that may fill a selected void or volume. Again, as discussed above, a selected volume or bounds of material may be selected or determined to perform the procedure. Therefore, the procedure may be planned after determining a selected volume of fluid to be injected and then injecting the selected fluid. Various systems for positioning may include those described in U.S. Pat. Nos. 6,613,054 and 6,048,346, each incorporated herein by reference. Therefore, a selected area may be determined to include a selected volume and the procedure may be planned after determining a selected volume and positioning the selected volume may then be navigated with the system.

In addition, various other materials, such as various hydrogels or dehydrated hydrogel materials may be positioned relative to a selected portion of the anatomy. For example, an elastic, elastomeric, and/or hydrogel material may be injected into a selected portion of the anatomy. Various methods and systems may include those described in U.S. Pat. Nos. 5,800,549 and 5,534,028, each incorporated herein by reference.

Therefore, it will be understood that the system 400 may be used to determine a selected volume, size, geometry, and the like that can be filled with any appropriate implant. The system 400 can be used to plan a volume appropriate to be implanted and the procedure may then be performed according to the plan. In addition, as discussed above, the system may be used to position a selected material, such as bone morphogenic proteins, antibiotics, other medications, and other bioactive materials, relative to a selected portion of the anatomy and the system may be used to position the materials in a selected delivery device relative to the anatomy.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical system for use in a procedure to implant a prosthesis relative to an anatomy, comprising:
 an imaging device to obtain image data of a selected portion of the anatomy;
 a planning system including a processor to execute operations relating to said image data;
 wherein said imaging device is operable to generate image data of the selected portion of the anatomy prior to the procedure and the processor forms a model of the selected portion of the anatomy in a coordinate system based on the image data;
 a display displays a portion of the anatomy to be removed in the model; and
 wherein said processor determines a volume of the selected portion of the anatomy based on at least three measurements taken from the model within the coordinate system and selects a procedure to be performed on the selected portion of the anatomy and selects the prosthesis to be implanted based on the determined volume.

2. The surgical system of claim 1, further comprising a user input device such that said processor may receive an instruction from a user and execute the instruction to perform a process.

3. The surgical system of claim 2, wherein said user input device includes at least one of a keyboard, a mouse, a pointing device, a touch sensitive display, or combinations thereof.

4. The surgical system of claim 2, wherein said planning system further includes a work station including said user input device; and
a storage system operable to store a selected dataset including said image data of the selected portion of the anatomy.

5. The surgical system of claim 1, wherein said imaging device is selected from the group consisting of a fluoroscopic C-arm, a magnetic resonance imaging system, an X-ray system, an ultrasound system, a computed tomography system, and combinations thereof.

6. The surgical system of claim 1, wherein said planning system is operable to display said model on said display, and said display displays a portion of the anatomy to be completely removed in the model along with a portion of the anatomy yet to be removed.

7. The surgical system of claim 1, further comprising a navigation system including:
a tracking system; and
a tracking sensor;
wherein said navigation system is operable with said planning system to perform the procedure according to a selected plan described with said planning system.

8. The surgical system of claim 7, wherein said tracking system is at least one of an electromagnetic tracking system, an optical tracking system, an acoustic tracking system, or combinations thereof.

9. The surgical system of claim 1, wherein said planning system is operable to determine at least one of a selection of a procedure, selection of an implant, or planning of a selected procedure.

10. The surgical system of claim 1, wherein said image data from said imaging device is displayable on said display as an image;
wherein said image on said display allows at least one of a selection of a procedure, selection of an implant, or planning of a selected procedure.

11. The surgical system of claim 1, further comprising:
a navigation system including a tracking array and a tracking sensor;
wherein said planning system is operable to plan the procedure with said image data;
wherein said navigation system is operable to navigate an instrument for substantially performing the planned procedure.

12. The surgical system of claim 1, further comprising:
a navigation system and a tracking sensor;
wherein said tracking sensor is affixed to an implant;
wherein said planning system is operable to determine an implanted characteristic of said implant;
wherein said navigation system is operable to determine a location of said tracking sensor to navigate a characteristic of said implant to allow implantation of said implant with a selected characteristic.

13. The surgical system of claim 1, further comprising:
an implant kit including a plurality of implants;
wherein said planning system is operable to select at least one of the plurality of the implants to be positioned in the selected portion of the anatomy to achieve a result.

14. The surgical system of claim 13, further comprising a memory system wherein said memory system is operable to save the model formed from said image data and a planned procedure for retrieval.

15. The surgical system of claim 13, wherein said planning system substantially autonomously selects the at least one of the plurality of the implants based on the volume of the selected portion of the anatomy measured from the model.

16. The surgical system of claim 13, wherein said planning system selects the at least one of the plurality of the implants for at least one of confirmation or selection by a user.

17. The surgical system of claim 1, further comprising a template program, wherein said template program is executable by said planning system for planning a selected procedure.

18. The surgical system of claim 17, wherein said template program allows said planning system to select at least one of a size, a geometry, a type or combinations thereof of an implant.

19. The surgical system of claim 17, wherein said template program allows a user to select at least one of a size, a shape, a type, or combinations thereof.

20. The surgical system of claim 1, wherein said planning system includes a tracking system;
wherein said planning system is operable to plan at least one of a selection of an implant, a volume to be removed, a geometry to be removed, or combinations thereof;
wherein said tracking system allows for tracking of at least one of the removal of the selected volume, a shape of the selected implant, or the selected geometry.

21. The surgical system of claim 1, further comprising an implant including at least one of a spinal implant, a knee implant, a hip implant, a shoulder implant, a wrist implant, a hand implant, an arm implant, or combinations thereof.

22. A surgical system operable to obtain image data for use in a procedure to position a prosthesis in a selected portion of an anatomy, comprising:
a planning system including a processor to execute operations relating to the image data and forming an image based model of the selected portion of the anatomy;
a display that displays the image based model;
wherein the image data relates to the selected portion of the anatomy prior to the procedure;
wherein said planning system is operable to measure a selected dimension of the selected portion of the anatomy from the image based model and to select a prosthesis based upon the measurement to substantially mimic the selected dimension and to plan the procedure to achieve a selected characteristic of the prosthesis at least in part based upon the selected dimension, and the display displays an area of the anatomy to be completely removed and an area of the anatomy yet to be removed.

23. The surgical system of claim 22, further comprising:
an implant including at least one of an implant dimension, type, geometry, or combinations thereof;
wherein said planning system is operable to select the implant including the at least one of an implant dimension, type, geometry, or combinations thereof, and placement to substantially fit the selected dimension of the selected portion of the anatomy.

24. The surgical system of claim 23, further comprising:
a tracking system to track the implant during placement of the implant to confirm placement of the implant.

25. The surgical system of claim 22, further comprising a user input device such that said processor may receive an instruction from a user and execute the instruction to perform a process.

26. The surgical system of claim 25, wherein said planning system further includes a work station including said user input device; and
- a storage system operable to store a selected dataset including the image data of the selected portion of the anatomy.

27. The surgical system of claim 26, wherein said planning system further includes an implant storage system, wherein said implant storage system includes a data set of a plurality of implants;
- wherein said planning system is operable to compare said data set of the plurality of implants to said image data from the selected portion of the anatomy to select at least one of the plurality of the implants for implantation.

28. The surgical system of claim 22, further comprising:
- an imaging system operable to collect image data regarding the selected portion of the anatomy;
- wherein said processor is operable to form a model of the selected portion of the anatomy with the image data obtained by the imaging system.

29. The surgical system of claim 28, wherein the imaging system is selected from the group consisting of a fluoroscopic C-arm, a magnetic resonance imaging system, an X-ray system, an ultrasound system, a computed tomography system, and combinations thereof.

30. The surgical system of claim 29:
- wherein said planning system is operable to display said model on said display.

31. The surgical system of claim 22, further comprising a navigation system including:
- a tracking system; and
- a tracking sensor;
- wherein said navigation system is operable with said planning system to perform the procedure according to a selected plan described with said planning system.

32. The surgical system of claim 31, wherein said tracking system is at least one of an electromagnetic tracking system, an optical tracking system, an acoustic tracking system, or combinations thereof.

33. The surgical system of claim 22, wherein said planning system is operable to determine at least one of a selection of a procedure, selection of an implant, planning of a selected procedure, or combinations thereof.

34. The surgical system of claim 22,
- wherein the image based model on said display allows at least one of a selection of a procedure, selection of an implant, planning of a selected procedure, or combinations thereof.

35. The surgical system of claim 22, further comprising:
- a navigation system including a tracking array and a tracking sensor;
- wherein said planning system is operable to plan the procedure with the image data;
- wherein said navigation system is operable to navigate an instrument for substantially performing the planned procedure.

36. The surgical system of claim 22, further comprising:
- a navigation system and a tracking sensor;
- wherein said tracking sensor is affixed to an implant;
- wherein said navigation system is operable to determine a location of said tracking sensor to navigate a characteristic of said implant to allow implantation of said implant with a selected implanted characteristic.

37. The surgical system of claim 22, further comprising:
- an implant kit including a plurality of implants;
- wherein said planning system is operable to select at least one of the plurality of the implants to be positioned in the selected portion of the anatomy to achieve a result.

38. The surgical system of claim 37, wherein said plurality of implants include a plurality of implants of a hip implant, a knee implant, a shoulder implant, a spinal implant, and combinations thereof.

39. The surgical system of claim 37, further comprising a memory system wherein said memory systems operable to save a modeled portion formed from said image data and a planned procedure for retrieval.

40. A surgical system for use in a procedure to position an implant relative to an anatomy, comprising:
- an imaging device to obtain image data of a selected portion of a spine of the anatomy;
- a planning system including a processor to execute operations relating to said image data;
- a display for displaying an area of the anatomy to be removed;
- wherein said imaging device is operable to generate image data of the selected portion of the anatomy prior to the procedure; and
- wherein said processor determines a selected dimension in said image data from said imaging device and selects an implant based upon the determined selected dimension; and
- an implant configured to be positionable relative to the selected portion of the spine based on the selected dimension, the implant having a characteristic that is adjustable during or after being positioned relative to the selected portion of the anatomy,
- wherein the characteristic includes a configuration of the implant that has an implanted configuration different than an unimplanted configuration.

41. The surgical system of claim 40 further comprising:
- a confirmation system to compare at least one of an implanted status and position of said implant to a selected planned status or position determined with said planning system.

42. The surgical system of claim 41, wherein said confirmation system includes a virtual digital subtraction system;
- wherein said imaging device is operable to obtain image data of the selected portion of the spine after said implant is positioned relative to said selected portion of the spine and compare the after image data to the image data used by said planning system to plan the procedure.

43. The surgical system of claim 41, wherein said confirmation system is operable to compare image data of the selected portion of the spine in at least one of two dimensions, three dimensions, a coronal plane, an axial plane, a sagittal plane, or combinations thereof.

44. The surgical system of claim 41, further comprising:
- a tracking system operable to track a position of said implant with at least one of an electromagnetic sensor, an acoustic sensor, an optical sensor or combinations thereof.

45. The system of claim 41, wherein the confirmation system confirms the characteristic of the implant after the implant is implanted.

46. The surgical system of claim 40, wherein said planning system is operable to plan an alignment of said implant relative to the selected portion of the spine during an operative procedure.

47. The surgical system of claim 46, wherein said alignment is along at least one of a coronal plane, a sagittal plane, an axial plane or combinations thereof.

48. The surgical system of claim 40, wherein said implant includes a radio-opaque portion operable to be imaged with said image device.

* * * * *